(12) United States Patent
Kjeldsen et al.

(10) Patent No.: US 11,208,452 B2
(45) Date of Patent: Dec. 28, 2021

(54) INSULINS WITH POLAR RECOMBINANT EXTENSIONS

(71) Applicant: Novo Nordisk A/S, Bagsvaerd (DK)

(72) Inventors: Thomas Boerglum Kjeldsen, Virum (DK); Thomas Hoeg-Jensen, Klampenborg (DK); Tine Nygaard Vinther, Frederiksberg (DK); Frantisek Hubalek, Herlev (DK); Ingrid Pettersson, Frederiksberg (DK)

(73) Assignee: Novo Nordisk A/S, Bagsvaerd (DK)

(*) Notice: Subject to any disclaimer, the term of this patent is extended or adjusted under 35 U.S.C. 154(b) by 92 days.

(21) Appl. No.: 15/577,990

(22) PCT Filed: Jun. 2, 2016

(86) PCT No.: PCT/EP2016/062514
§ 371 (c)(1),
(2) Date: Nov. 29, 2017

(87) PCT Pub. No.: WO2016/193380
PCT Pub. Date: Dec. 8, 2016

(65) Prior Publication Data
US 2018/0291076 A1    Oct. 11, 2018

(30) Foreign Application Priority Data

Jun. 2, 2015 (EP) .................... 15170337
Jul. 10, 2015 (EP) .................... 15176207

(51) Int. Cl.
*C07K 14/62* (2006.01)
*A61P 3/10* (2006.01)
*A61K 38/00* (2006.01)

(52) U.S. Cl.
CPC .............. *C07K 14/62* (2013.01); *A61P 3/10* (2018.01); *A61K 38/00* (2013.01)

(58) Field of Classification Search
CPC .................... C07K 14/62; A61K 38/28
See application file for complete search history.

(56) References Cited

U.S. PATENT DOCUMENTS

| | | | |
|---|---|---|---|
| 3,914,252 A | 10/1975 | Gordon | |
| 7,404,956 B2 | 7/2008 | Peters et al. | |
| 8,492,530 B2 | 7/2013 | Schellenberger et al. | |
| 8,697,396 B2 | 4/2014 | Dall'Acqua et al. | |
| 10,537,644 B2 | 1/2020 | Huang et al. | |
| 2003/0162949 A1 | 8/2003 | Cox | |
| 2004/0180054 A1 | 9/2004 | Kim et al. | |
| 2005/0233417 A1 | 10/2005 | Cooper et al. | |
| 2005/0287153 A1 | 12/2005 | Dennis | |
| 2006/0094083 A1 | 5/2006 | Choi et al. | |
| 2006/0094655 A1 | 5/2006 | Guyon et al. | |
| 2006/0183197 A1 | 8/2006 | Andersen et al. | |
| 2006/0276633 A1 | 12/2006 | Jung et al. | |
| 2008/0057004 A1 | 3/2008 | Bell et al. | |
| 2009/0036353 A1 | 2/2009 | Behrens et al. | |
| 2010/0069605 A1 | 3/2010 | Hoeg-Jensen et al. | |
| 2010/0239554 A1* | 9/2010 | Schellenberger ..... C07K 14/001 424/94.3 |
| 2012/0116056 A1 | 5/2012 | Sun et al. | |
| 2013/0028918 A1 | 1/2013 | Song et al. | |
| 2014/0227264 A1 | 8/2014 | Hamilton et al. | |
| 2015/0037359 A1 | 2/2015 | Schellenberger et al. | |
| 2015/0158905 A1 | 6/2015 | Martin | |
| 2016/0000932 A1 | 1/2016 | Gegg et al. | |
| 2018/0161448 A1 | 6/2018 | Heo et al. | |
| 2018/0291076 A1 | 10/2018 | Kjeldsen et al. | |
| 2020/0261595 A1 | 8/2020 | Moeller Tagmose et al. | |

FOREIGN PATENT DOCUMENTS

| | | |
|---|---|---|
| CN | 1604965 A | 4/2005 |
| CN | 102666586 A | 9/2012 |
| DE | 257197 A1 | 6/1988 |
| DE | 286509 | 1/1991 |
| EP | 1996220 A2 | 12/2008 |
| EP | 2164873 A1 | 3/2010 |
| EP | 3260139 | 12/2017 |
| JP | 2008528549 A | 7/2008 |
| JP | 2008530178 A | 8/2008 |
| KR | 20080095141 A | 10/2008 |
| WO | 91/01743 A1 | 2/1991 |
| WO | 92/09690 A2 | 6/1992 |
| WO | 97/11178 A1 | 3/1997 |
| WO | 98/22577 A1 | 5/1998 |
| WO | 0103737 A1 | 1/2001 |
| WO | 01/45746 A2 | 6/2001 |

(Continued)

OTHER PUBLICATIONS

Jochen G. Salfeld, "Isotype Selection in Antibody Engineering," Nature Biotechnology, 2007, vol. 25, pp. 1369-1372.
Singh et al., Novel Approaches and Strategies for Biologics, Vaccines and Cancer Therapies, 1st Edition, Jan. 5, 2015, p. 134.
Abbasi et al. "Dendrimers: synthesis, applications, and properties." Nanoscale Research Letters. 2014 vol. 9 No 1; 247 pp. 1-10. EP SR.
Berg et al. "Biochemistry" 2002. W.H.Freeman and Co, New York p. 925, figure 33.8. EP SR.
Berthelmann et al. "Versatile C3-symmetric scaffolds and their use for covalent stabilization of the foldon trimer" Organic and Biomolecular Chemistry. 2014 vol. 12 No 16. pp. 2606-2614. EP SR.
Life Technologies. "Sulfhydryl-reactive Crosslinker Chemistry." 2015. Accessed Mar. 6, 2015. https://www.lifetechnologies.com/in/en/home/life-science/protein-biology/protein-biology-learning-center/protein-biology-resouice-library/pierce-protein-methods/sulfhydryl-reactive-crosslinker-chemistry.html. ISR.
Kontermann R. E. et al., Strategies for extended serum half-life of protein therapeutics, Current Opinion in Biotechnology, 2011, vol. 22, No. 6, pp. 868-876.

(Continued)

*Primary Examiner* — Gyan Chandra
(74) *Attorney, Agent, or Firm* — Jianjie Hu

(57) ABSTRACT

The present invention relates to novel insulins or insulins analogues that are extended with predominantly sequences of polar amino acid residues in order to improve the half-life and stability of the drug substance. The invention also provides pharmaceutical compositions comprising such drug substances, and relates to the use of such drug substances for the treatment or prevention of medical conditions relating to diabetes.

7 Claims, 4 Drawing Sheets

Specification includes a Sequence Listing.

(56) References Cited

FOREIGN PATENT DOCUMENTS

| | | | |
|---|---|---|---|
| WO | 02055532 | A2 | 7/2002 |
| WO | 02/077036 | A2 | 10/2002 |
| WO | 03/070765 | | 8/2003 |
| WO | 04029207 | A2 | 4/2004 |
| WO | 2004101739 | A2 | 11/2004 |
| WO | 2005001025 | A2 | 1/2005 |
| WO | 2005047334 | A1 | 5/2005 |
| WO | 2005047335 | A1 | 5/2005 |
| WO | 2005047336 | A1 | 5/2005 |
| WO | 2005047337 | A1 | 5/2005 |
| WO | 2006048777 | A2 | 5/2006 |
| WO | 2006/081249 | A2 | 8/2006 |
| WO | 2006/087354 | | 8/2006 |
| WO | 2006107124 | A1 | 10/2006 |
| WO | 2007/073486 | A2 | 6/2007 |
| WO | 2007068906 | A2 | 6/2007 |
| WO | 2007/103515 | A2 | 9/2007 |
| WO | 2008019368 | A2 | 2/2008 |
| WO | 2008/049711 | A1 | 5/2008 |
| WO | 2008/049931 | A1 | 5/2008 |
| WO | 08052108 | A2 | 5/2008 |
| WO | 08092117 | A2 | 7/2008 |
| WO | 2008147143 | A2 | 12/2008 |
| WO | 2008147456 | A2 | 12/2008 |
| WO | 2009015345 | A1 | 1/2009 |
| WO | 2009/023270 | A2 | 2/2009 |
| WO | 2009/053368 | A1 | 4/2009 |
| WO | 09155513 | A2 | 12/2009 |
| WO | 2010/001196 | A1 | 1/2010 |
| WO | 2010011096 | A2 | 1/2010 |
| WO | 2011018227 | A2 | 2/2011 |
| WO | 2011059684 | A1 | 5/2011 |
| WO | 2011122921 | A2 | 10/2011 |
| WO | 2011/144756 | A1 | 11/2011 |
| WO | 2012008779 | A2 | 1/2012 |
| WO | 2012138920 | A1 | 10/2012 |
| WO | 2013004842 | A2 | 1/2013 |
| WO | 2013170272 | A2 | 11/2013 |
| WO | 2014/195452 | A1 | 12/2014 |
| WO | 2015/038938 | A1 | 3/2015 |
| WO | 15081073 | A2 | 6/2015 |
| WO | 15132364 | A1 | 9/2015 |
| WO | 2016/042093 | A1 | 3/2016 |
| WO | 2016133372 | A2 | 8/2016 |
| WO | 2016178905 | A1 | 11/2016 |
| WO | 2016193380 | A1 | 12/2016 |
| WO | 2017031034 | A2 | 2/2017 |
| WO | 2017055582 | A1 | 4/2017 |
| WO | 2018185131 | A2 | 10/2018 |

OTHER PUBLICATIONS

Huang C., Receptor-Fc fusion therapeutics, traps, and MIMETIBODY technology, Current Opinion in Biotechnology, 2009, vol. 20, No. 6, pp. 692-699.

Chantalat L. et al., The Crystal Structure of Wild-Type Growth Hormone at 2.5 A resolution, Protein and Peptide Letters, 1995, vol. 2, No. 2, pp. 333-340.

de Vos A. M. et al., Human growth hormone and extracellular domain of its receptor: crystal structure of the complex, Science, 1992, vol. 255, pp. 306-312.

Cunningham B. C. et al., Rational design of receptor-specific variants of human growth hormone, Proceedings of the National Academy of Sciences, National Academy of Sciences, U.S., 1991, vol. 88, No. 8, XP00020231, pp. 3407-3411.

Cunningham B. C. et al., High-Resolution Epitope Mapping of hGH-Receptor Interactions by Alanine-Scanning Mutagenesis, Science, 1989, vol. 244, No. 4908, pp. 1081-1085.

Kasimova M. R. et al., NMR Studies of the Backbone Flexibility and Structure of Human Growth Hormone: A Comparison of High and Low pH Conformations, Journal of Molecular Biology, 2002, vol. 318, pp. 679-695.

Lee C. H. et al., Expression and characterization of human growth hormone-Fc fusion proteins for transcytosis induction, Biotechnology and Applied Biochemistry, 2007, vol. 46, pp. 211-217.

Wells, "Binding in the Growth Hormone Receptor Complex," Proc. Natl. Acad. Sci. USA, 1996, vol. 93, pp. 1-6.

Yang et al., "Activation of Growth Hormone Receptors by Growth Hormone and Growth Hormone Antagonist Dimers insights into Receptor Triggering," Mol. Endocrinol., 2008, vol. 22, No. 4, pp. 978-988.

Pearce et al., "Growth Hormone Binding Affinity for Its Receptor Surpasses the Requirements for Cellular Activity," Biochemistry, 1999, vol. 38, pp. 81-89.

Chen et al. "Fusion protein linkers: property, design and functionality." Advanced drug delivery reviews, Oct. 2013, vol. 65, No. 10, pp. 1357-1369.

Jochen G. Salfeld, "Isotype Selection in Antibody Engineering," Nature Biotechnology, Dec. 2007, vol. 25, pp. 1369-1372.

Arakawa, Takeshi et al. "A Plant-Based Cholera Toxin B Subunit—Insulin Fusion Protein Protects Against the Development of Autoimmune Diabetes." Nature Biotechnology 1998 vol. 16(10) pp. 934-938.

Podust et al., Extension of in vivo half-life of biologically active peptides via chemical conjugation to XTEN protein polymer, Protein Engineering, Design & Selection, Oct. 16, 2013, vol. 26, No. 11, pp. 743-753.

Nomura et al., "Trivalent ligands for CXCR4 bearing polyproline linkers show specific recognition for cells with increased CXCR4 expression," Org. Biomol. Chem. 2015, vol. 13, pp. 8734-8739.

* cited by examiner

GQEPGAPHGE PHGAPHGEPH GAPQGQEPGQ EPGQEPGQAP GQEPGEHPGA PQGAPQGQEP
GAPQGQEPGA PHGEHPGEHP GQEPGAPHGE PHGAPHGEPH GAPQGQEPGQ EPGQEPGQAP
GQEPGEHPGA PQGAPQGQEP GAPQGQEPGA PHGEHPGEHP GQEPGAPHGE PHGAPHGEPH
GAPQGQEPGQ EPGQEPGQAP (SEQ ID NO.:21)

INSULINS WITH POLAR RECOMBINANT EXTENSIONS

CROSS-REFERENCE TO RELATED APPLICATIONS

This application is a 35 U.S.C. § 371 National Stage application of International Application PCT/EP2016/062514 (WO 2016/193380), filed Jun. 2, 2016, which claims priority to European Patent Applications 15170337.8, filed Jun. 2, 2015 and 15176207.7, filed Jul. 10, 2015; the contents of which are incorporated herein by reference.

In accordance with 37 C.F.R. § 1.52(e)(5), Applicants enclose herewith the Sequence Listing for the above-captioned application entitled "150002US01_SeqList.txt", created on Nov. 28, 2017. The Sequence Listing is made up of 114 kilobytes, and the information contained in the attached "SEQUENCE LISTING" is identical to the information in the specification as originally filed. No new matter is added.

TECHNICAL FIELD

The present invention relates to novel insulins or insulins analogues that are extended with sequences of predominantly polar amino acid residues in order to improve the half-life and stability of the drug substance. The invention also provides pharmaceutical compositions comprising such drug substances, and relates to the use of such drug substances for the treatment or prevention of metabolic disorders.

BACKGROUND ART

There is a pronounced desire to provide long-acting, stable and active insulins for the treatment of diabetes, and established methods for obtaining prolongation of action includes i.a. precipitated depots, acylation with fatty (di)acid derivatives for imposing albumin binding, and formation of soluble multihexamers. PEGylation (conjugation of proteins with high molecular weight polydisperse polyethyleneglycol) is also an established technology, but PEG, however, is not biodegradable, and PEG can in some cases accumulate in the body when used chronically. Moreover homogeneous polymers are preferred, but most long-chain polymers are only available in polydisperse form.

Biodegradable polymers with properties otherwise similar to PEG are thus of interest for protein drug engineering. The polymers should be polar in order to preserve aqueous solubility, and impose longer duration of therapeutic action in the body, for example by increasing hydrodynamic volume of the engineered proteins. The polymer must be covalently attached to the protein/insulin, which can be obtained as a chemical conjugate or by recombinant expression in a suitable host cell (as a fusion). The main in vivo prolonging effect of extended proteins may be ascribed to a prolonged absorption phase following subcutaneous administration due to large hydrodynamic volume.

Various solutions towards biodegradable polymers of increased half-lives have been suggested. Thus WO 2008 049931 describe certain peptide extended insulins showing a suitable in vivo half-life; DD 257197 describes a method for obtaining an immobilised active insulin product by the addition of poly-amino acids; DD 286509 describes a method for the preparation of an insulin preparation for rectal application, which preparation is activity stabilised and activity prolonging; Arakawa et al, Nature Biotechnology 1998, 16, 934-938, describe a plant-based cholera toxin B subunit-insulin fusion protein that protects against the development of autoimmune diabetes; WO 2008 019368 A2 describes certain albumin-insulin fusion proteins.

However, the insulins and insulins analogues according to this invention have never been described.

BRIEF SUMMARY OF THE INVENTION

While the polar recombinant extensions described in prior art, often suggesting the use of multiple Ser and Thr residues, may work well in bacterial-based production systems, such amino acid residues tends to get glycosylated in yeast-based expression systems, thereby decreasing the overall yield of proteins containing such extensions. Furthermore, as removal of glycosylated by-products during protein purification is difficult and resource consuming, the provision of alternative extensions solutions is desired out of consideration for an optimisation of yeast-based production processes.

Moreover it has been found that the oligomer extended products of the present invention, comprising the polar amino acids Gln and/or His, are less prone to give high viscosity when compared to other products, e.g. sequences holding multiple Glu (E).

Finally the oligomer extended insulins or insulin analogues of this invention render insulin profiles that have shown an in vivo duration and stability that may allow for a once-daily, or even once-weekly, administration.

Therefore, in its first aspect, the invention provides oligomer extended insulins or insulin analogues, which insulins or insulin analogues are extended at the N-terminal end of the B-chain, and/or from the C-terminal end of the A-chain with an extension consisting only of amino acid residues selected from the group of His (H), Gln (Q), Ala (A), Asp (D), Glu (E), Gly (G), Pro (P), Ser (S) and Thr (T); in which extension:

I) one or both of the amino acid residues selected from the group consisting of His (H) and Gln (Q); which number of amino acid residues of Group I is combined with II) no more than three times this number of the amino acid residues selected from the group consisting of Ala (A), Asp (D), Glu (E), Gly (G), Pro (P), Ser (S), and Thr (T); to render an oligomer extended insulin or insulin analogue, with an extension comprising of from about 100 to about 800 contiguous amino acid residues.

In another aspect the invention provides a pharmaceutical composition comprising the oligomer extended insulin or insulin analogue of the invention, together with one or more adjuvants, excipients, carriers and/or diluents.

In further aspects the invention relates to the use of the oligomer extended insulin or insulin analogue of the invention as a medicament, and to methods of treatment, prevention or alleviation of a metabolic disease or disorder or condition of a living animal body, including a human, which method comprises the step of administering to such a living animal body in need thereof, a therapeutically effective amount of the oligomer extended insulin or insulin analogue of the invention.

Other objects of the invention will be apparent to the person skilled in the art from the following detailed description and examples.

DETAILED DISCLOSURE OF THE INVENTION

Oligomer Extended Insulins or Insulin Analogues

In a 1$^{st}$ embodiment, the invention provides an oligomer extended insulin or insulin analogue, which insulin or insulin analogue is a two-chain insulin molecule comprising an A- and a B-chain, and which insulin or insulin analogue is extended at the N-terminal end of the B-chain, and/or from the C-terminal end of the A-chain, with an extension consisting only of amino acid residues selected from the group of His (H), Gln (Q), Ala (A), Asp (D), Glu (E), Gly (G), Pro (P), Ser (S) and Thr (T); in which extension:

I) one or both of the (two) amino acid residues selected from the group consisting of His (H) and Gln (Q) (i.e. Group I); which number (i.e. one or two) of amino acid residues of Group I is combined with II) no more than three times this number (i.e. three or six) of the amino acid residues selected from the group consisting of Ala (A), Asp (D), Glu (E), Gly (G), Pro (P), Ser (S), and Thr (T) (i.e. Group II);

to render an oligomer extended insulin or insulin analogue, with an extension comprising of from about 100 to about 800 contiguous amino acid residues.

This implies that the amino acids selected according to the invention may be repeated as needed in order to obtain an extension of the desired length and size.

In another embodiment, the invention provides an oligomer extended insulin or insulin analogue, which insulin or insulin analogue is a two-chain insulin molecule comprising an A- and a B-chain, and which insulin or insulin analogue is extended at the N-terminal end of the B-chain, and/or from the C-terminal end of the A-chain, with an extension consisting only of amino acid residues selected from the group of His (H), Gln (Q), Ala (A), Asp (D), Glu (E), Gly (G), Pro (P), Ser (S) and Thr (T); which extension is composed of:

I) one or both of the (two) amino acid residues selected from the group consisting of His (H) and Gln (Q) (i.e. Group I); which number (i.e. one or two) of amino acid residues of Group I is combined with II) no more than three times this number (i.e. three or six) of the amino acid residues selected from the group consisting of Ala (A), Asp (D), Glu (E), Gly (G), Pro (P), Ser (S), and Thr (T) (i.e. Group II);

to render a structural motif, wherein the numbers indicate the stoechiometric proportions of the amino acid residues stated above, and which composition may be repeated or extended to render an oligomer extended insulin or insulin analogue with an extension comprising of from about 100 to about 800 contiguous amino acid residues.

Polar residues are preferred mainly out of consideration for solubility and hydrodynamic size of the final product. Moreover Gln and His, that are both polar amino acids, are devoid of the glycosylation problems associated with Ser and Thr, in particular in relation to yeast expression systems. Finally, extensions with sequences involving a certain balance of Gln and/or His have shown to lower viscosity when compared to extensions with other sequences, e.g. sequences holding multiple Glu (E).

Therefore, in a third embodiment, the oligomer extension of the insulin or insulin analogue of the invention holds no more than one Glu (E) in its structural motif, as defined above.

In a fourth embodiment, the oligomer extended insulin or insulin analogue of the invention is a product wherein:

I) one of the (two) amino acid residues selected from the group consisting of His (H) and Gln (Q) (i.e. Group I); is combined with II) no more than three of the amino acid residues selected from the group consisting of Ala (A), Asp (D), Glu (E), Gly (G), Pro (P), Ser (S) and Thr (T) (i.e. Group II).

In a fifth embodiment, the oligomer extended insulin or insulin analogue of the invention is a product wherein:

I) one of the (two) amino acid residues selected from the group consisting of His (H) and Gln (Q) (i.e. Group I); is combined with II) no more than three of the amino acid residues selected from the group consisting of Ala (A), Glu (E), Gly (G), and Pro (P), (i.e. Group II).

In a sixth embodiment, the oligomer extended insulin or insulin analogue of the invention is a product wherein:

I) both of the (two) amino acid residues selected from the group consisting of His (H) and Gln (Q) (i.e. Group I); are combined with II) no more than six of the amino acid residues selected from the group consisting of Ala (A), Asp (D), Glu (E), Gly (G), Pro (P), Ser (S) and Thr (T) (i.e. Group II).

In a seventh embodiment, the oligomer extended insulin or insulin analogue of the invention is a product wherein:

I) both of the (two) amino acid residues selected from the group consisting of His (H) and Gln (Q) (i.e. Group I); are combined with II) no more than six of the amino acid residues selected from the group consisting of Ala (A), Glu (E), Gly (G), and Pro (P) (i.e. Group II).

In an eight embodiment, one or both of the amino acid residues of Group I are combined with the same number of amino acid residues selected from Group II.

In a ninth embodiment, one or both of the amino acid residues of Group I are combined with 1½ times the number of amino acid residues selected from Group II.

In a tenth embodiment, one or both of the amino acid residues of Group I are combined with 2 times the number of amino acid residues selected from Group II.

In an eleventh embodiment, one or both of the amino acid residues of Group I are combined with 2.5 times the number of amino acid residues selected from Group II.

In a twelfth embodiment, one or both of the amino acid residues of Group I are combined with 3 times the number of amino acid residues selected from Group II.

The extension carried out according to the present invention may be applied to an insulin molecule of any origin, and in particular of recombinant, bovine or porcine origin, or to any insulin analogue at hand.

In a further embodiment of the invention, the oligomer extended product according to the invention is oligomer extended human insulin.

In a $2^{nd}$ embodiment, the oligomer extended product of the invention is an oligomer extended insulin analogue selected from the group consisting of A14E, A21G, B16E, B25H, desB30 human insulin;
A14E, A21G, B16H, B25H, desB27, desB30 human insulin;
A14E, A21G, B16H, B25H, desB30 human insulin;
A14E, A21G, B25H, desB30 human insulin;
A14E, A21G, desB30 human insulin;
A14E, A21Q, B16E, B25H, desB30 human insulin;
A14E, A21Q, B16H, B25H, desB27, desB30 human insulin;
A14E, A21Q, B16H, B25H, desB30 human insulin;
A14E, A21G, B25H, desB27, desB30 human insulin;
A14E, A21Q, B25H, desB27, desB30 human insulin;
A14E, A21Q, B25H, desB30 human insulin;
A14E, A21Q, desB30 human insulin;
A14E, B16E, B25H, desB30 human insulin;
A14E, B16H, B25H, desB27, desB30 human insulin;
A14E, B16H, B25H, desB30 human insulin;
A14E, B25H, desB27, desB30 human insulin;

A14E, B25H, desB30 human insulin;
A21G, A22A, A23P, A24Q, desB30 human insulin;
A21G, A22A, A23Q, A24P, desB30 human insulin;
A21G, A22G human insulin;
A21G, A22K, B29R, desB30 human insulin;
A21G, A22P, A23A, A24Q, desB30 human insulin;
A21G, A22P, A23Q, A24A, desB30 human insulin;
A21G, A22Q, A23A, A24P, desB30 human insulin;
A21G, A22Q, A23P, A24A, desB30 human insulin;
A21G, A22Q, A23P, desB30 human insulin;
A21G, B1F, desB30 human insulin;
A21G, B3K, B29E human insulin;
A21G, desB27, desB30 human insulin;
A21G, B28D human insulin;
A21G, B28D, desB30 human insulin;
A21G, B28K, B29P human insulin;
A21G, desB30 human insulin;
A21Q, A22G human insulin;
A21Q, A22K, B29R, desB30 human insulin;
A21Q, B3K, B29E human insulin;
A21Q, desB27, desB30 human insulin;
A21Q, B28D human insulin;
A21Q, B28D, desB30 human insulin;
A21Q, B28K, B29P human insulin;
A21Q, desB30 human insulin;
A22K, B29R, desB30 human insulin;
B3K, B29E human insulin;
B28D human insulin;
B28D, desB30 human insulin;
B28K, B29P human insulin; or
desB30 human insulin.

In one embodiment, the insulin analogue is selected from the group consisting of
A14E, A21G, B25H, desB30 human insulin;
A21G, A22A, A23P, A24Q, desB30 human insulin;
A21G, A22A, A23Q, A24P, desB30 human insulin;
A21G, A22P, A23A, A24Q, desB30 human insulin;
A21G, A22P, A23Q, A24A, desB30 human insulin;
A21G, A22Q, A23A, A24P, desB30 human insulin;
A21G, A22Q, A23P, A24A, desB30 human insulin;
A21G, A22Q, A23P, desB30 human insulin;
A21G, B1F, desB30 human insulin;
A21G, desB30 human insulin; and
A21Q, desB30 human insulin.

In another embodiment, the insulin analogue is selected from the group consisting of
A14E, A21G, B25H, desB30 human insulin;
A21G, desB30 human insulin; and
A21Q, desB30 human insulin.

In a third embodiment, the insulin analogue is A14E, A21G, B25H, desB30 human insulin.

In a fourth embodiment, the insulin analogue is A21G, A22A, A23P, A24Q, desB30 human insulin.

In a fifth embodiment, the insulin analogue is A21G, A22A, A23Q, A24P, desB30 human insulin.

In a sixth embodiment, the insulin analogue is A21G, A22P, A23A, A24Q, desB30 human insulin.

In a seventh embodiment, the insulin analogue is A21G, A22P, A23Q, A24A, desB30 human insulin.

In an eight embodiment, the insulin analogue is A21G, A22Q, A23A, A24P, desB30 human insulin.

In a ninth embodiment, the insulin analogue is A21G, A22Q, A23P, A24A, desB30 human insulin.

In a tenth embodiment, the insulin analogue is A21G, A22Q, A23P, desB30 human insulin.

In an eleventh embodiment, the insulin analogue is A21G, B1F, desB30 human insulin.

In a twelfth embodiment, the insulin analogue is A21G, desB30 human insulin.

In a thirteenth embodiment, the insulin analogue is A21Q, desB30 human insulin.

If the extension begins with a Gly (G) residue, then the insulin analogue selected according to the invention may preferably be an A21Gly (G) containing analogue, or an A21Gln (Q) containing analogue.

Therefore, in one embodiment, the oligomer extended product of the invention is an oligomer extended insulin analogue comprising the A21Gly (G) or A21Gln (Q) mutation, and the extension begins with a Gly (G) residue.

Also, in yet another embodiment, if the insulin analogue holds the native A21N position, then the first amino acid of the N-terminal end of the oligomer extention should not be a Gly (G) residue.

In a $3^{rd}$ embodiment, the oligomer extended insulin or insulin analogue of the invention is extended at the N-terminal end of the B-chain.

In a $4^{th}$ embodiment, the oligomer extended insulin or insulin analogue of the invention is extended at the C-terminal end of the A-chain.

In a $5^{th}$ embodiment, the oligomer extended insulin or insulin analogue of the invention is extended at the N-terminal end of the B-chain and from the C-terminal end of the A-chain.

In a $6^{th}$ embodiment, the oligomer extended insulin or insulin analogue of the invention is extended with
A) contiguous amino acid residues comprising amino acid residues selected from the group of [A, G, and H or Q]; or from the group of [E, G, and H or Q]; or from the group of [G, P, and H or Q]; (i.e. Group A); or
B) contiguous amino acid residues comprising amino acid residues selected from the group of [A, G, P, and H or Q]; or from the group of [E, G, P, and H or Q]; or from the group of [G, K, P, and H or Q]; or from the group of [E, G, H, and Q]; (i.e. Group B); or
C) contiguous amino acid residues comprising amino acid residues selected from the group of [A, G, P, H, and Q]; or from the group of [E, G, P, H, and Q]; (i.e. Group C); or
D) contiguous amino acid residues comprising amino acid residues selected from the group of [A, E, G, P, H, and Q]; (i.e. Group D];
and/or any combination of Groups A, B, C, and D.

In a $7^{th}$ embodiment, the oligomer extended insulin or insulin analogue of the invention is extended with non-repeating sequences, i.e. sequences of random order.

In one embodiment, the oligomer extended insulin or insulin analogue of the invention is extended with a sequence of amino acid residues comprising A, D, E, G, H, P, Q, S, and T, in random order.

In another embodiment, the oligomer extended insulin or insulin analogue of the invention is extended with a sequence of amino acid residues comprising A, D, E, G, H, P, and Q, in random order.

In a third embodiment, the oligomer extended insulin or insulin analogue of the invention is extended with a sequence of amino acid residues comprising A, E, G, H, P, Q, S, and T, in random order.

In a fourth embodiment, the oligomer extended insulin or insulin analogue of the invention is extended with a sequence of amino acid residues comprising A, E, G, H, P, and Q, in approximately equal amounts, but in random order.

In an $8^{th}$ embodiment, the oligomer extended insulin or insulin analogue of the invention is extended with repeats of certain motifs, such motifs may be repeated as needed in order to obtain an extension of the desired length and size.

Depending on the motif in question, the number of repeats may be within the range of from about 2 to about 400.

In one embodiment, the number of repeats is within the range of from about 5 to about 250.

In another embodiment, the number of repeats is within the range of from about to about 200.

In a third embodiment, the number of repeats is 10, 12, 13, 15, 20, 25, 30, 31, 33, 37, 40, 44, 49, 50, 56, 60, 62, 65, 66, 67, 69, 70, 75, 80, 90, 100, 125, or 150.

In a 9$^{th}$ embodiment, the amino acid residues of Group A are represented by contiguous amino acid residues selected from the group of [A, G, and H or Q] (i.e. Group A1).

In one embodiment, the amino acid residues of Group A1 are selected from the group of [A, G, and H].

In another embodiment, the amino acid residues of Group A1, selected from the group of [A, G, and H], are represented by one or more of the following motifs: [GHA]; [HAG]; [AGH]; [GAH]; [AHG]; and [HGA]; and any combination hereof.

In a third embodiment, the amino acid residues of Group A1 are selected from the group of [A, G, and Q].

In a fourth embodiment, the amino acid residues of Group A1, selected from the group of [A, G, and Q], are represented by one or more of the following motifs: [GQA]; [QAG]; [AGQ]; [GAQ]; [AQG]; and [QGA]; and any combination hereof.

In a fifth embodiment, the amino acid residues of Group A1, selected from the group of [A, G, and Q], are represented by one or both of the following motifs: [GQA]; and [GAQ]; and any combination hereof.

In a sixth embodiment, the amino acid residues of Group A1, selected from the group of [A, G, and Q], are represented by the motif: [GAQ]; in any combination.

In a 10$^{th}$ embodiment, the amino acid residues of Group A are represented by contiguous amino acid residues selected from the group of [E, G, and H or Q] (i.e. Group A2).

In one embodiment, the amino acid residues of Group A2 are selected from the group of [E, G, and H].

In another embodiment, the amino acid residues of Group A2, selected from the group of [E, G, and H], are represented by one or more of the following motifs: [GEH]; [EHG]; [HGE]; [GHE]; [HEG]; and [EGH]; and any combination hereof.

In a third embodiment, the amino acid residues of Group A2, selected from the group of [E, G, and H], are represented by one or both of the following motifs: [GEH]; and [GHE]; and any combination hereof.

In a fourth embodiment, the amino acid residues of Group A2, selected from the group of [E, G, and H], are represented by the motif: [GEH], in any combination.

In a fifth embodiment, the amino acid residues of Group A2 are selected from the group of [E, G, and Q].

In a sixth embodiment, the amino acid residues of Group A2, selected from the group of [E, G, and Q], are represented by one or more of the following motifs: [GEQ]; [EQG]; [QGE]; [GQE]; [QEG]; and [EGQ]; and any combination hereof.

In a seventh embodiment, the amino acid residues of Group A2, selected from the group of [E, G, and Q], are represented by one or both of the following motifs: [GEQ]; and [GQE]; and any combination hereof.

In an 11$^{th}$ embodiment, the amino acid residues of Group A are represented by contiguous amino acid residues selected from the group of [G, P, and H or Q] (i.e. Group A3).

In one embodiment, the amino acid residues of Group A3 are selected from the group of [G, P, and H].

In another embodiment, the amino acid residues of Group A3, selected from the group of [G, P, and H], are represented by one or more of the following motifs: [GHPH]; [HPHG]; [PHGH]; and [HGHP]; and any combination hereof.

In a third embodiment, the amino acid residues of Group A3, selected from the group of [G, P, and H], are represented by of the motif: [GHPH].

In a fourth embodiment, the amino acid residues of Group A3 are selected from the group of [G, P, and Q].

In a fifth embodiment, the amino acid residues of Group A3, selected from the group of [G, P, and Q], are represented by one or more of the following motifs: [GQP]; [QPG]; and [PGQ]; and any combination hereof.

In a sixth embodiment, the amino acid residues of Group A3, selected from the group of [G, P, and Q], are represented by one or more of the following motifs: [GQPQ]; [QPQG]; [PQGQ]; and [QGQP]; and any combination hereof.

In a seventh embodiment, the amino acid residues of Group A are selected from one or more of the following motifs: [GAQ]; [GEH]; [GEQ]; [GQA]; [GQE]; and/or [GQP]; and any combination hereof.

In a 12$^{th}$ embodiment, the amino acid residues of Group B are represented by contiguous amino acid residues selected from the group of [A, G, P, and H or Q] (i.e. Group B1).

In one embodiment, the amino acid residues of Group B1 are selected from the group of [A,G,P,H].

In another embodiment, the amino acid residues of Group B1, selected from the group of [A,G,P,H], are represented by one or more of the following motifs: [GAPH]; [APHG]; [PHGA]; [HGAP]; [GAHP]; [AHPG]; [HPGA]; [PGAH]; [GPAH]; [PAHG]; [AHGP]; [HGPA]; [GHAP]; [HAPG]; [APGH]; [PGHA]; [GHPA]; [HPAG]; [PAGH]; [AGHP]; [PHAG]; [HAGP]; [AGPH]; and [GPHA]; and any combination hereof.

In a third embodiment, the amino acid residues of Group B1, selected from the group of [A,G,P,H], are represented by the following motif: [GAPH].

In a fourth embodiment, the amino acid residues of Group B1 are selected from the group of [A,G,P,Q].

In a fifth embodiment, the amino acid residues of Group B1, selected from the group of [A,G,P,Q], are represented by one or more of the following motifs: [GAPQ]; [APQG]; [PQGA]; [QGAP]; [GAQP]; [AQPG]; [QPGA]; [PGAQ]; [GPAQ]; [PAQG]; [AQGP]; [QGPA]; [GQAP]; [QAPG]; [APGQ]; [PGQA]; [GQPA]; [QPAG]; [PAGQ]; [AGQP]; [PQAG]; [QAGP]; [AGPQ]; and [GPQA]; and any combination hereof.

In a sixth embodiment, the amino acid residues of Group B1, selected from the group of [A,G,P,Q], are represented by one or more of the following motifs: [GAPQ]; [GAQP]; [GPAQ]; [GQAP]; [GQPA]; [PQAG]; and [GPQA]; and any combination hereof.

In a 13$^{th}$ embodiment, the amino acid residues of Group B are represented by contiguous amino acid residues selected from the group of [E, G, P, and H or Q] (i.e. Group B2).

In one embodiment, the amino acid residues of Group B2 are selected from the group of [E,G,P,H].

In another embodiment, the amino acid residues of Group B2, selected from the group of [E,G,P,H], are represented by one or more of the following motifs: [GEHP]; [EHPG]; [HPGE]; [PGEH]; [GEPH]; [EPHG]; [PHGE]; [HGEP]; [GHPE]; [HPEG]; [PEGH]; [EGHP]; [GHEP]; [HEPG]; [EPGH]; [PGHE]; [GHHP]; [HHPG]; [HPGH]; [PGHH];

[GPEH]; [PEHG]; [EHGP]; [HGPE]; [GPHE]; [PHEG]; [HEGP]; and [EGPH]; and any combination hereof.

In a third embodiment, the amino acid residues of Group B2, selected from the group of [E,G,P,H], are represented by one or more of the following motifs: [GEHP]; [GEPH]; [GHPE]; [GHEP]; [GHHP]; [GPEH]; and [GPHE]; and any combination hereof.

In a fourth embodiment, the amino acid residues of Group B2 are selected from the group of [E,G,P,Q].

In a fifth embodiment, the amino acid residues of Group B2, selected from the group of [E,G,P,Q], are represented by one or more of the following motifs: [GEQP]; [EQPG]; [QPGE]; [PGEQ]; [GEPQ]; [EPQG]; [PQGE]; [QGEP]; [GQPE]; [QPEG]; [PEGQ]; [EGQP]; [GQEP]; [QEPG]; [EPGQ]; [PGQE]; [GQQP]; [QQPG]; [QPGQ]; [PGQQ]; [GPEQ]; [PEQG]; [EQGP]; [QGPE]; [GPQE]; [PQEG]; [QEGP]; and [EGPQ]; and any combination hereof.

In a sixth embodiment, the amino acid residues of Group B2, selected from the group of [E,G,P,Q], are represented by one or more of the following motifs: [GEQP]; [GEPQ]; [GQPE]; [GQEP]; [GPEQ]; and [GPQE]; and any combination hereof.

In a 14$^{th}$ embodiment, the amino acid residues of Group B are represented by contiguous amino acid residues selected from the group of [E, G, H, and Q] (i.e. Group B4).

In one embodiment, the amino acid residues of Group B4 are selected from the group of [E,G,H,Q].

In another embodiment, the amino acid residues of Group B4, selected from the group of [E,G,H,Q], are represented by one or more of the following motifs: [GEQH]; [EQHG]; [QHGE]; [HGEQ]; [GEHQ]; [EHQG]; [HQGE]; [QGEH]; [GHEQ]; [HEQG]; [EQGH]; [QGHE]; [GHQE]; [HQEG]; [QEGH]; [EGHQ]; [GQHP]; [QHPG]; [HPGQ]; [PGQH]; [GQEH]; [QEHG]; [EHGQ]; [HGQE]; [GQHE]; [QHEG]; [HEGQ]; [EGQH]; [GHQP]; [HQPG]; [QPGH]; and [PGHQ]; and any combination hereof.

In a third embodiment, the amino acid residues of Group B4, selected from the group of [E,G,H,Q], are represented by one or more of the following motifs: [GEQH]; [GEHQ]; [GHEQ]; [GHQE]; [GQHP]; [GQEH]; and [GQHE]; and any combination hereof.

In a fourth embodiment, the amino acid residues of Group B are selected from one or more of the following motifs: [GAPH]; [GAPQ]; [GAQP]; [GPAQ]; [GQAP]; [GQPA]; [PQAG]; [GPQA]; [GEHP]; [GEPH]; [GHPE]; [GHEP]; [GHHP]; [GPEH]; [GPHE]; [GEQP]; [GEPQ]; [GQPE]; [GQEP]; [GPEQ]; [GPQE]; [GEQH]; [GEHQ]; [GHEQ]; [GHQE]; [GQHP]; [GQEH]; and/or [GQHE]; and any combination hereof.

In a 15$^{th}$ embodiment, the amino acid residues of Group C are represented by contiguous amino acid residues selected from the group of [A, G, P, H, and Q] (i.e. Group C1).

In one embodiment, the amino acid residues of Group C1, selected from the group of [A, G, P, H, and Q], are represented by one or more of the following motifs: [GHAPGHHP]; [HAPGHHPG]; [APGHHPGH]; [PGHHPGHA]; [GHHPGHAP]; [HHPGHAPG]; [HPGHAPGH]; [PGHAPGHH]; [GHAPGQHP]; [HAPGQHPG]; [APGQHPGH]; [PGQHPGHA]; [GQHPGHAP]; [QHPGHAPG]; [HPGHAPGQ]; [PGHAPGQH]; [GQAPGQHP]; [QAPGQHPG]; [APGQHPGQ]; [PGQHPGQA]; [GQHPGQAP]; [QHPGQAPG]; [HPGQAPGQ]; and [PGQAPGQH]; and any combination hereof.

In another embodiment, the amino acid residues of Group C1, selected from the group of [A, G, P, H, and Q], are represented by one or more of the following motifs:
[GQAPGQAPGAPHGAPH]; [HGQAPGQAP-GAPHGAP]; [PHGQAPGQAPGAPHGA]; [APHGQAPGQAPGAPHG]; [GAPHGQAPGQAPGAPH]; [HGAPHGQAPGQAPGAP]; [PHGAPHGQAPGQAPGA]; [APHGAPHGQAPGQAPG]; [GAPHGAPHGQAPGQAP]; [PGAPHGAPHGQAPGQA]; [APGAPHGAPHGQAPGQ]; [QAPGAPHGAPHGQAPG]; [GQAPGAPHGAPHGQAP]; [PGQAPGAPHGAPHGQA]; [APGQAPGAPHGAPHGQ]; [GQAPGAPHGAPHGAPH]; [QAPGAPHGAPHGAPHG]; [APGAPHGAPHGAPHGQ]; [PGAPHGAPHGAPHGQA]; [GAPHGAPHGAPHGQAP]; [APHGAPHGAPHGQAPG]; [PHGAPHGAPHGQAPGA]; [HGAPHGAPHGQAPGAP]; [GAPHGAPHGQAPGAPH]; [APHGAPHGQAPGAPHG]; [PHGAPHGQAPGAPHGA]; [HGAPHGQAPGAPHGAP]; [GAPHGQAPGAPHGAPH]; [APHGQAPGAPHGAPHG]; [PHGQAPGAPHGAPHGA]; [HGQAPGAPHGAPHGAP]; and [QAPGQAPGAPHGAPHG]; and any combination hereof.

In a third embodiment, the amino acid residues of Group C1, selected from the group of [A, G, P, H, and Q], are represented by one or more of the following motifs:
[GQAPGQAPGQAPGAPH]; [HGQAPGQAPGQAP-GAP]; [PH GQAPGQAPGQAPGA]; [APHGQAPGQAPGQAPG]; [GAPHGQAPGQAPGQAP]; [PGAPHGQAPGQAPGQA]; [APGAPHGQAPGQAPGQ]; [QAPGAPHGQAPGQAPG]; [GQAPGAPHGQAPGQAP]; [PGQAPGAPHGQAPGQA]; [APGQAPGAPHGQAPGQ]; [QAPGQAPGAPHGQAPG]; [PGQAPGQAPGAPHGQA]; [APGQAPGQAPGAPHGQ]; and [QAPGQAPGQAPGAPHG]; and any combination hereof.

In a 16$^{th}$ embodiment, the amino acid residues of Group C are represented by contiguous amino acid residues selected from the group of [E, G, P, H, and Q] (i.e. Group C2).

In one embodiment, the amino acid residues of Group C2, selected from the group of [E, G, P, H, and Q], are represented by one or more of the following motifs: [GHEPGHHP]; [HEPGHHPG]; [EPGHHPGH]; [PGHHPGHE]; [GHHPGHEP]; [HHPGHEPG]; [HPGHEPGH]; [PGHEPGHH]; [GHEPGQHP]; [HEPGQHPG]; [EPGQHPGH]; [PGQHPGHE]; [GQHPGHEP]; [QHPGHEPG]; [HPGHEPGQ]; [PGHEPGQH]; [GQEPGQHP]; [QEPGQHPG]; [EPGQHPGQ]; [PGQHPGQE]; [GQHPGQEP]; [QHPGQEPG]; [HPGQEPGQ]; and [PGQEPGQH]; and any combination hereof.

In another embodiment, the amino acid residues of Group C, selected from the group of [E, G, P, H, and Q], are represented by one or more of the following motifs: [GHEPGHHP]; [GHEPGQHP]; and [GQEPGQHP]; and any combination hereof.

In a third embodiment, the amino acid residues of Group C are selected from one or more of the following motifs: [GHEPGHHP]; [GHEPGQHP]; [GQEPGQHP]; [GQAP-GAPHGAPHGAPH]; [GQAPGQAPGAPHGAPH]; and/or [GQAPGQAPGQAPGAPH]; and any combination hereof.

In a 17$^{th}$ embodiment, the amino acid residues of Group D are represented by contiguous amino acid residues selected from the group of [A, E, G, P, H, and Q], (i.e. Group D1); or from the group of [A, E, G, H, P, Q] (in random order) (i.e. Group D2).

In one embodiment, the amino acid residues of Group D1, selected from the group of [A, E, G, P, H, and Q], are represented by one or more of the following motifs: [GEHP- GAPHGQEPGQAP]; [EH PGAPHGQEPGQAPG]; [HPGAPHGQEPGQAPGE]; [PGAPHGQEPGQAPGEH]; [GAPHGQEPGQAPGEHP]; [APHGQEPGQAPGEHPG]; [PHGQEPGQAPGEHPGA]; [HGQEPGQAPGEHPGAP]; [GQEPGQAPGEHPGAPH]; [QEPGQAPGEHPGAPHG]; [EPGQAPGEHPGAPHGQ]; [PGQAPGEHPGAPHGQE]; [GQAPGEHPGAPHGQEP]; [QAPGEHPGAPHGQEPG]; [APGEHPGAPHGQEPGQ]; [PGEHPGAPHGQEPGQA]; [GQAPGQAPGAPHGAPH]; [QAPGQAPGAPHGAPHG]; [APGQAPGAPHGAPHGQ]; [PGQAPGAPHGAPHGQA]; [GQAPGAPHGAPHGQAP]; [QAPGAPHGAPHGQAPG]; [APGAPHGAPHGQAPGQ]; [PGAPHGAPHGQAPGQA]; [GAPHGAPHGQAPGQAP]; [APHGAPHGQAPGQAPG]; [PHGAPHGQAPGQAPGA]; [HGAPHGQAPGQAPGAP]; [GAPHGQAPGQAPGAPH]; [APHGQAPGQAPGAPHG]; [PHGQAPGQAPGAPHGA]; [HGQAPGQAPGAPHGAP]; [GQAPGQAPGAPGAPH]; [QAPGQAPGQAPGAPHG]; [APGQAPGQAPGAPHGQ]; [PGQAPGQAPGAPHGQA]; [GQAPGQAPGAPHGQAP]; [QAPGQAPGAPHGQAPG]; [APGQAPGAPHGQAPGQ]; [PGQAPGAPHGQAPGQA]; [GQAPGAPHGQAPGQAP]; [QAPGAPHGQAPGQAPG]; [APGAPHGQAPGQAPGQ]; [PGAPHGQAPGQAPGQA]; [GAPHGQAPGQAPGQAP]; [APHGQAPGQAPGQAPG]; [PH GQAPGQAPGQAPGA]; [HGQAPGQAPGQAP-GAP]; [GQEPGAPHGAPHGAPH]; [QEP-GAPHGAPHGAPHG]; [EPGAPHGAPHGAPHGQ]; [PGAPHGAPHGAPHGQE]; [GAPHGAPHGAPHGQEP]; [APHGAPHGAPHGQEPG]; [PHGAPHGAPHGQEPGA]; [HGAPHGAPHGQEPGAP]; [GAPHGAPHGQEPGAPH]; [APHGAPHGQEPGAPHG]; [PHGAPHGQEPGAPHGA]; [HGAPHGQEPGAPHGAP]; [GAPHGQEPGAPHGAPH]; [APHGQEPGAPHGAPHG]; [PHGQEPGAPHGAPHGA]; [HGQEPGAPHGAPHGAP]; [GQEPGQEPGAPHGAPH]; [QEPGQEPGAPHGAPHG]; [EPGQEPGAPHGAPHGQ]; [PGQEPGAPHGAPHGQE]; [GQEPGAPHGAPHGQEP]; [QEPGAPHGAPHGQEPG]; [EPGAPHGAPHGQEPGQ]; [PGAPHGAPHGQEPGQE]; [GAPHGAPHGQEPGQEP]; [APHGAPHGQEPGQEPG]; [PHGAPHGQEPGQEPGA]; [HGAPHGQEPGQEPGAP]; [GAPHGQEPGQEPGAPH]; [APHGQEPGQEPGAPHG]; [PHGQEPGQEPGAPHGA]; [HGQEPGQEPGAPHGAP]; [GQEPGQEPGAPHGAPH]; [QEPGQEPGQEPGAPHG]; [EPGQEPGQEPGAPHGQ]; [PGQEPGQEPGAPHGQE]; [GQEPGQEPGAPHGQEP]; [QEPGQEPGAPHGQEPG]; [EPGQEPGAPHGQEPGQ]; [PGQEPGAPHGQEPGQE]; [GQEPGAPHGQEPGQEP]; [QEPGAPHGQEPGQEPG]; [EPGAPHGQEPGQEPGQ]; [PGAPHGQEPGQEPGQE]; [GAPHGQEPGQEPGQEP]; [APHGQEPGQEPGQEPG]; [PHGQEPGQEPGQEPGA]; and [HGQEPGQEPGQEPGAP]; and any combination hereof.

In another embodiment, the amino acid residues of Group D1, selected from the group of [A, E, G, P, H, and Q], are represented by one or more of the following motifs: [GEHP-GAPHGQEPGQAP]; [GQAPGAPHGAPHGAPH]; [GQAPGQAPGAPHGAPH]; [GQAPGQAPGQAPGAPH]; [GQEPGAPHGAPHGAPH]; [GQEPGQEPGAPHGAPH]; and [GQEPGQEPGQEPGAPH]; and any combination hereof.

In another embodiment, the amino acid residues of Group D are selected from one or more of the following motifs: [GEHPGAPHGQEPGQAP]; [GQEPGAPHGAPHGAPH]; [GQEPGQEPGAPHGAPH]; and [GQEPGQEPGQEPGAPH]; and any combination hereof.

In an 18$^{th}$ embodiment, the oligomer extended insulin or insulin analogue of the invention is extended with a motif of Group A selected from [GEH]; [GQA]; [GQE]; [GHE]; [GEQ]; [GAQ]; and [GQP]; and/or any combination hereof; and/or a motif of Group B selected from [GAPH]; [GAPQ]; [GEHP]; [GEPH]; [GEQH]; [GHEP]; [GHHP]; [PQAG]; [GQAP]; [GQEP]; [GQHP]; [GQPE]; [GEQP]; [GEPQ]; [GPEQ]; [GPQE]; [GQPA]; [GAQP]; [GPAQ]; [GPQA]; [GHPE]; [GPEH]; [GPHE]; [GQEH]; [GQHE]; [GEHQ]; [GHEQ]; and [GHQE]; and/or any combination hereof; and/or a motif of Group C selected from [GHEP-GHHP]; [GHEP-GQHP]; and [GQEP-GQHP]; and/or any combination hereof; and/or a motif of Group D selected from [GEHP-GAPH-GQEP-GQAP]; [GQAP-GAPH-GAPH-GAPH]; [GQAP-GQAP-GAPH-GAPH]; [GQAP-GQAP-GQAP-GAPH]; [GQEP-GAPH-GAPH-GAPH]; [GQEP-GQEP-GAPH-GAPH]; and [GQEP-GQEP-GQEP-GAPH]; and/or any combination hereof; and/or any combination of motifs of Groups A, B, C and D;

which motif may be repeated as needed in order to obtain an extension of the desired length and size.

In a 19$^{th}$ embodiment, the oligomer extended insulin or insulin analogue of the invention is extended with a motif of Group A selected from [GAQ]; [GEH]; [GEQ]; [GQA]; [GQE]; and [GQP]; and/or any combination hereof; and/or a motif of Group B selected from [GAPH]; [GAPQ]; [GAQP]; [GEHP]; [GEPH]; [GEPQ]; [GEQH]; [GEQP]; [GHEP]; [GHEQ]; [GHPE]; [GHQE]; [GPAQ]; [GPEH]; [GPEQ]; [GPHE]; [GPQA]; [GPQE]; [GQAP]; [GQEH]; [GQEP]; [GQHE]; [GQPA]; and[GQPE]; and/or any combination hereof; and/or a motif of Group C selected from [GHEPGQHP]; [GQEPGQHP]; [GQAPGQAPGQAPGAPH]; and [GQAPGQAPGAPHGAPH]; and/or any combination hereof; and/or a motif of Group D selected from [GEHP-GAPHGQEPGQAP]; [GQEPGQEPGQEPGAPH]; [GQEPGQEPGAPHGAPH]; and [A,E,G,P,H,Q]; and/or any combination hereof.

The insulin or insulin analogue may be extended with one or more amino acid residues identified above, and the repeat in question does not have to begin with Gly (G).

The insulin or insulin analogue may be extended with one or more amino acid residues identified above, and the repeat in question can start with any amino acid from the repeat (for example the extended insulin analogue with GAPH repeat can start with APH, PH or H, followed by repeats of GAPH).

In a 20$^{th}$ embodiment, the oligomer extended insulin or insulin analogue of the invention comprises from about 100 to about 800 contiguous amino acid residues in its extension.

In one embodiment, the oligomer extended insulin or insulin analogue of the invention comprises at least about 100 contiguous amino acid residues.

In another embodiment, the oligomer extended insulin or insulin analogue of the invention comprises less than about 800 contiguous amino acid residues.

In a third embodiment, the oligomer extended insulin or insulin analogue of the invention comprises of from about 100 to about 700 contiguous amino acid residues.

In a fourth embodiment, the oligomer extended insulin or insulin analogue of the invention comprises of from about 100 to about 600 contiguous amino acid residues.

In a fifth embodiment, the oligomer extended insulin or insulin analogue of the invention comprises of from about 100 to about 500 contiguous amino acid residues.

In a sixth embodiment, the oligomer extended insulin or insulin analogue of the invention comprises of from about 100 to about 400 contiguous amino acid residues.

In a seventh embodiment, the oligomer extended insulin or insulin analogue of the invention comprises of from about 100 to about 300 contiguous amino acid residues.

In an eight embodiment, the oligomer extended insulin or insulin analogue of the invention comprises of from about 150 to about 300 contiguous amino acid residues.

In a ninth embodiment, the oligomer extended insulin or insulin analogue of the invention comprises of from about 150 to about 250 contiguous amino acid residues.

In a tenth embodiment, the oligomer extended insulin or insulin analogue of the invention comprises of from about 175 to about 225 contiguous amino acid residues.

In an eleventh embodiment, the oligomer extended insulin or insulin analogue of the invention comprises of from about 185 to about 215 contiguous amino acid residues.

In a twelfth embodiment, the oligomer extended insulin or insulin analogue of the invention comprises of from about 190 to about 210 contiguous amino acid residues; and in particular 124, 148, 176, 196, 198, 200, 201, 208, 224, 248, 276, 300, 400, 500, or 600 contiguous amino acid residues.

In a thirteenth embodiment, the oligomer extended insulin or insulin analogue of the invention comprises of from about 190 to about 210 contiguous amino acid residues; and in particular 200, 201, 208 contiguous amino acid residues.

In a 21$^{th}$ embodiment, the oligomer extended insulin or insulin analogue of the invention is a compound of the general Formula I $$\text{Ins-Ext} \tag{I}$$

wherein:

"Ins" represents an analogue of human insulin as identified in Table 1 below; and "Ext" indicates an extension as described in Table 1 below.

TABLE 1

| Ex. No. | Insulin analogue | Extension*** (repeat) | No.** |
|---|---|---|---|
| 1 | A21Q*, desB30 | GQEP | 200 |
| 2 | A21Q*, desB30 | GAPQ | 200 |
| 3 | A21Q*, desB30 | GQAP | 200 |
| 4 | A21Q*, desB30 | GEPH | 200 |
| 5 | A21Q*, desB30 | GEHP | 200 |
| 6 | A14E, A21G*, B25H, desB30 | GQEP | 200 |
| 7 | A14E, A21G*, B25H, desB30 | GAPQ | 200 |
| 9 | A14E, A21G*, B25H, desB30 | GEPH | 200 |
| 10 | A14E, A21G*, B25H, desB30 | GEHP | 200 |
| 11 | A14E, A21G*, B25H, desB30 | GAPH | 200 |
| 12 | A21G*, desB30 | GEHPGAPHGQEPGQAP | 208 |
| 13 | A21G*, desB30 | GEH | 201 |
| 14 | A21G*, desB30 | GQA | 201 |
| 15 | A21G*, desB30 | GQE | 201 |
| 16 | A21G*, desB30 | GEQH | 200 |
| 17 | A21G*, desB30 | GQEPGQEPGQEPGAPH | 200 |
| 18 | A21G*, desB30 | GQEPGQEPGAPHGAPH | 200 |
| 20 | A21G*, desB30 | GQAPGQAPGQAPGAPH | 200 |
| 21 | A21G*, desB30 | GQAPGQAPGAPHGAPH | 200 |
| 23 | A21G*, desB30 | [A, E, G, H, P, Q] (in random) | 200 |
| 24 | A21G*, desB30 | GHEPGQHP | 200 |
| 25 | A21G*, desB30 | GQEPGQHP | 200 |
| 32 | A21G*, desB30 | GQPE | 200 |
| 33 | A21G*, desB30 | GEQP | 200 |
| 34 | A21G*, desB30 | GEPQ | 200 |
| 35 | A21G*, desB30 | GPEQ | 200 |
| 36 | A21G*, desB30 | GPQE | 200 |
| 37 | A21G*, desB30 | GQPA | 200 |
| 38 | A21G*, desB30 | GAQP | 200 |
| 39 | A21G*, desB30 | GPAQ | 200 |
| 40 | A21G*, desB30 | GPQA | 200 |
| 41 | A21G*, desB30 | GHEP | 200 |
| 42 | A21G*, desB30 | GHPE | 200 |
| 43 | A21G*, desB30 | GPEH | 200 |
| 44 | A21G*, desB30 | GPHE | 200 |
| 45 | A21G*, desB30 | GQEH | 200 |
| 46 | A21G*, desB30 | GQHE | 200 |
| 48 | A21G*, desB30 | GHEQ | 200 |
| 49 | A21G*, desB30 | GHQE | 200 |
| 51 | A21G*, desB30 | GEQ | 201 |
| 52 | A21G*, desB30 | GAQ | 201 |
| 53 | A21G*, desB30 | GQAP | 248 |
| 54 | A21G*, desB30 | GQAP | 300 |
| 55 | A21G*, desB30 | GQAP | 400 |
| 56 | A21G*, desB30 | GQAP | 200 |
| 57 | A21G*, desB30 | GQAP | 500 |
| 58 | A21G*, desB30 | GQAP | 600 |
| 59 | A14E, A21G*, B25H, desB30 | GQAP | 200 |
| 60 | A14E, A21G*, B25H, desB30 | GQAP | 300 |
| 61 | A14E, A21G*, B25H, desB30 | GQAP | 600 |
| 62 | A21G, B1F*, desB30 | GQAP | 200 |
| 63 | A21G, B1F*, desB30 | GQAP | 400 |
| 64 | A21G, A22A, A23P, A24Q*, desB30 | GAPQ | 196 |
| 65 | A21G, A22A, A23Q, A24P*, desB30 | GAQP | 196 |

TABLE 1-continued

| Ex. No. | Insulin analogue | Extension*** (repeat) | No.** |
|---|---|---|---|
| 66 | A21G, A22Q, A23A, A24P*, desB30 | GQAP | 196 |
| 67 | A21G, A22Q, A23P, A24A*, desB30 | GQPA | 196 |
| 68 | A21G, A22P, A23A, A24Q*, desB30 | GPAQ | 196 |
| 69 | A21G, A22P, A23Q, A24A*, desB30 | GPQA | 196 |
| 70 | A21G*, desB30 | GQAP | 224 |
| 71 | A21G*, desB30 | GQAP | 276 |
| 72 | A21G*, desB30 | GQAP | 124 |
| 73 | A21G*, desB30 | GQAP | 148 |
| 74 | A21G*, desB30 | GQAP | 176 |
| 75 | A21G, A22Q, A23P*, desB30 | GQP | 198 |
| 76 | A21G, A22A, A23Q, A24P*, desB30 | GAQP | 148 |
| 77 | A21G, A22A, A23Q, A24P*, desB30 | GAQP | 248 |

*indicates point of extension
**indicates number of amino acid residues in the extension
***in the specified order (unless otherwise stated)

In a 22$^{nd}$ embodiment, the oligomer extended insulin or insulin analogue of the invention is a compound selected from A21Q(GQEP)$_{50}$, desB30 human insulin;
A21Q(GAPQ)$_{50}$, desB30 human insulin;
A21Q(GQAP)$_{50}$, desB30 human insulin;
A21Q(GEPH)$_{50}$, desB30 human insulin;
A21Q(GEHP)$_{50}$, desB30 human insulin;
A14E, A21G(GQEP)$_{50}$, B25H, desB30 human insulin;
A14E, A21G(GAPQ)$_{50}$, B25H, desB30 human insulin;
A14E, A21G(GEPH)$_{50}$, B25H, desB30 human insulin;
A14E, A21G(GEHP)$_{50}$, B25H, desB30 human insulin;
A14E, A21G(GAPH)$_{50}$, B25H, desB30 human insulin;
A21G(GEHPGAPHGQEPGQAP)$_{13}$, desB30 human insulin;
A21G(GEH)$_{67}$, desB30 human insulin;
A21G(GQA)$_{67}$, desB30 human insulin;
A21G(GQE)$_{67}$, desB30 human insulin;
A21G(GEQH)$_{50}$, desB30 human insulin;
A21G(GQEPGQEPGQEPGAPH)$_{12}$GQEPGQEP, desB30 human insulin;
A21G(GQEPGQEPGAPHGAPH)$_{12}$GQEPGQEP, desB30 human insulin;
A21G(GQAPGQAPGQAPGAPH)$_{12}$GQAPGQAP, desB30 human insulin;
A21G(GQAPGQAPGAPHGAPH)$_{12}$GQAPGQAP, desB30 human insulin;
A21G[A,E,G,H,P,Q] (random 200 amino acids), desB30 human insulin;
A21G(GHEPGQHP)$_{25}$, desB30 human insulin;
A21G(GQEPGQHP)$_{25}$, desB30 human insulin;
A21G(GQPE)$_{50}$, desB30 human insulin;
A21G(GEQP)$_{50}$, desB30 human insulin;
A21G(GEPQ)$_{50}$, desB30 human insulin;
A21G(GPEQ)$_{50}$, desB30 human insulin;
A21G(GPQE)$_{50}$, desB30 human insulin;
A21G(GQPA)$_{50}$, desB30 human insulin;
A21G(GAQP)$_{50}$, desB30 human insulin;
A21G(GPAQ)$_{50}$, desB30 human insulin;
A21G(GPQA)$_{50}$, desB30 human insulin;
A21G(GHEP)$_{50}$, desB30 human insulin;
A21G(GHPE)$_{50}$, desB30 human insulin;
A21G(GPEH)$_{50}$, desB30 human insulin;
A21G(GPHE)$_{50}$, desB30 human insulin;
A21G(GQEH)$_{50}$, desB30 human insulin;
A21G(GQHE)$_{50}$, desB30 human insulin;
A21G(GHEQ)$_{50}$, desB30 human insulin;
A21G(GHQE)$_{50}$, desB30 human insulin;
A21G(GEQ)$_{67}$, desB30 human insulin;
A21G(GAQ)$_{67}$, desB30 human insulin;
A21G(GQAP)$_{62}$, desB30 human insulin;
A21G(GQAP)$_{75}$, desB30 human insulin;
A21G(GQAP)$_{100}$, desB30 human insulin;
A21G(GQAP)$_{50}$, desB30 human insulin;
A21G(GQAP)$_{125}$, desB30 human insulin;
A21G(GQAP)$_{150}$, desB30 human insulin;
A14E, A21G(GQAP)$_{50}$, B25H, desB30 human insulin;
A14E, A21G(GQAP)$_{75}$, B25H, desB30 human insulin;
A14E, A21G(GQAP)$_{150}$, B25H, desB30 human insulin;
A21G, B1F(GQAP)$_{50}$, desB30 human insulin;
A21G, B1F(GQAP)$_{100}$, desB30 human insulin;
A21G, A22A, A23P, A24Q(GAPQ)$_{49}$, desB30 human insulin;
A21G, A22A, A23Q, A24P(GAQP)$_{49}$, desB30 human insulin;
A21G, A22Q, A23A, A24P(GQAP)$_{49}$, desB30 human insulin;
A21G, A22Q, A23P, A24A(GQPA)$_{49}$, desB30 human insulin;
A21G, A22P, A23A, A24Q(GPAQ)$_{49}$, desB30 human insulin;
A21G, A22P, A23Q, A24A(GPQA)$_{49}$, desB30 human insulin;
A21G(GQAP)$_{56}$, desB30 human insulin;
A21G(GQAP)$_{69}$, desB30 human insulin;
A21G(GQAP)$_{31}$, desB30 human insulin;
A21G(GQAP)$_{37}$, desB30 human insulin;
A21G(GQAP)$_{44}$, desB30 human insulin;
A21G, A22Q, A23P(GQP)$_{66}$, desB30 human insulin;
A21G, A22A, A23Q, A24P(GAQP)$_{37}$, desB30 human insulin; and
A21G, A22A, A23Q, A24P(GAQP)$_{62}$, desB30 human insulin.

Any combination of two or more of the embodiments described herein is considered within the scope of the present invention.

Nomenclature of Oligomer Extended Insulin Analogues

In the context of this invention, the oligomer extended insulin analogues are named relative to human insulin by specification of amino acid deletions, substitutions, insertions and extensions, as also specified by the general Formula I, above.

In this way the compound of e.g. Example 2 represents an analogue of human insulin (A21Q*, desB30), wherein the naturally occurring amino acid residue located in position 21 of the A-chain has been substituted for glutamine (Q), and wherein the naturally occurring amino acid residue located in position B30 has been deleted, and which analogue has been extended in the star-marked position (*) with an extension made up of repeats of the four amino acid residues (GAPQ in the specified order) to make an extension consisting of a total of 200 amino acids residues (which may also be designated as $(GAPQ)_{50}$).

This analogue may also be designated A21Q(GAPQ)$_{50}$, desB30 human insulin, and the compound is illustrated in FIG. 8.

Methods of Production

The oligomer extended insulin or insulin analogue of the invention may be obtained by conventional methods for the preparation of insulin, insulin analogues and insulin derivatives, and in particular the methods described in the working examples.

In brief, insulin-coding DNA is fused with DNA coding for the recombinant extensions. The DNA is transfected into yeast and the extended insulin is expressed and harvested. The extended insulin is expressed as single-chain precursor protein, which precursor protein is subsequently cleaved to obtain a mature, two-chain (A- and B-chain), extended insulin.

Biological Activity

In another aspect the invention provides novel oligomer extended insulin or insulin analogue for use as medicaments, or for use in the manufacture of medicaments or pharmaceutical compositions.

In a further aspect, the invention relates to the medical use of the oligomer extended insulin or insulin analogue of the invention, and in particular to the use of such products for the treatment, prevention or alleviation of diseases, disorders or conditions relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers, which method comprises administration to a subject in need thereof a therapeutically effective amount of the insulin derivative of the invention.

In another embodiment, the invention relates to the use of such products for the treatment, prevention or alleviation of diseases, disorders or conditions relating to diabetes, Type 1 diabetes, Type 2 diabetes, or impaired glucose tolerance, which method comprises administration to a subject in need thereof a therapeutically effective amount of the insulin derivative of the invention.

In a third embodiment, the invention relates to the use of such products for the treatment, prevention or alleviation of diseases, disorders or conditions relating to diabetes, and in particular Type 1 diabetes or Type 2 diabetes.

Pharmaceutical Compositions

The present invention relates to oligomer extended insulins or insulin analogues useful as medicaments, or for the manufacture of a pharmaceutical composition/medicament, and in particular for use in the treatment, prevention or alleviation of a metabolic disease or disorder or condition.

Therefore, in another aspect, the invention provides novel pharmaceutical compositions comprising a therapeutically effective amount of an oligomer extended insulin or insulin analogue according to the present invention, optionally together with one or more adjuvants, excipients, carriers and/or diluents.

Injectable compositions may be prepared by using conventional techniques, which typically includes dissolving and mixing the ingredients as appropriate to give the desired end product, addition of isotonic agents, preservatives and/or buffers as required, and adjusting the pH value of the solution, e.g. using an acid, for example, hydrochloric acid, or a base, for example, aqueous sodium hydroxide, as needed. Finally, the volume of the solution may be adjusted with water to give the desired concentration of the ingredients.

In one embodiment a solution or suspension is made by dissolving an oligomer extended insulin or insulin analogue of the invention in an aqueous medium at slightly acidic conditions, for example, in a concentration in the range from about 240 to about 2400 μmol/L. The aqueous medium is made isotonic, e.g. using sodium chloride or glycerol. Moreover, the aqueous medium may contain buffers such as acetate or citrate, preservatives such as m-cresol or phenol and zinc ions, e.g. 2 to 5 $Zn^{++}$ per 6 insulins, or in a concentration of up to about 20 μg of $Zn^{++}$ per unit of insulin activity. The pH value of the solution may be adjusted towards neutral, without getting too close to the isoelectric point of the compound in question, in order to avoid potential precipitation. The pH value of the final insulin preparation depends upon the concentration of zinc ions, and the concentration of the compound of this invention. The insulin preparation is made sterile, e.g. by sterile filtration.

Methods of Therapy

The present invention relates to drugs for therapeutic use. More specifically the invention relates to the use of the oligomer extended insulin or insulin analogue of the invention for the treatment or prevention of medical conditions relating to diabetes.

Therefore, in another aspect, the invention provides a method for the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers, which method comprises the step of administering to a subject in need thereof a therapeutically effective amount of the oligomer extended insulin or insulin analogue of the invention.

In another embodiment the invention provides a method for the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, metabolic syndrome (metabolic syndrome X, insulin resistance syndrome), hypertension, cognitive disorders, atherosclerosis, myocardial infarction, stroke, cardiovascular disorders, coronary heart disease, inflammatory bowel syndrome, dyspepsia, or gastric ulcers, which method comprises administration to a subject in need thereof a therapeutically effective amount of the oligomer extended insulin or insulin analogue of the invention.

In a third embodiment the invention provides a method for the treatment or alleviation of a disease or disorder or condition of a living animal body, including a human, which disease, disorder or condition may be selected from a disease, disorder or condition relating to diabetes, Type 1 diabetes, Type 2 diabetes, impaired glucose tolerance, hyperglycemia, dyslipidemia, obesity, or metabolic syndrome (metabolic syndrome X, insulin resistance syndrome).

In a fourth embodiment the invention provides a method for the treatment or alleviation of a disease or disorder or condition of a living animal body, including a human, which disease, disorder or condition may be selected from a disease, disorder or condition relating to diabetes, in particular Type 1 diabetes, or Type 2 diabetes.

BRIEF DESCRIPTION OF THE DRAWINGS

An exemplary embodiment of the present invention is further illustrated by reference to the accompanying drawing, in which:

FIG. 7 shows the amino acid sequence of the extension of the compound of Example 23 (A21G[A,E,G,H,P,Q] (200 amino acid residues in random order), desB30 human insulin);

FIG. 8 shows the structure (sequence) of the compound of Example 2; and

FIG. 9 shows the structure (sequence) of the precursor for the compound of Example 2.

EXAMPLES

Figure 1:
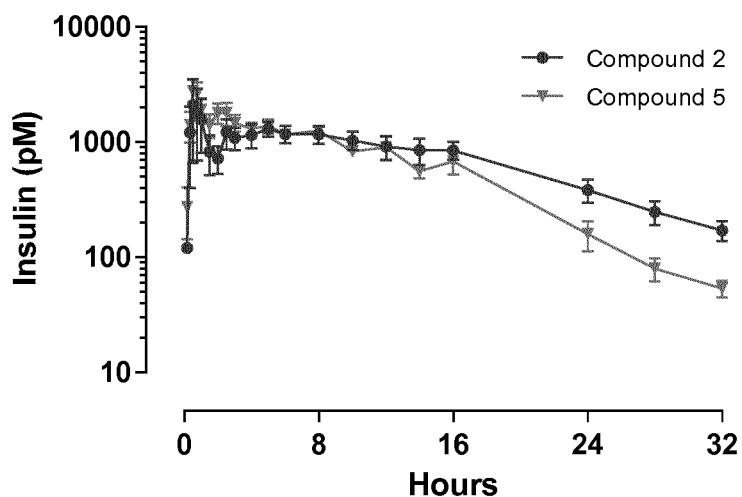
FIG. 1 shows plasma insulin concentration (pM) curves following administration (s.c.) of the compounds of Examples 2 and 5, respectively.

The invention is further illustrated with reference to the following examples, which are not intended to be in any way limiting to the scope of the invention as claimed.

Examples 1-52

Methods of Expression and Purification
Expression

The insulin analogue for use according to the invention are produced recombinantly by expressing a DNA sequence encoding the insulin analogue in question in a suitable host cell by well-known techniques, e.g. as disclosed in U.S. Pat. No. 6,500,645. The insulin analogue is either expressed directly or as a precursor molecule, which may have an additional N-terminal extension (in the form of e.g. EEAE-AEAPK) on the B-chain and/or a connecting peptide (C-peptide, in the form of e.g. DMK) between the B-chain and the A-chain. This N-terminal extension and C-peptide are cleaved off in vitro by a suitable protease, e.g. *Achromobactor lyticus* protease (ALP) or trypsin, and therefore will have a cleavage site next to position B1, B29 and A1, respectively. N-terminal extensions and C-peptides of the type suitable for use according to this invention are disclosed in e.g. U.S. Pat. No. 5,395,922, EP 765395, WO 9828429 and WO 2014/195452.

The polynucleotide sequence encoding the insulin analogue precursor for use according to the invention are prepared synthetically by established methods, e.g. the phosphoramidite method described by Beaucage et al. (1981) *Tetrahedron Letters* 22 1859-1869, or the method described by Matthes et al. (1984) *EMBO Journal* 3 801-805. According to the phosphoramidite method, oligonucleotides are synthesised in e.g. an automatic DNA synthesiser, purified, duplexed, and ligated to form the synthetic DNA construct. A currently preferred way of preparing the DNA construct is by polymerase chain reaction (PCR).

The recombinant method will typically make use of a vector capable of replicating in the selected microorganism or host cell, and which carries a polynucleotide sequence encoding the insulin analogue precursor for use according to the present invention. The recombinant vector may be an autonomously replicating vector, i.e., a vector which exists as an extra-chromosomal entity, the replication of which is independent of chromosomal replication, e.g. a plasmid, an extra-chromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid, or two or more vectors or plasmids, which together contain the total DNA to be introduced into the genome of the host cell, or a transposon, may be used. The vector may be a linear or a closed circular plasmid, and will preferably contain an element(s) that permits stable integration of the vector into the host cell's genome or autonomous replication of the vector in the cell independent of the genome.

The recombinant expression vector may be one capable of replicating in yeast. Examples of sequences, which enable the vector to replicate in yeast, are the yeast plasmid 2 μm replication genes REP 1-3 and origin of replication.

The vector may contain one or more selectable markers, which permit easy selection of trans-formed cells. A selectable marker is a gene the product that provides for biocide or viral resistance, resistance to heavy metals, prototrophy to auxotrophs, etc. Examples of bacterial selectable markers are the dal genes from *Bacillus subtilis* or *Bacillus licheniformis*, or markers which confer antibiotic resistance, such as ampicillin, kanamycin, chloramphenicol or tetracycline resistance. Selectable markers for use in a filamentous fungal host cell include amdS (acetamidase), argB (ornithine carbamoyltransferase), pyrG (orotidine-5'-phosphate decarboxylase) and trpC (anthranilate syn-thase). Suitable markers for yeast host cells are ADE2, HIS3, LEU2, LYS2, MET3, TRP1, and URA3. A well suited selectable marker for yeast is the *Schizosaccharomyces pompe* TPI gene (Russell (1985) Gene 40 125-130).

Within the vector, the polynucleotide sequence is operably connected to a suitable promoter sequence. The promoter may be any nucleic acid sequence that shows transcriptional activity in the host cell of choice, including mutant, truncated, and hybrid promoters, and may be obtained from genes encoding extra-cellular or intra-cellular polypeptides either homologous or heterologous to the host cell.

In a yeast host, examples of useful promoters are the *Saccharomyces cerevisiae* Ma1, TPI, ADH, TDH3 or PGK promoters.

The polynucleotide sequence encoding the insulin peptide backbone for use according to the invention also will typically be operably connected to a suitable terminator. In yeast, a suitable terminator is the TPI terminator (Alber et al. (1982) *J. Mol. Appl. Genet.* 1 419-434).

The procedures used to combine the polynucleotide sequence encoding the insulin analogue for use according to the invention, the promoter and the terminator, respectively, and to insert them into a suitable vector containing the information necessary for replication in the selected host, are well known to persons skilled in the art. It will be understood that the vector may be constructed either by first preparing a DNA construct containing the entire DNA sequence encoding the insulin backbones for use according to the invention, and subsequently inserting this fragment into a suitable expression vector, or by sequentially inserting DNA fragments containing genetic information for the individual elements (such as the signal and pro-peptide (N-terminal extension of the B-chain), C-peptide, A- and B-chains), followed by ligation.

The vector comprising the polynucleotide sequence encoding the insulin analogue for use according to the invention is introduced into a host cell, so that the vector is maintained as a chromosomal integrant, or as a self-replicating extra-chromosomal vector. The term "host cell" encompasses any progeny of a parent cell that is not identical to the parent cell due to mutations that occur during replication.

The host cell may in particular be a yeast cell. The yeast organism may be any suitable yeast organism which, on cultivation, secretes the insulin peptide backbone or the precursor hereof into the culture medium. Examples of suitable yeast organisms are include strains selected from *Saccharomyces cerevisiae, Saccharomyces kluyveri, Schizosaccharomyces pombe, Sacchoromyces uvarum, Kluyveromyces lactis, Hansenula polymorpha, Pichia pastoris, Pichia methanolica, Pichia kluyveri, Yarrowia lipolytica, Candida* sp., *Candida utilis, Candida cacaoi, Geotrichum* sp., and *Geotrichum fermentans*.

The transformation of the yeast cells may for instance be effected by protoplast formation followed by transformation by known methods. The medium used to cultivate the cells may be any conventional medium suitable for growing yeast organisms.

Purification

The secreted insulin analogue or precursor hereof are recovered from the medium by conventional procedures including separating the yeast cells from the medium by centrifugation, by filtration or by catching or adsorbing the insulin analogue or precursor hereof on an ion exchange matrix or on a reverse phase absorption matrix, precipitating the proteinaceous components of the supernatant, or by filtration by means of a salt, e.g. ammonium sulphate, followed by purification by a variety of chromatographic procedures, e.g. ion exchange chromatography, affinity chromatography, etc.

The purification and digestion of the insulin peptide backbones of this invention is carried out as follows:

The single-chain insulin analogue precursor, which may contain an N-terminal extension of the B-chain, and a modified C-peptide between the B-chain and the A-chain, is purified and concentrated from the yeast culture supernatant by cation exchange (Kjeldsen et al. (1998) *Prot. Expr. Pur.* 14 309-316).

The single-chain insulin analogue precursor is matured into two-chain insulin peptide backbone by digestion with lysine-specific immobilised *Achromobactor lyticus* protease (ALP) (Kristensen et al. (1997) *J. Biol. Chem.* 20 12978-12983) or by use of trypsin to cleave off the N-terminal extension of the B-chain, if present, and the C-peptide.

Trypsin Digestion

The eluate from the cation exchange chromatography step containing the insulin analogue precursor is diluted with water to an ethanol concentration of 15-20%. Glycine is added to a concentration of 50 mM and pH is adjusted to 9.0-9.5 by NaOH. Trypsin is added in a proportion of 1:300 (w:w) and digestion is allowed to proceed at 4 degrees. The digestion is analytically monitored every 20 minutes until digestion is completed. The digestion is terminated with addition of 1 M citric acid in a proportion of 3:100 (v:v). The exact amount of trypsin may need to be adjusted for some analogues.

The digestion reaction is analysed by analytical liquid chromatography (LC) on a Waters Acquity Ultra-Performance Liquid Chromatography system using a C18 column and the molecular weight is confirmed by MALDI-TOF mass spectrometry (MS) (Bruker Daltonics Autoflex II TOF/TOF or UltrafleXtreme).

The two-chain insulin analogue is purified by reversed phase HPLC (Waters 600 system) on a C18 column using an acetonitrile gradient. The desired insulin analogue is subsequently recovered by lyophilisation.

Purity of the product may be determined by analytical HPLC, e.g. on a Waters Acquity Ultra-Performance Liquid Chromatography system using a C18 column, and the molecular weight may be confirmed by MALDI-TOF MS or LC-MS (Orbitrap, Thermo Scientific or G2S Synapt, Waters A/S).

ALP Digestion

The single-chain insulin precursor is matured into two-chain insulin by digestion with lysine-specific immobilized *Achromobachter lyticus* protease (ALP; Kristensen et al., (1997), J. Biol. Chem. 20, 12978-12983).

The eluate from the cation exchange chromatography step containing the insulin precursor is diluted with water to an ethanol concentration of 15-20%. Sodium glutamate is added to a concentration of 15 mM and pH is adjusted to 9.7 by NaOH. Immobilized ALP is added in a proportion of 1:100 (v:v), and digestion is allowed to proceed with mild stirring in room temperature overnight.

The digestion reaction is analysed by analytical LC on a Waters Acquity Ultra-Performance Liquid Chromatography system using a C4 column and the molecular weight is confirmed by matrix-assisted laser desorption ionization time-of-flight mass spectrometry (Bruker Daltonics Autoflex II TOF/TOF). The immobilized ALP is removed by filtration with a 0.2 μm filter.

The two-chain insulin molecule is purified by reversed phase HPLC (Waters 600 system) on a C18 column using an acetonitrile gradient. The desired insulin or insulin analogue is recovered by lyophilisation.

Purity is determined by analytical LC on a Waters Acquity Ultra-Performance Liquid Chromatography system using a C4 column, and the molecular weight is confirmed by matrix-assisted laser desorption ionization time-of-flight mass spectrometry.

LC-MS Determination

The identity of the analogue precursors were verified in the supernatants by mass spectrometry using analytical HPLC on a Waters Acquity Ultra-Performance Liquid Chromatography system, couplet to a mass spectrometer (Synapt G2, Waters A/S). The average mass was calculated using the MaxEnt1 deconvolution algorithm in MassLynx (Waters A/S).

Parameters used for the HPLC analyses were as follows: Column: Waters ACQUITY UPLC® BEH300 C4 1.7 μm, Column temp: 40° C., Solvent: A: 0.1% FA, B: 0.1% FA in MeCN.

The results of this determination are presented in Table 3 below.

TABLE 2

| Gradient | | | | |
|---|---|---|---|---|
| Ex. No. | Time (min) | Flow Rate | % A | % B |
| 1 | Initial | 0.100 | 90.0 | 10.0 |
| 2 | 1:00 | 0.100 | 90.0 | 10.0 |
| 3 | 31:00 | 0.100 | 60.0 | 40.0 |
| 4 | 31:50 | 0.100 | 5.0 | 95.0 |
| 5 | 32:00 | 0.100 | 5.0 | 95.0 |
| 6 | 32:50 | 0.100 | 90.0 | 10.0 |
| 7 | 80:00 | 0.010 | 50.0 | 50.0 |

Determination of Insulin Receptor Affinities

The relative binding affinity of the insulin analogues of the invention for the human insulin receptor (IR) is determined by competition binding in a scintillation proximity assay (SPA) (according to Glendorf T et al. (2008) *Biochemistry* 47 4743-4751).

In brief, dilution series of a human insulin standard and the insulin analogue to be tested are performed in 96-well Optiplates (Perkin-Elmer Life Sciences) followed by the addition of [$^{125}$I-A14Y]-human insulin, anti-IR mouse antibody 83-7, solubilised human IR-A (semi-purified by wheat germ agglutinin chromatography from baby hamster kidney (BHK) cells overexpressing the IR-A holoreceptor), and scintillation proximity assay (SPA) beads (Anti-Mouse polyvinyltoluene SPA Beads, GE Healthcare) in binding buffer consisting of 100 mM HEPES (pH 7.8), 100 mM NaCl, 10 mM MgSO$_4$, and 0.025% (v/v) Tween 20. Plates are incubated with gentle shaking for 22-24 h at 22° C., centrifuged at 2000 rpm for 2 minutes and counted on a TopCount NXT (Perkin-Elmer Life Sciences).

Data from the SPA are analysed according to the four-parameter logistic model (Vølund A (1978) *Biometrics* 34 357-365), and the binding affinities of the analogues calculated relative to that of the human insulin standard measured within the same plate.

The results of this determination are presented in Table 3 below.

This example demonstrates that the compounds representative of the invention indeed target the human insulin receptor.

Metabolic Potency Determination

To investigate the analogues ability to generate a response in vitro selected analogues where tested for their metabolic potency, rFFC, were determined by lipogenesis according to known techniques (Moody A. J. et al. (1974) Metab. Res. 6 12-16 and Rodbell M (1964) J. Biol. Chem. 239 375-365).

Primary rat adipocytes are isolated from the epididymale fat pads and incubated with 3H-glucose in buffer containing 1% fat free HSA and either standard (HI) or ligand. The labelled glucose is converted into extractable lipids in a dose dependent way, resulting in full dose response curves for both ligands. The data were analysed according to a four-parameter logistic model and the affinities were expressed relative to a human insulin standard. The result is expressed as relative potency of ligand compared to standard.

TABLE 3

| Insulin Receptor Affinities & Mass LC-MS Data | | | | |
|---|---|---|---|---|
| Ex. No. | Receptor binding (hIRA) SPA, sup % relative to HI | rFFC % relative to HI | Calculated Precursor Mass (Da) | Measured Mass (Da) |
| 1 | 8.54 | 8.0 | 27602.8 | 27602.4 |
| 2 | 7.52 | 7.1 | 24700.9 | 24700.6 |
| 3 | 6.55 | 4.9 | 24700.9 | 24700.6 |
| 4 | 5.09 | 7.0 | 28053.3 | 28053.3 |
| 5 | 5.41 | 6.5 | 28053.3 | 28053.4 |
| 6 | 3 | 3.3 | 27487.2 | 27486.6 |
| 7 | 3.13 | 3.8 | 24585.7 | 24584.8 |
| 9 | 3.3 | 2.9 | 27938.1 | 27938 |
| 10 | 3.1 | 3.0 | 27938.1 | 27938 |
| 12 | 6.97 | 4.4 | 27079.8 | 27079.2 |
| 13 | 4.85 | 8.6 | 28622.6 | 28622.6 |
| 14 | 4.11 | — | 24130.4 | 24129.5 |
| 15 | 6.6 | 5.2 | 28018.9 | 28018.1 |
| 16 | 7.77 | 7.4 | 29532.3 | 29532.8 |
| 17 | 4.51 | 7.2 | 26943.4 | 26942.3 |
| 18 | 4.53 | 8.0 | 26355.0 | 26354.6 |
| 20 | 4.17 | 5.9 | 24737.6 | 24737.1 |
| 21 | 7.59 | — | 24845.8 | 24845.2 |
| 23 | 2.84 | — | 26551.1 | 26550.6 |
| 25 | 4.06 | 5.2 | 27732.3 | 27732.1 |
| 32 | 4.09 | — | 27531.7 | 27531.5 |
| 33 | 9.04 | — | 27531.7 | 27531.5 |
| 34 | 8.24 | — | 27531.7 | 27531.5 |
| 35 | 8.18 | — | 27531.7 | 27531.5 |
| 36 | 6.53 | — | 27531.7 | 27531.5 |
| 37 | 4.26 | 8.5 | 24629.8 | 24629.6 |
| 38 | 4.66 | 6.6 | 24629.8 | 24629.8 |
| 39 | 6.5 | 8.2 | 24629.8 | 24629.8 |
| 40 | 5.05 | 9.4 | 24629.8 | 24629.8 |
| 41 | 4.67 | — | 27982.2 | 27981.9 |
| 42 | 3.47 | — | 27982.2 | 27982 |
| 43 | 10.08 | — | 27982.2 | 27981.9 |
| 44 | 7.85 | — | 27982.2 | 27981.4 |
| 45 | 5.99 | — | 29532.9 | 29532.7 |
| 46 | 7.83 | — | 29532.9 | 29532.6 |
| 48 | 6.7 | — | 29532.9 | 29532.6 |
| 49 | 9.41 | — | 29532.9 | 29533.1 |
| 51 | 8.48 | — | 28018.9 | 28018.1 |
| 52 | 6.99 | — | 24130.4 | 24129.5 |
| 53 | 4.45 | — | 28870.4 | 28869.6 |
| 54 | 4.19 | — | 33464.3 | 33464 |
| 55 | 3.19 | — | 42298.7 | 42298.6 |
| 56 | 4.56 | — | 24629.8 | 24629.2 |
| 57 | 2.65 | — | 51133.2 | 51132.9 |
| 58 | 2.87 | — | 59967.6 | 59967 |
| 59 | 3.15 | — | 24585.7 | 24584.9 |
| 60 | 2.41 | — | 33420.2 | 33419.8 |
| 61 | 2.1 | — | 59923.6 | 59923.4 |
| 62 | 8.38 | — | 24629.8 | 24629.1 |

TABLE 3-continued

Insulin Receptor Affinities & Mass LC-MS Data

| Ex. No. | Receptor binding (hIRA) SPA, sup % relative to HI | rFFC % relative to HI | Calculated Precursor Mass (Da) | Measured Mass (Da) |
|---|---|---|---|---|
| 63 | 4.98 | — | 42298.7 | 42297.4 |
| 64 | 9.98 | — | 24572.8 | 24572.4 |
| 65 | 4.38 | — | 24572.8 | 24572.1 |
| 66 | 4.92 | — | 24572.8 | 24571.6 |
| 67 | 5.53 | — | 24572.8 | 24572.4 |
| 68 | 5.7 | — | 24572.8 | 24572.3 |
| 69 | 5.26 | — | 24572.8 | 24572.1 |
| 70 | 3.49 | — | 26750.1 | 26749.7 |
| 71 | 4.2 | — | 30990.6 | 30636.9 |
| 72 | 4.55 | — | 22509.6 | 22509.5 |
| 73 | 5.33 | — | 20035.9 | 20035.3 |
| 74 | 6.34 | — | 17904.4 | 17904.4 |
| 75 | 0.08 | — | 25817.9 | 25816.9 |
| 76 | 5.71 | — | 20332.2 | 20331.6 |
| 77 | 3.89 | — | 29166.7 | 29166.6 |

Determination of the Size in Native Size Exclusion Chromatography

The effect of different amino acid repeats on the large hydrodynamic volume was evaluated by native size exclusion chromatography. The solvent used was: 140 mM NaCl, 10 mM Tris-HCl, 5% (v/v) isopropanol, pH 7.3; and the column: Waters Acquity UPLC BEH450 SEC, 4.6×150 mm, 2.5 uM.

The method was run at 37° C. with a flow of 0.3 ml/min and measured at a wavelength of 280 nm. Selected analogues were analysed in 200 uM solutions. For conversion of the elution retention time to a corresponding mass for a protein, here called SEC size, a standard for size calculation was used: BEH450 SEC protein Standard Mix (P/N18600842).

A non-linear fit ($Y=Y0*exp(k*X)$) is made in GraphPad prism using the retention time and sizes of the individual proteins in the standard. The constants Y0 and k is found, and the SEC size (Y) is calculated by inserting the retention time (X) of the main peak in the equation.

TABLE 4

SEC size

| Ex. No. | SEC size (kDa) | Calculated Mass (kDa) | SEC size/mass |
|---|---|---|---|
| 1 | 275 | 26.3 | 10 |
| 2 | 165 | 23.3 | 7 |
| 3 | 125 | 23.3 | 5 |
| 4 | 275 | 26.7 | 10 |
| 37 | 170 | 23.3 | 7 |
| 38 | 140 | 23.3 | 6 |
| 39 | 145 | 23.3 | 6 |
| 40 | 135 | 23.3 | 6 |

Human insulin is found as equilibrium between monomer and dimer in this system so this could also be the case for these constructs. The SEC size is more than 5-10 times larger than the expected monomer size. The SEC size is influenced by the amino acid composition and also order of amino acids in the motif.

Example 53

Determination of Mean Residence Times and Effect on Blood Glucose

Dog Mean Residence Times

The pharmacokinetic and pharmacodynamic profiles after single s.c. dosing of 4 nmol/kg insulin analogue to Beagle dogs were investigated.

Eight Beagle dogs were divided in two groups of four animals and dosed in parallel with either the compound of Example 2 or the compound of Example 5.

A single subcutaneous dose of both analogues were well tolerated in Beagle dogs with no clinical signs of hypoglycaemia.

Figure 2:
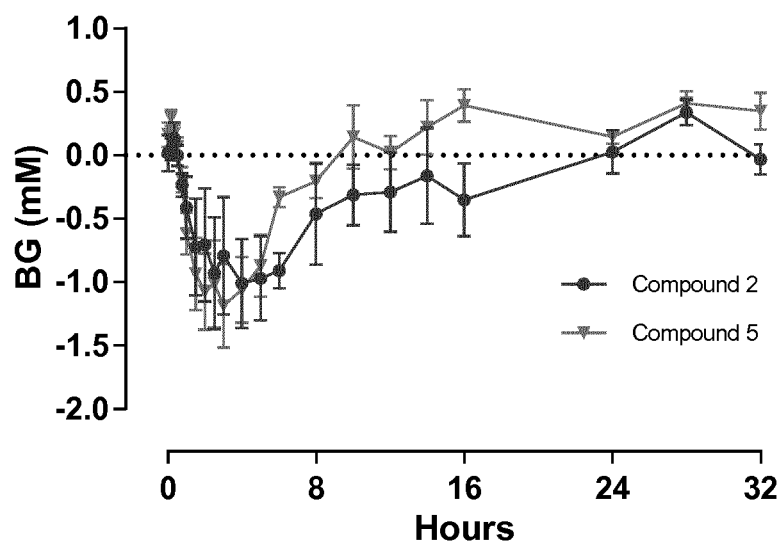
FIG. 2 shows plasma glucose concentration (mM) curves following administration (s.c.) of the compounds of Examples 2 and 5, respectively.

Blood samples were collected and analysed by the LOCI technology. Plasma insulin concentration curves are shown in FIGS. 1-2. Calculated mean residence time (mean±SD) is shown in Table 5 below.

Rat Mean Residence Times

The pharmacokinetic profiles after single s.c. dosing of 20 nmol/kg insulin analogue to male Sprague-Dawley rats were investigated.

Non-fasted rats were dosed s.c. in the neck with 20 nmol/kg insulin by the use of needle and syringe with a dose volume of 1 ml/kg. Rats were awake during the experiment with free access to water but not food during the first 8 hour after dosing. Blood samples for insulin analysis were collected regularly for 48 hours after dosing while blood glucose was measured until 8 hours after dosing. Blood samples were analysed by the LOCI technology. Calculated mean residence times (mean±SD) are shown in Table 5 below.

This example demonstrates that the compounds representative of the invention not only target human insulin receptor, but also are capable of effectively lowering the blood glucose, as shown in FIGS. 1-2.

TABLE 5

Mean Residence Time

| Ex. No. | $MRT_{sc}$ (h) Dog | $MRT_{sc}$ (h) Rat |
|---|---|---|
| 1 | 8.1 ± 1.3 | 5.5 ± 0.4 |
| 2 | 13.4 ± 3.0 | 5.4 ± 0.7 |
| 3 | 11.2 ± 2.2 | 3.8 ± 0.8 |
| 4 | 11.0 ± 4.0 | 5.3 ± 0.3 |
| 5 | 9.2 ± 2.2 | 5.3 ± 0.7 |
| 6 | — | 7.1 ± 0.1 |
| 7 | — | 6.0 ± 0.4 |
| 9 | — | 5.8 ± 1 |
| 15 | — | 8.7 ± 3.2 |
| 16 | — | 4.9 ± 1.2 |
| 17 | — | 5.9 ± 1.3 |
| 18 | — | 4.8 ± 0.3 |
| 20 | — | 5.7 ± 0.5 |
| 25 | — | 5.4 ± 0.5 |
| 37 | — | 5.2 ± 0.6 |
| 38 | — | 3.8 ± 0.5 |
| 39 | — | 4.3 ± 1.2 |
| 40 | — | 3.6 ± 0.9 |

Example 54

Determination of Glycosylation

Figure 3:
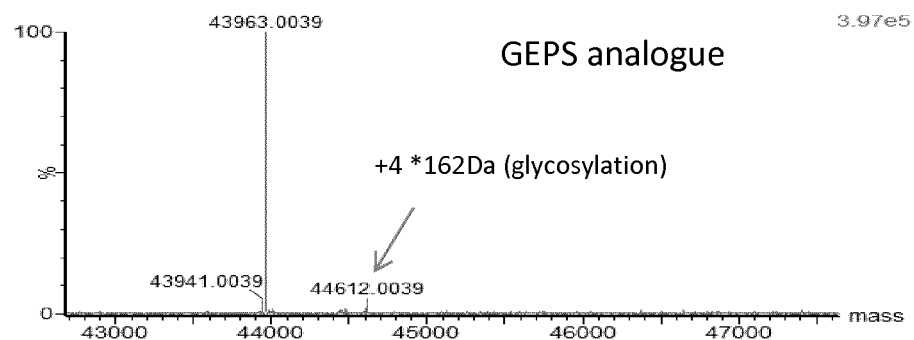
FIG. 3 shows an example of a deconvoluted mass spectrum for an analogue containing the GEPS repeat, analysed by reversed phase LC/MS in the supernatant. The expected mass of the compound is 43963.76 Da, which is the main mass. One of additional masses is additional four times 162 Da, which is equal to four hexose moieties.

The extended insulin analogue appears in MS with a single mass profile. If serine residues are present in the extension sequence, like the GEPS repeat examples, glycosylation is observed (see FIG. 3). Multiple negative charges in the sequence reduce the number of sugar moieties to mainly involve up to 4 sugar residues whereas lack of negative charges result in glycosylation with multiple sugar moieties.

Figure 4:
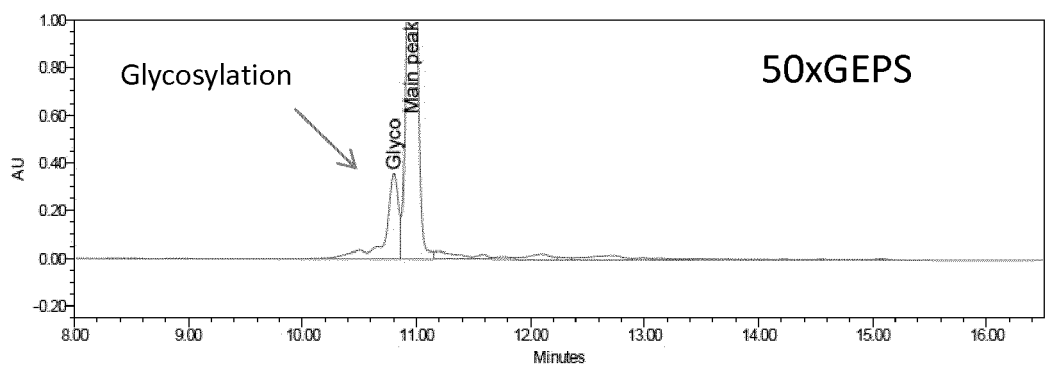
FIG. 4 shows an UV purity analysis of a purified analogue containing the GEPS repeat using reversed phase LC chromatography. The major impurity seen has been identified as a glycosylated product. As a result of the low resolution from the main peak it was not removed during the purification process.

The amount of glycosylation for an analogue with GEPS repeats extension lie in the range between 10 and 30%, depending on the number of serine residues, e.g. length of extension sequence (see FIG. 4). It is difficult to remove this glycosylation during the purification process because of low resolution power of the reversed phase.

Figure 5:
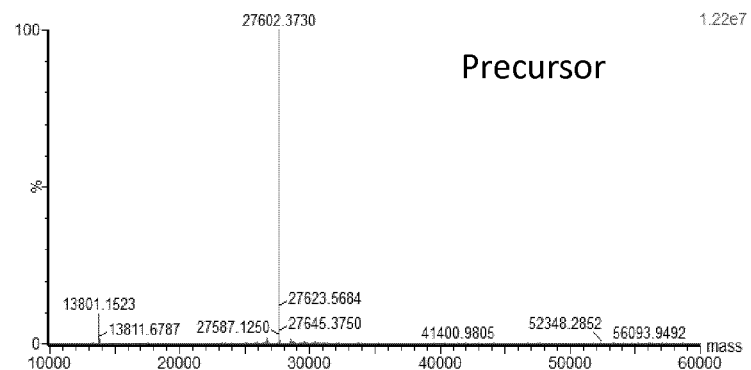
FIG. 5 shows an example of a deconvoluted mass spectrum for an analogue precursor containing the GQEP repeat analysed by reversed phase LC/MS in the supernatant. The expected mass of the compound is 27602.75 Da, which is the main mass. The additional major mass equals half the peak mass and is an artefact of the algorithm used to deconvolution the mass spectrum.
Figure 6:
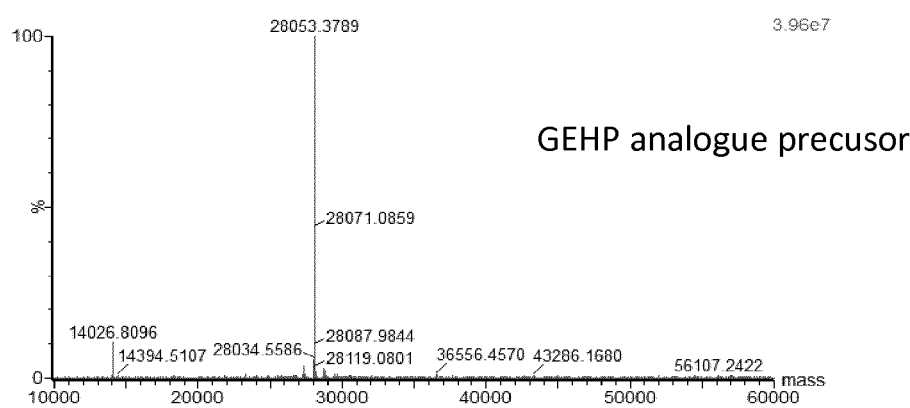
FIG. 6 shows an example of a deconvoluted mass spectrum for an analogue precursor containing the GEHP repeat analysed by reversed phase LC/MS in the supernatant. The expected mass of the compound is 28053.27 Da, which is the main mass. The additional major mass equals half the peak mass and is an artefact of the algorithm used to deconvolution the mass spectrum.

Removal of serine residues from the sequence as is seen for the analogues containing G, E, A, H, Q and P result in non-glycosylated extension (see FIGS. 5 and 6).

Example 55

Determination of Viscosity

This example represents a comparative example showing the results of a viscosity determination of oligomer extended insulin analogues representative of the invention (i.e. the compounds of Examples 1-5) compared to the viscosity of an oligomer extended insulin analogues analogue representative of the prior art, i.e. Compound A of the general Formula I, wherein "Ins" represents [A21Q*, desB30]; * indicates point of extension; "Ext" represents the extension "GEPS"; and the number of amino acid residues in the extension is and 200.

The viscosity was estimated by dynamic light scattering (DLS) using a DynaPro PR™ (Wyatt technology, Santa Barbara, Calif., USA). In DLS, the diffusion coefficient is determined, and from that the hydrodynamic radius can be obtained from the Stoke-Einstein equation. Viscosity is included in the Stoke-Einstein equation, and the correct viscosity is needed for an accurate determination of the hydrodynamic radius. By utilizing a molecule of known size (Polystyrene standard Nanosphere beads; diameter mean: 147 nm) and determine the apparent size (changes with viscosity) of this standard in the oligomer extended insulin solutions the actual viscosity can be calculated at a given condition. The apparent bead radius was converted to viscosity (cP): (apparent radius PS bead [nm]/real radius PS bead [nm])×viscosity of solvent (e.g. 0.893 cP at 25° C.).

The results of this determination are presented in Table 6 below, and the figures clearly show the compound representative of the invention have lower viscosity when compared to the compound representative of the prior art.

TABLE 6

Viscosity in a 600 µM solution

| Ex. No. | Viscosity η (cP) (7° C., no Zn) | Viscosity η (cP) (25° C., no Zn) | Viscosity η (cP) (7° C., with Zn) | Viscosity η (cP) (25° C., with Zn) |
|---|---|---|---|---|
| 1 | 4.49 ± 0.09 | 2.70 ± 0.03 | 6.14 ± 0.12$^c$ | 3.76 ± 0.03$^b$ |
| 2 | 2.41 ± 0.02 | 1.45 ± 0.01 | 2.55 ± 0.01$^c$ | 1.51 ± 0.02$^b$ |
| 3 | 2.23 ± 0.01 | 1.36 ± 0.01 | 2.35 ± 0.03$^c$ | 1.42 ± 0.00$^b$ |
|   |   |   |   | 1.51 ± 0.00$^d$ |
| 4 | 2.99 ± 0.01 | 1.87 ± 0.01 | 3.13 ± 0.02$^c$ | 2.04 ± 0.01$^b$ |
| 5 | 3.43 ± 0.00 | 2.06 ± 0.00 | 2.88 ± 0.00$^c$ | 1.83 ± 0.00$^b$ |
| 37 | — | — | — | 1.64 ± 0.02$^d$ |
| 38 | — | — | — | 1.49 ± 0.01$^d$ |
| 39 | — | — | — | 1.66 ± 0.00$^d$ |
| 40 | — | — | — | 1.61 ± 0.01$^d$ |
| Cp. A | 6.22 ± 0.71 | 3.14 ± 0.10 | 8.66 ± 0.91$^c$ | 5.73 ± 0.60$^c$ |

$^b$10 mM phosphate buffer, pH 7.4, 28 mM m-cresol, 3 $Zn^{2+}$/6 Ins;
$^c$10 mM phosphate buffer, pH 7.4, 58 mM phenol, 3 $Zn^{2+}$/6 Ins; and
$^d$20 mM NaCl, pH 7.4, 1.4% glycerol, 19 mM phenol, 19 mM m-cresol, 4 $Zn^{2+}$/6 Ins.

SEQUENCE LISTING

<160> NUMBER OF SEQ ID NOS: 62

<210> SEQ ID NO 1
<211> LENGTH: 21
<212> TYPE: PRT
<213> ORGANISM: Artificial Sequence
<220> FEATURE:
<223> OTHER INFORMATION: A-chain of analogue [A21Q] of human insulin;
      Ex. Nos. 1-5.

<400> SEQUENCE: 1

Gly Ile Val Glu Gln Cys Cys Thr Ser Ile Cys Ser Leu Tyr Gln Leu
1               5                   10                  15

Glu Asn Tyr Cys Gln
            20

<210> SEQ ID NO 2
<211> LENGTH: 21
<212> TYPE: PRT
<213> ORGANISM: Artificial Sequence
<220> FEATURE:
<223> OTHER INFORMATION: A-chain of analogue [A14E, A21G] of human
      insulin; Ex. Nos. 6-11 and 59-61.

<400> SEQUENCE: 2

Gly Ile Val Glu Gln Cys Cys Thr Ser Ile Cys Ser Leu Glu Gln Leu

Glu Asn Tyr Cys Gly
            20

<210> SEQ ID NO 3
<211> LENGTH: 21
<212> TYPE: PRT
<213> ORGANISM: Artificial Sequence
<220> FEATURE:
<223> OTHER INFORMATION: A-chain of analogue [A21G] of human insulin;
      Ex. Nos. 12-58 and 62-77.

<400> SEQUENCE: 3

Gly Ile Val Glu Gln Cys Cys Thr Ser Ile Cys Ser Leu Tyr Gln Leu
1               5                   10                  15

Glu Asn Tyr Cys Gly
            20

<210> SEQ ID NO 4
<211> LENGTH: 29
<212> TYPE: PRT
<213> ORGANISM: Artificial Sequence
<220> FEATURE:
<223> OTHER INFORMATION: B-chain of analogue [desB30] of human insulin;
      Ex. Nos. 1-5, 12-58 and 62-77.

<400> SEQUENCE: 4

Phe Val Asn Gln His Leu Cys Gly Asp His Leu Val Glu Ala Leu Tyr
1               5                   10                  15

Leu Val Cys Gly Glu Arg Gly Phe Phe Tyr Thr Pro Lys
            20                  25

<210> SEQ ID NO 5
<211> LENGTH: 29
<212> TYPE: PRT
<213> ORGANISM: Artificial Sequence
<220> FEATURE:
<223> OTHER INFORMATION: B-chain of analogue [B25H, desB30] of human
      insulin; Ex. Nos. 6-11 and 59-61.

<400> SEQUENCE: 5

Phe Val Asn Gln His Leu Cys Gly Asp His Leu Val Glu Ala Leu Tyr
1               5                   10                  15

Leu Val Cys Gly Glu Arg Gly Phe His Tyr Thr Pro Lys
            20                  25

<210> SEQ ID NO 6
<211> LENGTH: 200
<212> TYPE: PRT
<213> ORGANISM: Artificial Sequence
<220> FEATURE:
<223> OTHER INFORMATION: C-terminal extension [(GQEP)50] of the A-chain
      of the analogue of Ex. Nos. 1 and 6.

<400> SEQUENCE: 6

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Gln Glu Pro Gly Gln Glu Pro
    50                  55                  60

Gly Gln Glu Pro Gly Gln Glu Pro Gly Gln Glu Pro Gly Gln Glu Pro
65                  70                  75                  80

Gly Gln Glu Pro Gly Gln Glu Pro Gly Gln Glu Pro Gly Gln Glu Pro
                85                  90                  95

Gly Gln Glu Pro Gly Gln Glu Pro Gly Gln Glu Pro Gly Gln Glu Pro
            100                 105                 110

Gly Gln Glu Pro Gly Gln Glu Pro Gly Gln Glu Pro Gly Gln Glu Pro
        115                 120                 125

Gly Gln Glu Pro Gly Gln Glu Pro Gly Gln Glu Pro Gly Gln Glu Pro
    130                 135                 140

Gly Gln Glu Pro Gly Gln Glu Pro Gly Gln Glu Pro Gly Gln Glu Pro
145                 150                 155                 160

Gly Gln Glu Pro Gly Gln Glu Pro Gly Gln Glu Pro Gly Gln Glu Pro
                165                 170                 175

Gly Gln Glu Pro Gly Gln Glu Pro Gly Gln Glu Pro Gly Gln Glu Pro
            180                 185                 190

Gly Gln Glu Pro Gly Gln Glu Pro
        195                 200

<210> SEQ ID NO 7
<211> LENGTH: 200
<212> TYPE: PRT
<213> ORGANISM: Artificial Sequence
<220> FEATURE:
<223> OTHER INFORMATION: C-terminal extension [(GAPQ)50] of the A-chain
      of the analogue of Ex. Nos. 2 and 7.

<400> SEQUENCE: 7

Gly Ala Pro Gln Gly Ala Pro Gln Gly Ala Pro Gln Gly Ala Pro Gln
1               5                   10                  15

Gly Ala Pro Gln Gly Ala Pro Gln Gly Ala Pro Gln Gly Ala Pro Gln
            20                  25                  30

Gly Ala Pro Gln Gly Ala Pro Gln Gly Ala Pro Gln Gly Ala Pro Gln
        35                  40                  45

Gly Ala Pro Gln Gly Ala Pro Gln Gly Ala Pro Gln Gly Ala Pro Gln
    50                  55                  60

Gly Ala Pro Gln Gly Ala Pro Gln Gly Ala Pro Gln Gly Ala Pro Gln
65                  70                  75                  80

Gly Ala Pro Gln Gly Ala Pro Gln Gly Ala Pro Gln Gly Ala Pro Gln
                85                  90                  95

Gly Ala Pro Gln Gly Ala Pro Gln Gly Ala Pro Gln Gly Ala Pro Gln
            100                 105                 110

Gly Ala Pro Gln Gly Ala Pro Gln Gly Ala Pro Gln Gly Ala Pro Gln
        115                 120                 125

Gly Ala Pro Gln Gly Ala Pro Gln Gly Ala Pro Gln Gly Ala Pro Gln
    130                 135                 140

Gly Ala Pro Gln Gly Ala Pro Gln Gly Ala Pro Gln Gly Ala Pro Gln
145                 150                 155                 160

Gly Ala Pro Gln Gly Ala Pro Gln Gly Ala Pro Gln Gly Ala Pro Gln
                165                 170                 175

Gly Ala Pro Gln Gly Ala Pro Gln Gly Ala Pro Gln Gly Ala Pro Gln
            180                 185                 190

Gly Ala Pro Gln Gly Ala Pro Gln
        195                 200

<210> SEQ ID NO 8

<211> LENGTH: 200
<212> TYPE: PRT
<213> ORGANISM: Artificial Sequence
<220> FEATURE:
<223> OTHER INFORMATION: C-terminal extension [(GQAP)50] of the A-chain of the analogue of Ex. Nos. 3, 56, 59 and 62.

<400> SEQUENCE: 8

```
Gly Gln Ala Pro Gly Gln Ala Pro Gly Gln Ala Pro Gly Gln Ala Pro
1               5                   10                  15

Gly Gln Ala Pro Gly Gln Ala Pro Gly Gln Ala Pro
            20                  25                  30

Gly Gln Ala Pro Gly Gln Ala Pro Gly Gln Ala Pro Gly Gln Ala Pro
        35                  40                  45

Gly Gln Ala Pro Gly Gln Ala Pro Gly Gln Ala Pro
    50                  55                  60

Gly Gln Ala Pro Gly Gln Ala Pro Gly Gln Ala Pro Gly Gln Ala Pro
65                  70                  75                  80

Gly Gln Ala Pro Gly Gln Ala Pro Gly Gln Ala Pro Gly Gln Ala Pro
            85                  90                  95

Gly Gln Ala Pro Gly Gln Ala Pro Gly Gln Ala Pro Gly Gln Ala Pro
            100                 105                 110

Gly Gln Ala Pro Gly Gln Ala Pro Gly Gln Ala Pro
        115                 120                 125

Gly Gln Ala Pro Gly Gln Ala Pro Gly Gln Ala Pro Gly Gln Ala Pro
    130                 135                 140

Gly Gln Ala Pro Gly Gln Ala Pro Gly Gln Ala Pro Gly Gln Ala Pro
145                 150                 155                 160

Gly Gln Ala Pro Gly Gln Ala Pro Gly Gln Ala Pro Gly Gln Ala Pro
                165                 170                 175

Gly Gln Ala Pro Gly Gln Ala Pro Gly Gln Ala Pro
            180                 185                 190

Gly Gln Ala Pro Gly Gln Ala Pro
        195                 200
```

<210> SEQ ID NO 9
<211> LENGTH: 200
<212> TYPE: PRT
<213> ORGANISM: Artificial Sequence
<220> FEATURE:
<223> OTHER INFORMATION: C-terminal extension [(GEPH)50] of the A-chain of the analogue of Ex. Nos. 4 and 9.

<400> SEQUENCE: 9

```
Gly Glu Pro His Gly Glu Pro His Gly Glu Pro His Gly Glu Pro His
1               5                   10                  15

Gly Glu Pro His Gly Glu Pro His Gly Glu Pro His
            20                  25                  30

Gly Glu Pro His Gly Glu Pro His Gly Glu Pro His
        35                  40                  45

Gly Glu Pro His Gly Glu Pro His Gly Glu Pro His
    50                  55                  60

Gly Glu Pro His Gly Glu Pro His Gly Glu Pro His Gly Glu Pro His
65                  70                  75                  80

Gly Glu Pro His Gly Glu Pro His Gly Glu Pro His
            85                  90                  95

Gly Glu Pro His Gly Glu Pro His Gly Glu Pro His
            100                 105                 110
```

```
Gly Glu Pro His Gly Glu Pro His Gly Glu Pro His Gly Glu Pro His
        115                 120                 125

Gly Glu Pro His Gly Glu Pro His Gly Glu Pro His Gly Glu Pro His
        130                 135                 140

Gly Glu Pro His Gly Glu Pro His Gly Glu Pro His Gly Glu Pro His
145                 150                 155                 160

Gly Glu Pro His Gly Glu Pro His Gly Glu Pro His Gly Glu Pro His
        165                 170                 175

Gly Glu Pro His Gly Glu Pro His Gly Glu Pro His Gly Glu Pro His
        180                 185                 190

Gly Glu Pro His Gly Glu Pro His
        195                 200

<210> SEQ ID NO 10
<211> LENGTH: 200
<212> TYPE: PRT
<213> ORGANISM: Artificial Sequence
<220> FEATURE:
<223> OTHER INFORMATION: C-terminal extension [(GEHP)50] of the A-chain
      of the analogue of Ex. Nos. 5 and 10.

<400> SEQUENCE: 10

Gly Glu His Pro Gly Glu His Pro Gly Glu His Pro Gly Glu His Pro
1               5                   10                  15

Gly Glu His Pro Gly Glu His Pro Gly Glu His Pro Gly Glu His Pro
            20                  25                  30

Gly Glu His Pro Gly Glu His Pro Gly Glu His Pro Gly Glu His Pro
        35                  40                  45

Gly Glu His Pro Gly Glu His Pro Gly Glu His Pro Gly Glu His Pro
    50                  55                  60

Gly Glu His Pro Gly Glu His Pro Gly Glu His Pro Gly Glu His Pro
65                  70                  75                  80

Gly Glu His Pro Gly Glu His Pro Gly Glu His Pro Gly Glu His Pro
                85                  90                  95

Gly Glu His Pro Gly Glu His Pro Gly Glu His Pro Gly Glu His Pro
            100                 105                 110

Gly Glu His Pro Gly Glu His Pro Gly Glu His Pro Gly Glu His Pro
        115                 120                 125

Gly Glu His Pro Gly Glu His Pro Gly Glu His Pro Gly Glu His Pro
        130                 135                 140

Gly Glu His Pro Gly Glu His Pro Gly Glu His Pro Gly Glu His Pro
145                 150                 155                 160

Gly Glu His Pro Gly Glu His Pro Gly Glu His Pro Gly Glu His Pro
        165                 170                 175

Gly Glu His Pro Gly Glu His Pro Gly Glu His Pro Gly Glu His Pro
        180                 185                 190

Gly Glu His Pro Gly Glu His Pro
        195                 200

<210> SEQ ID NO 11
<211> LENGTH: 200
<212> TYPE: PRT
<213> ORGANISM: Artificial Sequence
<220> FEATURE:
<223> OTHER INFORMATION: C-terminal extension [(GAPH)50] of the A-chain
      of the analogue of Ex. No. 11.

<400> SEQUENCE: 11
```

```
Gly Ala Pro His Gly Ala Pro His Gly Ala Pro His Gly Ala Pro His
1               5                   10                  15

Gly Ala Pro His Gly Ala Pro His Gly Ala Pro His
                20                  25                  30

Gly Ala Pro His Gly Ala Pro His Gly Ala Pro His Gly Ala Pro His
            35                  40                  45

Gly Ala Pro His Gly Ala Pro His Gly Ala Pro His
        50                  55                  60

Gly Ala Pro His Gly Ala Pro His Gly Ala Pro His Gly Ala Pro His
65              70                  75                  80

Gly Ala Pro His Gly Ala Pro His Gly Ala Pro His
            85                  90                  95

Gly Ala Pro His Gly Ala Pro His Gly Ala Pro His
        100                 105                 110

Gly Ala Pro His Gly Ala Pro His Gly Ala Pro His
    115                 120                 125

Gly Ala Pro His Gly Ala Pro His Gly Ala Pro His
    130                 135                 140

Gly Ala Pro His Gly Ala Pro His Gly Ala Pro His Gly Ala Pro His
145             150                 155                 160

Gly Ala Pro His Gly Ala Pro His Gly Ala Pro His
        165                 170                 175

Gly Ala Pro His Gly Ala Pro His Gly Ala Pro His
        180                 185                 190

Gly Ala Pro His Gly Ala Pro His
    195                 200

<210> SEQ ID NO 12
<211> LENGTH: 208
<212> TYPE: PRT
<213> ORGANISM: Artificial Sequence
<220> FEATURE:
<223> OTHER INFORMATION: C-terminal extension [(GEHPGAPHGQEPGQAP)13] of
      the A-chain of the analogue of Ex. No. 12.

<400> SEQUENCE: 12

Gly Glu His Pro Gly Ala Pro His Gly Gln Glu Pro Gly Gln Ala Pro
1               5                   10                  15

Gly Glu His Pro Gly Ala Pro His Gly Gln Glu Pro Gly Gln Ala Pro
                20                  25                  30

Gly Glu His Pro Gly Ala Pro His Gly Gln Glu Pro Gly Gln Ala Pro
            35                  40                  45

Gly Glu His Pro Gly Ala Pro His Gly Gln Glu Pro Gly Gln Ala Pro
        50                  55                  60

Gly Glu His Pro Gly Ala Pro His Gly Gln Glu Pro Gly Gln Ala Pro
65              70                  75                  80

Gly Glu His Pro Gly Ala Pro His Gly Gln Glu Pro Gly Gln Ala Pro
            85                  90                  95

Gly Glu His Pro Gly Ala Pro His Gly Gln Glu Pro Gly Gln Ala Pro
        100                 105                 110

Gly Glu His Pro Gly Ala Pro His Gly Gln Glu Pro Gly Gln Ala Pro
    115                 120                 125

Gly Glu His Pro Gly Ala Pro His Gly Gln Glu Pro Gly Gln Ala Pro
    130                 135                 140

Gly Glu His Pro Gly Ala Pro His Gly Gln Glu Pro Gly Gln Ala Pro
```

```
145                 150                 155                 160
Gly Glu His Pro Gly Ala Pro His Gly Gln Glu Pro Gly Gln Ala Pro
                165                 170                 175

Gly Glu His Pro Gly Ala Pro His Gly Gln Glu Pro Gly Gln Ala Pro
            180                 185                 190

Gly Glu His Pro Gly Ala Pro His Gly Gln Glu Pro Gly Gln Ala Pro
        195                 200                 205

<210> SEQ ID NO 13
<211> LENGTH: 201
<212> TYPE: PRT
<213> ORGANISM: Artificial Sequence
<220> FEATURE:
<223> OTHER INFORMATION: C-terminal extension [(GEH)67] of the A-chain
      of the analogue of Ex. No. 13.

<400> SEQUENCE: 13

Gly Glu His Gly Glu His Gly Glu His Gly Glu His Gly Glu His Gly
1               5                   10                  15

Glu His Gly Glu His Gly Glu His Gly Glu His Gly Glu His Gly Glu
            20                  25                  30

His Gly Glu His Gly Glu His Gly Glu His Gly Glu His Gly Glu His
        35                  40                  45

Gly Glu His Gly Glu His Gly Glu His Gly Glu His Gly Glu His Gly
    50                  55                  60

Glu His Gly Glu His Gly Glu His Gly Glu His Gly Glu His Gly Glu
65                  70                  75                  80

His Gly Glu His Gly Glu His Gly Glu His Gly Glu His Gly Glu His
                85                  90                  95

Gly Glu His Gly Glu His Gly Glu His Gly Glu His Gly Glu His Gly
            100                 105                 110

Glu His Gly Glu His Gly Glu His Gly Glu His Gly Glu His Gly Glu
        115                 120                 125

His Gly Glu His Gly Glu His Gly Glu His Gly Glu His Gly Glu His
    130                 135                 140

Gly Glu His Gly Glu His Gly Glu His Gly Glu His Gly Glu His Gly
145                 150                 155                 160

Glu His Gly Glu His Gly Glu His Gly Glu His Gly Glu His Gly Glu
                165                 170                 175

His Gly Glu His Gly Glu His Gly Glu His Gly Glu His Gly Glu His
            180                 185                 190

Gly Glu His Gly Glu His Gly Glu His
        195                 200

<210> SEQ ID NO 14
<211> LENGTH: 201
<212> TYPE: PRT
<213> ORGANISM: Artificial Sequence
<220> FEATURE:
<223> OTHER INFORMATION: C-terminal extension [(GQA)67] of the A-chain
      of the analogue of Ex. No. 14.

<400> SEQUENCE: 14

Gly Gln Ala Gly Gln Ala Gly Gln Ala Gly Gln Ala Gly Gln Ala Gly
1               5                   10                  15

Gln Ala Gly Gln Ala Gly Gln Ala Gly Gln Ala Gly Gln Ala Gly Gln
            20                  25                  30

Ala Gly Gln Ala Gly Gln Ala Gly Gln Ala Gly Gln Ala Gly Gln Ala
```

```
                35                  40                  45
Gly Gln Ala Gly Gln Ala Gly Gln Ala Gly Gln Ala Gly
    50                  55                  60
Gln Ala Gly Gln Ala Gly Gln Ala Gly Gln Ala Gly Gln
65                  70                  75                  80
Ala Gly Gln Ala Gly Gln Ala Gly Gln Ala Gly Gln Ala
                85                  90                  95
Gly Gln Ala Gly Gln Ala Gly Gln Ala Gly Gln Ala Gly
            100                 105                 110
Gln Ala Gly Gln Ala Gly Gln Ala Gly Gln Ala Gly Gln
        115                 120                 125
Ala Gly Gln Ala Gly Gln Ala Gly Gln Ala Gly Gln Ala
    130                 135                 140
Gly Gln Ala Gly Gln Ala Gly Gln Ala Gly Gln Ala Gly
145                 150                 155                 160
Gln Ala Gly Gln Ala Gly Gln Ala Gly Gln Ala Gly Gln
            165                 170                 175
Ala Gly Gln Ala Gly Gln Ala Gly Gln Ala Gly Gln Ala
        180                 185                 190
Gly Gln Ala Gly Gln Ala Gly Gln Ala
    195                 200

<210> SEQ ID NO 15
<211> LENGTH: 201
<212> TYPE: PRT
<213> ORGANISM: Artificial Sequence
<220> FEATURE:
<223> OTHER INFORMATION: C-terminal extension [(GQE)67] of the A-chain
      of the analogue of Ex. No. 15.

<400> SEQUENCE: 15

Gly Gln Glu Gly Gln Glu Gly Gln Glu Gly Gln Glu Gly Gln Glu Gly
1               5                   10                  15
Gln Glu Gly Gln Glu Gly Gln Glu Gly Gln Glu Gly Gln Glu Gly Gln
            20                  25                  30
Glu Gly Gln Glu Gly Gln Glu Gly Gln Glu Gly Gln Glu Gly Gln Glu
        35                  40                  45
Gly Gln Glu Gly Gln Glu Gly Gln Glu Gly Gln Glu Gly Gln Glu Gly
    50                  55                  60
Gln Glu Gly Gln Glu Gly Gln Glu Gly Gln Glu Gly Gln Glu Gly Gln
65                  70                  75                  80
Glu Gly Gln Glu Gly Gln Glu Gly Gln Glu Gly Gln Glu Gly Gln Glu
                85                  90                  95
Gly Gln Glu Gly Gln Glu Gly Gln Glu Gly Gln Glu Gly Gln Glu Gly
            100                 105                 110
Gln Glu Gly Gln Glu Gly Gln Glu Gly Gln Glu Gly Gln Glu Gly Gln
        115                 120                 125
Glu Gly Gln Glu Gly Gln Glu Gly Gln Glu Gly Gln Glu Gly Gln Glu
    130                 135                 140
Gly Gln Glu Gly Gln Glu Gly Gln Glu Gly Gln Glu Gly Gln Glu Gly
145                 150                 155                 160
Gln Glu Gly Gln Glu Gly Gln Glu Gly Gln Glu Gly Gln Glu Gly Gln
                165                 170                 175
Glu Gly Gln Glu Gly Gln Glu Gly Gln Glu Gly Gln Glu Gly Gln Glu
            180                 185                 190
```

-continued

```
Gly Gln Glu Gly Gln Glu Gly Gln Glu
        195                 200
```

<210> SEQ ID NO 16
<211> LENGTH: 200
<212> TYPE: PRT
<213> ORGANISM: Artificial Sequence
<220> FEATURE:
<223> OTHER INFORMATION: C-terminal extension [(GEQH)50] of the A-chain
      of the analogue of Ex. No. 16.

<400> SEQUENCE: 16

```
Gly Glu Gln His Gly Glu Gln His Gly Glu Gln His Gly Glu Gln His
1               5                   10                  15

Gly Glu Gln His Gly Glu Gln His Gly Glu Gln His Gly Glu Gln His
            20                  25                  30

Gly Glu Gln His Gly Glu Gln His Gly Glu Gln His Gly Glu Gln His
        35                  40                  45

Gly Glu Gln His Gly Glu Gln His Gly Glu Gln His Gly Glu Gln His
  50                  55                  60

Gly Glu Gln His Gly Glu Gln His Gly Glu Gln His Gly Glu Gln His
65              70                  75                  80

Gly Glu Gln His Gly Glu Gln His Gly Glu Gln His Gly Glu Gln His
            85                  90                  95

Gly Glu Gln His Gly Glu Gln His Gly Glu Gln His Gly Glu Gln His
        100                 105                 110

Gly Glu Gln His Gly Glu Gln His Gly Glu Gln His Gly Glu Gln His
  115                 120                 125

Gly Glu Gln His Gly Glu Gln His Gly Glu Gln His Gly Glu Gln His
130             135                 140

Gly Glu Gln His Gly Glu Gln His Gly Glu Gln His Gly Glu Gln His
145                 150                 155                 160

Gly Glu Gln His Gly Glu Gln His Gly Glu Gln His Gly Glu Gln His
            165                 170                 175

Gly Glu Gln His Gly Glu Gln His Gly Glu Gln His Gly Glu Gln His
        180                 185                 190

Gly Glu Gln His Gly Glu Gln His
  195                 200
```

<210> SEQ ID NO 17
<211> LENGTH: 200
<212> TYPE: PRT
<213> ORGANISM: Artificial Sequence
<220> FEATURE:
<223> OTHER INFORMATION: C-terminal extension
      [(GQEPGQEPGQEPGAPH)12GQEPGQEP] of the A-chain of the analogue of
      Ex. No. 17.

<400> SEQUENCE: 17

```
Gly Gln Glu Pro Gly Gln Glu Pro Gly Gln Glu Pro Gly Ala Pro His
1               5                   10                  15

Gly Gln Glu Pro Gly Gln Glu Pro Gly Gln Glu Pro Gly Ala Pro His
            20                  25                  30

Gly Gln Glu Pro Gly Gln Glu Pro Gly Gln Glu Pro Gly Ala Pro His
        35                  40                  45

Gly Gln Glu Pro Gly Gln Glu Pro Gly Gln Glu Pro Gly Ala Pro His
  50                  55                  60

Gly Gln Glu Pro Gly Gln Glu Pro Gly Gln Glu Pro Gly Ala Pro His
65              70                  75                  80
```

Gly Gln Glu Pro Gly Gln Glu Pro Gly Ala Pro His
            85                  90                  95

Gly Gln Glu Pro Gly Gln Glu Pro Gly Ala Pro His
            100                 105                 110

Gly Gln Glu Pro Gly Gln Glu Pro Gly Ala Pro His
            115                 120                 125

Gly Gln Glu Pro Gly Gln Glu Pro Gly Ala Pro His
            130                 135                 140

Gly Gln Glu Pro Gly Gln Glu Pro Gly Ala Pro His
145                 150                 155                 160

Gly Gln Glu Pro Gly Gln Glu Pro Gly Ala Pro His
            165                 170                 175

Gly Gln Glu Pro Gly Gln Glu Pro Gly Ala Pro His
            180                 185                 190

Gly Gln Glu Pro Gly Gln Glu Pro
            195                 200

<210> SEQ ID NO 18
<211> LENGTH: 200
<212> TYPE: PRT
<213> ORGANISM: Artificial Sequence
<220> FEATURE:
<223> OTHER INFORMATION: C-terminal extension
    [(GQEPGQEPGAPHGAPH)12GQEPGQEP] of the A-chain of the analogue of
    Ex. No. 18.

<400> SEQUENCE: 18

Gly Gln Glu Pro Gly Gln Glu Pro Gly Ala Pro His Gly Ala Pro His
1               5                   10                  15

Gly Gln Glu Pro Gly Gln Glu Pro Gly Ala Pro His Gly Ala Pro His
            20                  25                  30

Gly Gln Glu Pro Gly Gln Glu Pro Gly Ala Pro His Gly Ala Pro His
            35                  40                  45

Gly Gln Glu Pro Gly Gln Glu Pro Gly Ala Pro His Gly Ala Pro His
    50                  55                  60

Gly Gln Glu Pro Gly Gln Glu Pro Gly Ala Pro His Gly Ala Pro His
65                  70                  75                  80

Gly Gln Glu Pro Gly Gln Glu Pro Gly Ala Pro His Gly Ala Pro His
            85                  90                  95

Gly Gln Glu Pro Gly Gln Glu Pro Gly Ala Pro His Gly Ala Pro His
            100                 105                 110

Gly Gln Glu Pro Gly Gln Glu Pro Gly Ala Pro His Gly Ala Pro His
            115                 120                 125

Gly Gln Glu Pro Gly Gln Glu Pro Gly Ala Pro His Gly Ala Pro His
            130                 135                 140

Gly Gln Glu Pro Gly Gln Glu Pro Gly Ala Pro His Gly Ala Pro His
145                 150                 155                 160

Gly Gln Glu Pro Gly Gln Glu Pro Gly Ala Pro His Gly Ala Pro His
            165                 170                 175

Gly Gln Glu Pro Gly Gln Glu Pro Gly Ala Pro His Gly Ala Pro His
            180                 185                 190

Gly Gln Glu Pro Gly Gln Glu Pro
            195                 200

<210> SEQ ID NO 19
<211> LENGTH: 200

```
<212> TYPE: PRT
<213> ORGANISM: Artificial Sequence
<220> FEATURE:
<223> OTHER INFORMATION: C-terminal extension
      [(GQAPGQAPGQAPGAPH)12GQAPGQAP] of the A-chain of the analogue of
      Ex. No. 20.

<400> SEQUENCE: 19

Gly Gln Ala Pro Gly Gln Ala Pro Gly Gln Ala Pro Gly Ala Pro His
1               5                   10                  15

Gly Gln Ala Pro Gly Gln Ala Pro Gly Gln Ala Pro Gly Ala Pro His
            20                  25                  30

Gly Gln Ala Pro Gly Gln Ala Pro Gly Gln Ala Pro Gly Ala Pro His
        35                  40                  45

Gly Gln Ala Pro Gly Gln Ala Pro Gly Gln Ala Pro Gly Ala Pro His
    50                  55                  60

Gly Gln Ala Pro Gly Gln Ala Pro Gly Gln Ala Pro Gly Ala Pro His
65                  70                  75                  80

Gly Gln Ala Pro Gly Gln Ala Pro Gly Gln Ala Pro Gly Ala Pro His
                85                  90                  95

Gly Gln Ala Pro Gly Gln Ala Pro Gly Gln Ala Pro Gly Ala Pro His
            100                 105                 110

Gly Gln Ala Pro Gly Gln Ala Pro Gly Gln Ala Pro Gly Ala Pro His
        115                 120                 125

Gly Gln Ala Pro Gly Gln Ala Pro Gly Gln Ala Pro Gly Ala Pro His
    130                 135                 140

Gly Gln Ala Pro Gly Gln Ala Pro Gly Gln Ala Pro Gly Ala Pro His
145                 150                 155                 160

Gly Gln Ala Pro Gly Gln Ala Pro Gly Gln Ala Pro Gly Ala Pro His
                165                 170                 175

Gly Gln Ala Pro Gly Gln Ala Pro Gly Gln Ala Pro Gly Ala Pro His
            180                 185                 190

Gly Gln Ala Pro Gly Gln Ala Pro
        195                 200

<210> SEQ ID NO 20
<211> LENGTH: 200
<212> TYPE: PRT
<213> ORGANISM: Artificial Sequence
<220> FEATURE:
<223> OTHER INFORMATION: C-terminal extension
      [(GQAPGQAPGAPHGAPH)12GQAPGQAP] of the A-chain of the analogue of
      Ex. No. 21.

<400> SEQUENCE: 20

Gly Gln Ala Pro Gly Gln Ala Pro Gly Ala Pro His Gly Ala Pro His
1               5                   10                  15

Gly Gln Ala Pro Gly Gln Ala Pro Gly Ala Pro His Gly Ala Pro His
            20                  25                  30

Gly Gln Ala Pro Gly Gln Ala Pro Gly Ala Pro His Gly Ala Pro His
        35                  40                  45

Gly Gln Ala Pro Gly Gln Ala Pro Gly Ala Pro His Gly Ala Pro His
    50                  55                  60

Gly Gln Ala Pro Gly Gln Ala Pro Gly Ala Pro His Gly Ala Pro His
65                  70                  75                  80

Gly Gln Ala Pro Gly Gln Ala Pro Gly Ala Pro His Gly Ala Pro His
                85                  90                  95

Gly Gln Ala Pro Gly Gln Ala Pro Gly Ala Pro His Gly Ala Pro His
```

Gly Gln Ala Pro Gly Gln Ala Pro Gly Ala Pro His Gly Ala Pro His
           115                 120                 125

Gly Gln Ala Pro Gly Gln Ala Pro Gly Ala Pro His Gly Ala Pro His
           130                 135                 140

Gly Gln Ala Pro Gly Gln Ala Pro Gly Ala Pro His Gly Ala Pro His
145                 150                 155                 160

Gly Gln Ala Pro Gly Gln Ala Pro Gly Ala Pro His Gly Ala Pro His
               165                 170                 175

Gly Gln Ala Pro Gly Gln Ala Pro Gly Ala Pro His Gly Ala Pro His
               180                 185                 190

Gly Gln Ala Pro Gly Gln Ala Pro
           195                 200

<210> SEQ ID NO 21
<211> LENGTH: 200
<212> TYPE: PRT
<213> ORGANISM: Artificial Sequence
<220> FEATURE:
<223> OTHER INFORMATION: C-terminal extension [[A,E,G,H,P,Q](200 in
      random)] of the A-chain of the analogue of Ex. No. 23.

<400> SEQUENCE: 21

Gly Gln Glu Pro Gly Ala Pro His Gly Glu Pro His Gly Ala Pro His
1               5                   10                  15

Gly Glu Pro His Gly Ala Pro Gln Gly Gln Glu Pro Gly Gln Glu Pro
               20                  25                  30

Gly Gln Glu Pro Gly Gln Ala Pro Gly Gln Glu Pro Gly Glu His Pro
           35                  40                  45

Gly Ala Pro Gln Gly Ala Pro Gln Gly Gln Glu Pro Gly Ala Pro Gln
           50                  55                  60

Gly Gln Glu Pro Gly Ala Pro His Gly Glu His Pro Gly Glu His Pro
65                  70                  75                  80

Gly Gln Glu Pro Gly Ala Pro His Gly Glu Pro His Gly Ala Pro His
                   85                  90                  95

Gly Glu Pro His Gly Ala Pro Gln Gly Gln Glu Pro Gly Gln Glu Pro
               100                 105                 110

Gly Gln Glu Pro Gly Gln Ala Pro Gly Gln Glu Pro Gly Glu His Pro
           115                 120                 125

Gly Ala Pro Gln Gly Ala Pro Gln Gly Gln Glu Pro Gly Ala Pro Gln
           130                 135                 140

Gly Gln Glu Pro Gly Ala Pro His Gly Glu His Pro Gly Glu His Pro
145                 150                 155                 160

Gly Gln Glu Pro Gly Ala Pro His Gly Glu Pro His Gly Ala Pro His
               165                 170                 175

Gly Glu Pro His Gly Ala Pro Gln Gly Gln Glu Pro Gly Gln Glu Pro
               180                 185                 190

Gly Gln Glu Pro Gly Gln Ala Pro
           195                 200

<210> SEQ ID NO 22
<211> LENGTH: 200
<212> TYPE: PRT
<213> ORGANISM: Artificial Sequence
<220> FEATURE:
<223> OTHER INFORMATION: C-terminal extension [(GHEPGQHP)25] of the
      A-chain of the analogue of Ex. No. 24.

```
<400> SEQUENCE: 22

Gly His Glu Pro Gly Gln His Pro Gly His Glu Pro Gly Gln His Pro
1               5                   10                  15

Gly His Glu Pro Gly Gln His Pro Gly His Glu Pro Gly Gln His Pro
            20                  25                  30

Gly His Glu Pro Gly Gln His Pro Gly His Glu Pro Gly Gln His Pro
        35                  40                  45

Gly His Glu Pro Gly Gln His Pro Gly His Glu Pro Gly Gln His Pro
    50                  55                  60

Gly His Glu Pro Gly Gln His Pro Gly His Glu Pro Gly Gln His Pro
65                  70                  75                  80

Gly His Glu Pro Gly Gln His Pro Gly His Glu Pro Gly Gln His Pro
                85                  90                  95

Gly His Glu Pro Gly Gln His Pro Gly His Glu Pro Gly Gln His Pro
            100                 105                 110

Gly His Glu Pro Gly Gln His Pro Gly His Glu Pro Gly Gln His Pro
        115                 120                 125

Gly His Glu Pro Gly Gln His Pro Gly His Glu Pro Gly Gln His Pro
    130                 135                 140

Gly His Glu Pro Gly Gln His Pro Gly His Glu Pro Gly Gln His Pro
145                 150                 155                 160

Gly His Glu Pro Gly Gln His Pro Gly His Glu Pro Gly Gln His Pro
                165                 170                 175

Gly His Glu Pro Gly Gln His Pro Gly His Glu Pro Gly Gln His Pro
            180                 185                 190

Gly His Glu Pro Gly Gln His Pro
        195                 200

<210> SEQ ID NO 23
<211> LENGTH: 200
<212> TYPE: PRT
<213> ORGANISM: Artificial Sequence
<220> FEATURE:
<223> OTHER INFORMATION: C-terminal extension [(GQEPGQHP)25] of the
      A-chain of the analogue of Ex. No. 25.

<400> SEQUENCE: 23

Gly Gln Glu Pro Gly Gln His Pro Gly Gln Glu Pro Gly Gln His Pro
1               5                   10                  15

Gly Gln Glu Pro Gly Gln His Pro Gly Gln Glu Pro Gly Gln His Pro
            20                  25                  30

Gly Gln Glu Pro Gly Gln His Pro Gly Gln Glu Pro Gly Gln His Pro
        35                  40                  45

Gly Gln Glu Pro Gly Gln His Pro Gly Gln Glu Pro Gly Gln His Pro
    50                  55                  60

Gly Gln Glu Pro Gly Gln His Pro Gly Gln Glu Pro Gly Gln His Pro
65                  70                  75                  80

Gly Gln Glu Pro Gly Gln His Pro Gly Gln Glu Pro Gly Gln His Pro
                85                  90                  95

Gly Gln Glu Pro Gly Gln His Pro Gly Gln Glu Pro Gly Gln His Pro
            100                 105                 110

Gly Gln Glu Pro Gly Gln His Pro Gly Gln Glu Pro Gly Gln His Pro
        115                 120                 125

Gly Gln Glu Pro Gly Gln His Pro Gly Gln Glu Pro Gly Gln His Pro
    130                 135                 140
```

```
Gly Gln Glu Pro Gly Gln His Pro Gly Gln Glu Pro Gly Gln His Pro
145                 150                 155                 160

Gly Gln Glu Pro Gly Gln His Pro Gly Gln Glu Pro Gly Gln His Pro
                165                 170                 175

Gly Gln Glu Pro Gly Gln His Pro Gly Gln Glu Pro Gly Gln His Pro
        180                 185                 190

Gly Gln Glu Pro Gly Gln His Pro
        195                 200

<210> SEQ ID NO 24
<211> LENGTH: 200
<212> TYPE: PRT
<213> ORGANISM: Artificial Sequence
<220> FEATURE:
<223> OTHER INFORMATION: C-terminal extension [(GQPE)50] of the A-chain
      of the analogue of Ex. No. 32.

<400> SEQUENCE: 24

Gly Gln Pro Glu Gly Gln Pro Glu Gly Gln Pro Glu Gly Gln Pro Glu
1               5                   10                  15

Gly Gln Pro Glu Gly Gln Pro Glu Gly Gln Pro Glu Gly Gln Pro Glu
            20                  25                  30

Gly Gln Pro Glu Gly Gln Pro Glu Gly Gln Pro Glu Gly Gln Pro Glu
        35                  40                  45

Gly Gln Pro Glu Gly Gln Pro Glu Gly Gln Pro Glu Gly Gln Pro Glu
50                  55                  60

Gly Gln Pro Glu Gly Gln Pro Glu Gly Gln Pro Glu Gly Gln Pro Glu
65                  70                  75                  80

Gly Gln Pro Glu Gly Gln Pro Glu Gly Gln Pro Glu Gly Gln Pro Glu
                85                  90                  95

Gly Gln Pro Glu Gly Gln Pro Glu Gly Gln Pro Glu Gly Gln Pro Glu
            100                 105                 110

Gly Gln Pro Glu Gly Gln Pro Glu Gly Gln Pro Glu Gly Gln Pro Glu
        115                 120                 125

Gly Gln Pro Glu Gly Gln Pro Glu Gly Gln Pro Glu Gly Gln Pro Glu
    130                 135                 140

Gly Gln Pro Glu Gly Gln Pro Glu Gly Gln Pro Glu Gly Gln Pro Glu
145                 150                 155                 160

Gly Gln Pro Glu Gly Gln Pro Glu Gly Gln Pro Glu Gly Gln Pro Glu
                165                 170                 175

Gly Gln Pro Glu Gly Gln Pro Glu Gly Gln Pro Glu Gly Gln Pro Glu
            180                 185                 190

Gly Gln Pro Glu Gly Gln Pro Glu
        195                 200

<210> SEQ ID NO 25
<211> LENGTH: 200
<212> TYPE: PRT
<213> ORGANISM: Artificial Sequence
<220> FEATURE:
<223> OTHER INFORMATION: C-terminal extension [(GEQP)50] of the A-chain
      of the analogue of Ex. No. 33.

<400> SEQUENCE: 25

Gly Glu Gln Pro Gly Glu Gln Pro Gly Glu Gln Pro Gly Glu Gln Pro
1               5                   10                  15

Gly Glu Gln Pro Gly Glu Gln Pro Gly Glu Gln Pro Gly Glu Gln Pro
            20                  25                  30
```

Gly Glu Gln Pro Gly Glu Gln Pro Gly Glu Gln Pro
         35                  40                  45

Gly Glu Gln Pro Gly Glu Gln Pro Gly Glu Gln Pro
 50                  55                  60

Gly Glu Gln Pro Gly Glu Gln Pro Gly Glu Gln Pro
 65                  70                  75                  80

Gly Glu Gln Pro Gly Glu Gln Pro Gly Glu Gln Pro
                 85                  90                  95

Gly Glu Gln Pro Gly Glu Gln Pro Gly Glu Gln Pro
                100                 105                 110

Gly Glu Gln Pro Gly Glu Gln Pro Gly Glu Gln Pro
                115                 120                 125

Gly Glu Gln Pro Gly Glu Gln Pro Gly Glu Gln Pro
                130                 135                 140

Gly Glu Gln Pro Gly Glu Gln Pro Gly Glu Gln Pro
145                 150                 155                 160

Gly Glu Gln Pro Gly Glu Gln Pro Gly Glu Gln Pro
                165                 170                 175

Gly Glu Gln Pro Gly Glu Gln Pro Gly Glu Gln Pro
                180                 185                 190

Gly Glu Gln Pro Gly Glu Gln Pro
        195                 200

<210> SEQ ID NO 26
<211> LENGTH: 200
<212> TYPE: PRT
<213> ORGANISM: Artificial Sequence
<220> FEATURE:
<223> OTHER INFORMATION: C-terminal extension [(GEPQ)50] of the A-chain
      of the analogue of Ex. No. 34.

<400> SEQUENCE: 26

Gly Glu Pro Gln Gly Glu Pro Gln Gly Glu Pro Gln Gly Glu Pro Gln
1               5                   10                  15

Gly Glu Pro Gln Gly Glu Pro Gln Gly Glu Pro Gln Gly Glu Pro Gln
            20                  25                  30

Gly Glu Pro Gln Gly Glu Pro Gln Gly Glu Pro Gln Gly Glu Pro Gln
        35                  40                  45

Gly Glu Pro Gln Gly Glu Pro Gln Gly Glu Pro Gln Gly Glu Pro Gln
 50                  55                  60

Gly Glu Pro Gln Gly Glu Pro Gln Gly Glu Pro Gln Gly Glu Pro Gln
65                  70                  75                  80

Gly Glu Pro Gln Gly Glu Pro Gln Gly Glu Pro Gln Gly Glu Pro Gln
                85                  90                  95

Gly Glu Pro Gln Gly Glu Pro Gln Gly Glu Pro Gln Gly Glu Pro Gln
               100                 105                 110

Gly Glu Pro Gln Gly Glu Pro Gln Gly Glu Pro Gln Gly Glu Pro Gln
           115                 120                 125

Gly Glu Pro Gln Gly Glu Pro Gln Gly Glu Pro Gln Gly Glu Pro Gln
       130                 135                 140

Gly Glu Pro Gln Gly Glu Pro Gln Gly Glu Pro Gln Gly Glu Pro Gln
145                 150                 155                 160

Gly Glu Pro Gln Gly Glu Pro Gln Gly Glu Pro Gln Gly Glu Pro Gln
                165                 170                 175

Gly Glu Pro Gln Gly Glu Pro Gln Gly Glu Pro Gln Gly Glu Pro Gln
               180                 185                 190

Gly Glu Pro Gln Gly Glu Pro Gln
        195                 200

<210> SEQ ID NO 27
<211> LENGTH: 200
<212> TYPE: PRT
<213> ORGANISM: Artificial Sequence
<220> FEATURE:
<223> OTHER INFORMATION: C-terminal extension [(GPEQ)50] of the A-chain
      of the analogue of Ex. No. 35.

<400> SEQUENCE: 27

Gly Pro Glu Gln Gly Pro Glu Gln Gly Pro Glu Gln Gly Pro Glu Gln
1               5                   10                  15

Gly Pro Glu Gln Gly Pro Glu Gln Gly Pro Glu Gln Gly Pro Glu Gln
            20                  25                  30

Gly Pro Glu Gln Gly Pro Glu Gln Gly Pro Glu Gln Gly Pro Glu Gln
        35                  40                  45

Gly Pro Glu Gln Gly Pro Glu Gln Gly Pro Glu Gln Gly Pro Glu Gln
    50                  55                  60

Gly Pro Glu Gln Gly Pro Glu Gln Gly Pro Glu Gln Gly Pro Glu Gln
65                  70                  75                  80

Gly Pro Glu Gln Gly Pro Glu Gln Gly Pro Glu Gln Gly Pro Glu Gln
                85                  90                  95

Gly Pro Glu Gln Gly Pro Glu Gln Gly Pro Glu Gln Gly Pro Glu Gln
            100                 105                 110

Gly Pro Glu Gln Gly Pro Glu Gln Gly Pro Glu Gln Gly Pro Glu Gln
        115                 120                 125

Gly Pro Glu Gln Gly Pro Glu Gln Gly Pro Glu Gln Gly Pro Glu Gln
    130                 135                 140

Gly Pro Glu Gln Gly Pro Glu Gln Gly Pro Glu Gln Gly Pro Glu Gln
145                 150                 155                 160

Gly Pro Glu Gln Gly Pro Glu Gln Gly Pro Glu Gln Gly Pro Glu Gln
                165                 170                 175

Gly Pro Glu Gln Gly Pro Glu Gln Gly Pro Glu Gln Gly Pro Glu Gln
            180                 185                 190

Gly Pro Glu Gln Gly Pro Glu Gln
        195                 200

<210> SEQ ID NO 28
<211> LENGTH: 200
<212> TYPE: PRT
<213> ORGANISM: Artificial Sequence
<220> FEATURE:
<223> OTHER INFORMATION: C-terminal extension [(GPQE)50] of the A-chain
      of the analogue of Ex. No. 36.

<400> SEQUENCE: 28

Gly Pro Gln Glu Gly Pro Gln Glu Gly Pro Gln Glu Gly Pro Gln Glu
1               5                   10                  15

Gly Pro Gln Glu Gly Pro Gln Glu Gly Pro Gln Glu Gly Pro Gln Glu
            20                  25                  30

Gly Pro Gln Glu Gly Pro Gln Glu Gly Pro Gln Glu Gly Pro Gln Glu
        35                  40                  45

Gly Pro Gln Glu Gly Pro Gln Glu Gly Pro Gln Glu Gly Pro Gln Glu
    50                  55                  60

Gly Pro Gln Glu Gly Pro Gln Glu Gly Pro Gln Glu Gly Pro Gln Glu
65                  70                  75                  80

```
Gly Pro Gln Glu Gly Pro Gln Glu Gly Pro Gln Glu
            85                  90                  95

Gly Pro Gln Glu Gly Pro Gln Glu Gly Pro Gln Glu
           100                 105                 110

Gly Pro Gln Glu Gly Pro Gln Glu Gly Pro Gln Glu
           115                 120                 125

Gly Pro Gln Glu Gly Pro Gln Glu Gly Pro Gln Glu
           130                 135                 140

Gly Pro Gln Glu Gly Pro Gln Glu Gly Pro Gln Glu
145                 150                 155                 160

Gly Pro Gln Glu Gly Pro Gln Glu Gly Pro Gln Glu
           165                 170                 175

Gly Pro Gln Glu Gly Pro Gln Glu Gly Pro Gln Glu
           180                 185                 190

Gly Pro Gln Glu Gly Pro Gln Glu
           195                 200

<210> SEQ ID NO 29
<211> LENGTH: 200
<212> TYPE: PRT
<213> ORGANISM: Artificial Sequence
<220> FEATURE:
<223> OTHER INFORMATION: C-terminal extension [(GQPA)50] of the A-chain
      of the analogue of Ex. No. 37.

<400> SEQUENCE: 29

Gly Gln Pro Ala Gly Gln Pro Ala Gly Gln Pro Ala Gly Gln Pro Ala
1               5                   10                  15

Gly Gln Pro Ala Gly Gln Pro Ala Gly Gln Pro Ala Gly Gln Pro Ala
            20                  25                  30

Gly Gln Pro Ala Gly Gln Pro Ala Gly Gln Pro Ala Gly Gln Pro Ala
        35                  40                  45

Gly Gln Pro Ala Gly Gln Pro Ala Gly Gln Pro Ala Gly Gln Pro Ala
    50                  55                  60

Gly Gln Pro Ala Gly Gln Pro Ala Gly Gln Pro Ala Gly Gln Pro Ala
65                  70                  75                  80

Gly Gln Pro Ala Gly Gln Pro Ala Gly Gln Pro Ala Gly Gln Pro Ala
            85                  90                  95

Gly Gln Pro Ala Gly Gln Pro Ala Gly Gln Pro Ala Gly Gln Pro Ala
           100                 105                 110

Gly Gln Pro Ala Gly Gln Pro Ala Gly Gln Pro Ala Gly Gln Pro Ala
           115                 120                 125

Gly Gln Pro Ala Gly Gln Pro Ala Gly Gln Pro Ala Gly Gln Pro Ala
           130                 135                 140

Gly Gln Pro Ala Gly Gln Pro Ala Gly Gln Pro Ala Gly Gln Pro Ala
145                 150                 155                 160

Gly Gln Pro Ala Gly Gln Pro Ala Gly Gln Pro Ala Gly Gln Pro Ala
           165                 170                 175

Gly Gln Pro Ala Gly Gln Pro Ala Gly Gln Pro Ala Gly Gln Pro Ala
           180                 185                 190

Gly Gln Pro Ala Gly Gln Pro Ala
           195                 200

<210> SEQ ID NO 30
<211> LENGTH: 200
<212> TYPE: PRT
```

```
<213> ORGANISM: Artificial Sequence
<220> FEATURE:
<223> OTHER INFORMATION: C-terminal extension [(GAQP)50] of the A-chain
      of the analogue of Ex. No. 38.

<400> SEQUENCE: 30

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

Gly Ala Gln Pro Gly Ala Gln Pro Gly Ala Gln Pro Gly Ala Gln Pro
            85                  90                  95

Gly Ala Gln Pro Gly Ala Gln Pro Gly Ala Gln Pro Gly Ala Gln Pro
            100                 105                 110

Gly Ala Gln Pro Gly Ala Gln Pro Gly Ala Gln Pro Gly Ala Gln Pro
        115                 120                 125

Gly Ala Gln Pro Gly Ala Gln Pro Gly Ala Gln Pro Gly Ala Gln Pro
    130                 135                 140

Gly Ala Gln Pro Gly Ala Gln Pro Gly Ala Gln Pro Gly Ala Gln Pro
145                 150                 155                 160

Gly Ala Gln Pro Gly Ala Gln Pro Gly Ala Gln Pro Gly Ala Gln Pro
            165                 170                 175

Gly Ala Gln Pro Gly Ala Gln Pro Gly Ala Gln Pro Gly Ala Gln Pro
        180                 185                 190

Gly Ala Gln Pro Gly Ala Gln Pro
        195                 200

<210> SEQ ID NO 31
<211> LENGTH: 200
<212> TYPE: PRT
<213> ORGANISM: Artificial Sequence
<220> FEATURE:
<223> OTHER INFORMATION: C-terminal extension [(GPAQ)50] of the A-chain
      of the analogue of Ex. No. 39.

<400> SEQUENCE: 31

Gly Pro Ala Gln Gly Pro Ala Gln Gly Pro Ala Gln Gly Pro Ala Gln
1               5                   10                  15

Gly Pro Ala Gln Gly Pro Ala Gln Gly Pro Ala Gln Gly Pro Ala Gln
            20                  25                  30

Gly Pro Ala Gln Gly Pro Ala Gln Gly Pro Ala Gln Gly Pro Ala Gln
        35                  40                  45

Gly Pro Ala Gln Gly Pro Ala Gln Gly Pro Ala Gln Gly Pro Ala Gln
    50                  55                  60

Gly Pro Ala Gln Gly Pro Ala Gln Gly Pro Ala Gln Gly Pro Ala Gln
65                  70                  75                  80

Gly Pro Ala Gln Gly Pro Ala Gln Gly Pro Ala Gln Gly Pro Ala Gln
                85                  90                  95

Gly Pro Ala Gln Gly Pro Ala Gln Gly Pro Ala Gln Gly Pro Ala Gln
            100                 105                 110

Gly Pro Ala Gln Gly Pro Ala Gln Gly Pro Ala Gln Gly Pro Ala Gln
```

```
                       115                 120                 125

Gly Pro Ala Gln Gly Pro Ala Gln Gly Pro Ala Gln Gly Pro Ala Gln
            130                 135                 140

Gly Pro Ala Gln Gly Pro Ala Gln Gly Pro Ala Gln Gly Pro Ala Gln
145                 150                 155                 160

Gly Pro Ala Gln Gly Pro Ala Gln Gly Pro Ala Gln Gly Pro Ala Gln
                165                 170                 175

Gly Pro Ala Gln Gly Pro Ala Gln Gly Pro Ala Gln Gly Pro Ala Gln
            180                 185                 190

Gly Pro Ala Gln Gly Pro Ala Gln
        195                 200

<210> SEQ ID NO 32
<211> LENGTH: 200
<212> TYPE: PRT
<213> ORGANISM: Artificial Sequence
<220> FEATURE:
<223> OTHER INFORMATION: C-terminal extension [(GPQA)50] of the A-chain
      of the analogue of Ex. No. 40.

<400> SEQUENCE: 32

Gly Pro Gln Ala Gly Pro Gln Ala Gly Pro Gln Ala Gly Pro Gln Ala
1               5                   10                  15

Gly Pro Gln Ala Gly Pro Gln Ala Gly Pro Gln Ala Gly Pro Gln Ala
            20                  25                  30

Gly Pro Gln Ala Gly Pro Gln Ala Gly Pro Gln Ala Gly Pro Gln Ala
        35                  40                  45

Gly Pro Gln Ala Gly Pro Gln Ala Gly Pro Gln Ala Gly Pro Gln Ala
    50                  55                  60

Gly Pro Gln Ala Gly Pro Gln Ala Gly Pro Gln Ala Gly Pro Gln Ala
65                  70                  75                  80

Gly Pro Gln Ala Gly Pro Gln Ala Gly Pro Gln Ala Gly Pro Gln Ala
                85                  90                  95

Gly Pro Gln Ala Gly Pro Gln Ala Gly Pro Gln Ala Gly Pro Gln Ala
            100                 105                 110

Gly Pro Gln Ala Gly Pro Gln Ala Gly Pro Gln Ala Gly Pro Gln Ala
        115                 120                 125

Gly Pro Gln Ala Gly Pro Gln Ala Gly Pro Gln Ala Gly Pro Gln Ala
    130                 135                 140

Gly Pro Gln Ala Gly Pro Gln Ala Gly Pro Gln Ala Gly Pro Gln Ala
145                 150                 155                 160

Gly Pro Gln Ala Gly Pro Gln Ala Gly Pro Gln Ala Gly Pro Gln Ala
                165                 170                 175

Gly Pro Gln Ala Gly Pro Gln Ala Gly Pro Gln Ala Gly Pro Gln Ala
            180                 185                 190

Gly Pro Gln Ala Gly Pro Gln Ala
        195                 200

<210> SEQ ID NO 33
<211> LENGTH: 200
<212> TYPE: PRT
<213> ORGANISM: Artificial Sequence
<220> FEATURE:
<223> OTHER INFORMATION: C-terminal extension [(GHEP)50] of the A-chain
      of the analogue of Ex. No. 41.

<400> SEQUENCE: 33

Gly His Glu Pro Gly His Glu Pro Gly His Glu Pro Gly His Glu Pro
```

```
                1               5                  10                 15
Gly His Glu Pro Gly His Glu Pro Gly His Glu Pro Gly His Glu Pro
                20                 25                 30
Gly His Glu Pro Gly His Glu Pro Gly His Glu Pro Gly His Glu Pro
                35                 40                 45
Gly His Glu Pro Gly His Glu Pro Gly His Glu Pro Gly His Glu Pro
 50                 55                 60
Gly His Glu Pro Gly His Glu Pro Gly His Glu Pro Gly His Glu Pro
 65                 70                 75                 80
Gly His Glu Pro Gly His Glu Pro Gly His Glu Pro Gly His Glu Pro
                85                 90                 95
Gly His Glu Pro Gly His Glu Pro Gly His Glu Pro Gly His Glu Pro
                100                105                110
Gly His Glu Pro Gly His Glu Pro Gly His Glu Pro Gly His Glu Pro
                115                120                125
Gly His Glu Pro Gly His Glu Pro Gly His Glu Pro Gly His Glu Pro
                130                135                140
Gly His Glu Pro Gly His Glu Pro Gly His Glu Pro Gly His Glu Pro
 145                150                155                160
Gly His Glu Pro Gly His Glu Pro Gly His Glu Pro Gly His Glu Pro
                165                170                175
Gly His Glu Pro Gly His Glu Pro Gly His Glu Pro Gly His Glu Pro
                180                185                190
Gly His Glu Pro Gly His Glu Pro
        195                200
```

<210> SEQ ID NO 34
<211> LENGTH: 200
<212> TYPE: PRT
<213> ORGANISM: Artificial Sequence
<220> FEATURE:
<223> OTHER INFORMATION: C-terminal extension [(GHPE)50] of the A-chain
      of the analogue of Ex. No. 42.

<400> S

Gly His Pro Glu Gly His Pro Glu Gly His Pro Glu
            165                 170                 175

Gly His Pro Glu Gly His Pro Glu Gly His Pro Glu
            180                 185                 190

Gly His Pro Glu Gly His Pro Glu
        195                 200

<210> SEQ ID NO 35
<211> LENGTH: 200
<212> TYPE: PRT
<213> ORGANISM: Artificial Sequence
<220> FEATURE:
<223> OTHER INFORMATION: C-terminal extension [(GPEH)50] of the A-chain
      of the analogue of Ex. No. 43.

<400> SEQUENCE: 35

Gly Pro Glu His Gly Pro Glu His Gly Pro Glu His Gly Pro Glu His
1               5                   10                  15

Gly Pro Glu His Gly Pro Glu His Gly Pro Glu His Gly Pro Glu His
            20                  25                  30

Gly Pro Glu His Gly Pro Glu His Gly Pro Glu His Gly Pro Glu His
        35                  40                  45

Gly Pro Glu His Gly Pro Glu His Gly Pro Glu His Gly Pro Glu His
    50                  55                  60

Gly Pro Glu His Gly Pro Glu His Gly Pro Glu His Gly Pro Glu His
65                  70                  75                  80

Gly Pro Glu His Gly Pro Glu His Gly Pro Glu His Gly Pro Glu His
                85                  90                  95

Gly Pro Glu His Gly Pro Glu His Gly Pro Glu His Gly Pro Glu His
            100                 105                 110

Gly Pro Glu His Gly Pro Glu His Gly Pro Glu His Gly Pro Glu His
        115                 120                 125

Gly Pro Glu His Gly Pro Glu His Gly Pro Glu His Gly Pro Glu His
    130                 135                 140

Gly Pro Glu His Gly Pro Glu His Gly Pro Glu His Gly Pro Glu His
145                 150                 155                 160

Gly Pro Glu His Gly Pro Glu His Gly Pro Glu His Gly Pro Glu His
                165                 170                 175

Gly Pro Glu His Gly Pro Glu His Gly Pro Glu His Gly Pro Glu His
            180                 185                 190

Gly Pro Glu His Gly Pro Glu His
        195                 200

<210> SEQ ID NO 36
<211> LENGTH: 200
<212> TYPE: PRT
<213> ORGANISM: Artificial Sequence
<220> FEATURE:
<223> OTHER INFORMATION: C-terminal extension [(GPHE)50] of the A-chain
      of the analogue of Ex. No. 44.

<400> SEQUENCE: 36

Gly Pro His Glu Gly Pro His Glu Gly Pro His Glu Gly Pro His Glu
1               5                   10                  15

Gly Pro His Glu Gly Pro His Glu Gly Pro His Glu Gly Pro His Glu
            20                  25                  30

Gly Pro His Glu Gly Pro His Glu Gly Pro His Glu Gly Pro His Glu
        35                  40                  45

Gly Pro His Glu Gly Pro His Glu Gly Pro His Glu
          50                  55                  60

Gly Pro His Glu Gly Pro His Glu Gly Pro His Glu
65                  70                  75                  80

Gly Pro His Glu Gly Pro His Glu Gly Pro His Glu
          85                  90                  95

Gly Pro His Glu Gly Pro His Glu Gly Pro His Glu
          100                 105                 110

Gly Pro His Glu Gly Pro His Glu Gly Pro His Glu
          115                 120                 125

Gly Pro His Glu Gly Pro His Glu Gly Pro His Glu
          130                 135                 140

Gly Pro His Glu Gly Pro His Glu Gly Pro His Glu
145                 150                 155                 160

Gly Pro His Glu Gly Pro His Glu Gly Pro His Glu
          165                 170                 175

Gly Pro His Glu Gly Pro His Glu Gly Pro His Glu
          180                 185                 190

Gly Pro His Glu Gly Pro His Glu
          195                 200

<210> SEQ ID NO 37
<211> LENGTH: 200
<212> TYPE: PRT
<213> ORGANISM: Artificial Sequence
<220> FEATURE:
<223> OTHER INFORMATION: C-terminal extension [(GQEH)50] of the A-chain
      of the analogue of Ex. No. 45.

<400> SEQUENCE: 37

Gly Gln Glu His Gly Gln Glu His Gly Gln Glu His Gly Gln Glu His
1               5                   10                  15

Gly Gln Glu His Gly Gln Glu His Gly Gln Glu His Gly Gln Glu His
          20                  25                  30

Gly Gln Glu His Gly Gln Glu His Gly Gln Glu His Gly Gln Glu His
     35                  40                  45

Gly Gln Glu His Gly Gln Glu His Gly Gln Glu His Gly Gln Glu His
50                  55                  60

Gly Gln Glu His Gly Gln Glu His Gly Gln Glu His Gly Gln Glu His
65                  70                  75                  80

Gly Gln Glu His Gly Gln Glu His Gly Gln Glu His Gly Gln Glu His
          85                  90                  95

Gly Gln Glu His Gly Gln Glu His Gly Gln Glu His Gly Gln Glu His
          100                 105                 110

Gly Gln Glu His Gly Gln Glu His Gly Gln Glu His Gly Gln Glu His
          115                 120                 125

Gly Gln Glu His Gly Gln Glu His Gly Gln Glu His Gly Gln Glu His
          130                 135                 140

Gly Gln Glu His Gly Gln Glu His Gly Gln Glu His Gly Gln Glu His
145                 150                 155                 160

Gly Gln Glu His Gly Gln Glu His Gly Gln Glu His Gly Gln Glu His
          165                 170                 175

Gly Gln Glu His Gly Gln Glu His Gly Gln Glu His Gly Gln Glu His
          180                 185                 190

Gly Gln Glu His Gly Gln Glu His
          195                 200

<210> SEQ ID NO 38
<211> LENGTH: 200
<212> TYPE: PRT
<213> ORGANISM: Artificial Sequence
<220> FEATURE:
<223> OTHER INFORMATION: C-terminal extension [(GQHE)50] of the A-chain of the analogue of Ex. No. 46.

<400> SEQUENCE: 38

```
Gly Gln His Glu Gly Gln His Glu Gly Gln His Glu Gly Gln His Glu
1               5                   10                  15
Gly Gln His Glu Gly Gln His Glu Gly Gln His Glu Gly Gln His Glu
            20                  25                  30
Gly Gln His Glu Gly Gln His Glu Gly Gln His Glu Gly Gln His Glu
        35                  40                  45
Gly Gln His Glu Gly Gln His Glu Gly Gln His Glu Gly Gln His Glu
    50                  55                  60
Gly Gln His Glu Gly Gln His Glu Gly Gln His Glu Gly Gln His Glu
65                  70                  75                  80
Gly Gln His Glu Gly Gln His Glu Gly Gln His Glu Gly Gln His Glu
                85                  90                  95
Gly Gln His Glu Gly Gln His Glu Gly Gln His Glu Gly Gln His Glu
            100                 105                 110
Gly Gln His Glu Gly Gln His Glu Gly Gln His Glu Gly Gln His Glu
        115                 120                 125
Gly Gln His Glu Gly Gln His Glu Gly Gln His Glu Gly Gln His Glu
    130                 135                 140
Gly Gln His Glu Gly Gln His Glu Gly Gln His Glu Gly Gln His Glu
145                 150                 155                 160
Gly Gln His Glu Gly Gln His Glu Gly Gln His Glu Gly Gln His Glu
                165                 170                 175
Gly Gln His Glu Gly Gln His Glu Gly Gln His Glu Gly Gln His Glu
            180                 185                 190
Gly Gln His Glu Gly Gln His Glu
        195                 200
```

<210> SEQ ID NO 39
<211> LENGTH: 200
<212> TYPE: PRT
<213> ORGANISM: Artificial Sequence
<220> FEATURE:
<223> OTHER INFORMATION: C-terminal extension [(GHEQ)50] of the A-chain of the analogue of Ex. No. 48.

<400> SEQUENCE: 39

```
Gly His Glu Gln Gly His Glu Gln Gly His Glu Gln Gly His Glu Gln
1               5                   10                  15
Gly His Glu Gln Gly His Glu Gln Gly His Glu Gln Gly His Glu Gln
            20                  25                  30
Gly His Glu Gln Gly His Glu Gln Gly His Glu Gln Gly His Glu Gln
        35                  40                  45
Gly His Glu Gln Gly His Glu Gln Gly His Glu Gln Gly His Glu Gln
    50                  55                  60
Gly His Glu Gln Gly His Glu Gln Gly His Glu Gln Gly His Glu Gln
65                  70                  75                  80
Gly His Glu Gln Gly His Glu Gln Gly His Glu Gln Gly His Glu Gln
                85                  90                  95
```

Gly His Glu Gln Gly His Glu Gln Gly His Glu Gln
            100             105             110

Gly His Glu Gln Gly His Glu Gln Gly His Glu Gln
        115             120             125

Gly His Glu Gln Gly His Glu Gln Gly His Glu Gln
    130             135             140

Gly His Glu Gln Gly His Glu Gln Gly His Glu Gln
145             150             155             160

Gly His Glu Gln Gly His Glu Gln Gly His Glu Gln
            165             170             175

Gly His Glu Gln Gly His Glu Gln Gly His Glu Gln
        180             185             190

Gly His Glu Gln Gly His Glu Gln
    195             200

<210> SEQ ID NO 40
<211> LENGTH: 200
<212> TYPE: PRT
<213> ORGANISM: Artificial Sequence
<220> FEATURE:
<223> OTHER INFORMATION: C-terminal extension [(GHQE)50] of the A-chain
      of the analogue of Ex. No. 49.

<400> SEQUENCE: 40

Gly His Gln Glu Gly His Gln Glu Gly His Gln Glu Gly His Gln Glu
1               5                   10                  15

Gly His Gln Glu Gly His Gln Glu Gly His Gln Glu Gly His Gln Glu
            20                  25                  30

Gly His Gln Glu Gly His Gln Glu Gly His Gln Glu Gly His Gln Glu
        35                  40                  45

Gly His Gln Glu Gly His Gln Glu Gly His Gln Glu Gly His Gln Glu
    50                  55                  60

Gly His Gln Glu Gly His Gln Glu Gly His Gln Glu Gly His Gln Glu
65                  70                  75                  80

Gly His Gln Glu Gly His Gln Glu Gly His Gln Glu Gly His Gln Glu
            85                  90                  95

Gly His Gln Glu Gly His Gln Glu Gly His Gln Glu Gly His Gln Glu
        100                 105                 110

Gly His Gln Glu Gly His Gln Glu Gly His Gln Glu Gly His Gln Glu
    115                 120                 125

Gly His Gln Glu Gly His Gln Glu Gly His Gln Glu Gly His Gln Glu
130                 135                 140

Gly His Gln Glu Gly His Gln Glu Gly His Gln Glu Gly His Gln Glu
            145                 150                 155         160

Gly His Gln Glu Gly His Gln Glu Gly His Gln Glu Gly His Gln Glu
        165                 170                 175

Gly His Gln Glu Gly His Gln Glu Gly His Gln Glu Gly His Gln Glu
    180                 185                 190

Gly His Gln Glu Gly His Gln Glu
195                 200

<210> SEQ ID NO 41
<211> LENGTH: 201
<212> TYPE: PRT
<213> ORGANISM: Artificial Sequence
<220> FEATURE:
<223> OTHER INFORMATION: C-terminal extension [(GEQ)67] of the A-chain of the analogue of Ex. No. 51.

<400> SEQUENCE: 41

Gly Glu Gln Gly Glu Gln Gly Glu Gln Gly Glu Gln Gly Glu Gln Gly
1               5                   10                  15

Glu Gln Gly Glu Gln Gly Glu Gln Gly Glu Gln Gly Glu Gln Gly Glu
            20                  25                  30

Gln Gly Glu Gln Gly Glu Gln Gly Glu Gln Gly Glu Gln Gly Glu Gln
        35                  40                  45

Gly Glu Gln Gly Glu Gln Gly Glu Gln Gly Glu Gln Gly Glu Gln Gly
    50                  55                  60

Glu Gln Gly Glu Gln Gly Glu Gln Gly Glu Gln Gly Glu Gln Gly Glu
65                  70                  75                  80

Gln Gly Glu Gln Gly Glu Gln Gly Glu Gln Gly Glu Gln Gly Glu Gln
            85                  90                  95

Gly Glu Gln Gly Glu Gln Gly Glu Gln Gly Glu Gln Gly Glu Gln Gly
            100                 105                 110

Glu Gln Gly Glu Gln Gly Glu Gln Gly Glu Gln Gly Glu Gln Gly Glu
            115                 120                 125

Gln Gly Glu Gln Gly Glu Gln Gly Glu Gln Gly Glu Gln Gly Glu Gln
        130                 135                 140

Gly Glu Gln Gly Glu Gln Gly Glu Gln Gly Glu Gln Gly Glu Gln Gly
145                 150                 155                 160

Glu Gln Gly Glu Gln Gly Glu Gln Gly Glu Gln Gly Glu Gln Gly Glu
            165                 170                 175

Gln Gly Glu Gln Gly Glu Gln Gly Glu Gln Gly Glu Gln Gly Glu Gln
            180                 185                 190

Gly Glu Gln Gly Glu Gln Gly Glu Gln
        195                 200

<210> SEQ ID NO 42
<211> LENGTH: 201
<212> TYPE: PRT
<213> ORGANISM: Artificial Sequence
<220> FEATURE:
<223> OTHER INFORMATION: C-terminal extension [(GAQ)67] of the A-chain
      of the analogue of Ex. No. 52.

<400> SEQUENCE: 42

Gly Ala Gln Gly Ala Gln Gly Ala Gln Gly Ala Gln Gly Ala Gln Gly
1               5                   10                  15

Ala Gln Gly Ala Gln Gly Ala Gln Gly Ala Gln Gly Ala Gln Gly Ala
            20                  25                  30

Gln Gly Ala Gln Gly Ala Gln Gly Ala Gln Gly Ala Gln Gly Ala Gln
        35                  40                  45

Gly Ala Gln Gly Ala Gln Gly Ala Gln Gly Ala Gln Gly Ala Gln Gly
    50                  55                  60

Ala Gln Gly Ala Gln Gly Ala Gln Gly Ala Gln Gly Ala Gln Gly Ala
65                  70                  75                  80

Gln Gly Ala Gln Gly Ala Gln Gly Ala Gln Gly Ala Gln Gly Ala Gln
            85                  90                  95

Gly Ala Gln Gly Ala Gln Gly Ala Gln Gly Ala Gln Gly Ala Gln Gly
            100                 105                 110

Ala Gln Gly Ala Gln Gly Ala Gln Gly Ala Gln Gly Ala Gln Gly Ala
            115                 120                 125

Gln Gly Ala Gln Gly Ala Gln Gly Ala Gln Gly Ala Gln Gly Ala Gln

```
                    130                 135                 140

Gly Ala Gln Gly Ala Gln Gly Ala Gln Gly Ala Gln Gly Ala Gln Gly
145                 150                 155                 160

Ala Gln Gly Ala Gln Gly Ala Gln Gly Ala Gln Gly Ala Gln Gly Ala
                165                 170                 175

Gln Gly Ala Gln Gly Ala Gln Gly Ala Gln Gly Ala Gln Gly Ala Gln
            180                 185                 190

Gly Ala Gln Gly Ala Gln Gly Ala Gln
        195                 200

<210> SEQ ID NO 43
<211> LENGTH: 248
<212> TYPE: PRT
<213> ORGANISM: Artificial Sequence
<220> FEATURE:
<223> OTHER INFORMATION: C-terminal extension [(GQAP)62] of the A-chain
      of the analogue of Ex. No. 53.

<400> SEQUENCE: 43

Gly Gln Ala Pro Gly Gln Ala Pro Gly Gln Ala Pro Gly Gln Ala Pro
1               5                   10                  15

Gly Gln Ala Pro Gly Gln Ala Pro Gly Gln Ala Pro Gly Gln Ala Pro
            20                  25                  30

Gly Gln Ala Pro Gly Gln Ala Pro Gly Gln Ala Pro Gly Gln Ala Pro
        35                  40                  45

Gly Gln Ala Pro Gly Gln Ala Pro Gly Gln Ala Pro Gly Gln Ala Pro
    50                  55                  60

Gly Gln Ala Pro Gly Gln Ala Pro Gly Gln Ala Pro Gly Gln Ala Pro
65                  70                  75                  80

Gly Gln Ala Pro Gly Gln Ala Pro Gly Gln Ala Pro Gly Gln Ala Pro
                85                  90                  95

Gly Gln Ala Pro Gly Gln Ala Pro Gly Gln Ala Pro Gly Gln Ala Pro
            100                 105                 110

Gly Gln Ala Pro Gly Gln Ala Pro Gly Gln Ala Pro Gly Gln Ala Pro
        115                 120                 125

Gly Gln Ala Pro Gly Gln Ala Pro Gly Gln Ala Pro Gly Gln Ala Pro
    130                 135                 140

Gly Gln Ala Pro Gly Gln Ala Pro Gly Gln Ala Pro Gly Gln Ala Pro
145                 150                 155                 160

Gly Gln Ala Pro Gly Gln Ala Pro Gly Gln Ala Pro Gly Gln Ala Pro
                165                 170                 175

Gly Gln Ala Pro Gly Gln Ala Pro Gly Gln Ala Pro Gly Gln Ala Pro
            180                 185                 190

Gly Gln Ala Pro Gly Gln Ala Pro Gly Gln Ala Pro Gly Gln Ala Pro
        195                 200                 205

Gly Gln Ala Pro Gly Gln Ala Pro Gly Gln Ala Pro Gly Gln Ala Pro
    210                 215                 220

Gly Gln Ala Pro Gly Gln Ala Pro Gly Gln Ala Pro Gly Gln Ala Pro
225                 230                 235                 240

Gly Gln Ala Pro Gly Gln Ala Pro
                245

<210> SEQ ID NO 44
<211> LENGTH: 300
<212> TYPE: PRT
<213> ORGANISM: Artificial Sequence
<220> FEATURE:
```

<223> OTHER INFORMATION: C-terminal extension [(GQAP)75] of the A-chain
of the analogue of Ex. Nos. 54 and 60.

<400> SEQUENCE: 44

Gly Gln Ala Pro Gly Gln Ala Pro Gly Gln Ala Pro Gly Gln Ala Pro
1               5                   10                  15

Gly Gln Ala Pro Gly Gln Ala Pro Gly Gln Ala Pro Gly Gln Ala Pro
                20                  25                  30

Gly Gln Ala Pro Gly Gln Ala Pro Gly Gln Ala Pro Gly Gln Ala Pro
            35                  40                  45

Gly Gln Ala Pro Gly Gln Ala Pro Gly Gln Ala Pro Gly Gln Ala Pro
        50                  55                  60

Gly Gln Ala Pro Gly Gln Ala Pro Gly Gln Ala Pro Gly Gln Ala Pro
65                  70                  75                  80

Gly Gln Ala Pro Gly Gln Ala Pro Gly Gln Ala Pro Gly Gln Ala Pro
                85                  90                  95

Gly Gln Ala Pro Gly Gln Ala Pro Gly Gln Ala Pro Gly Gln Ala Pro
            100                 105                 110

Gly Gln Ala Pro Gly Gln Ala Pro Gly Gln Ala Pro Gly Gln Ala Pro
        115                 120                 125

Gly Gln Ala Pro Gly Gln Ala Pro Gly Gln Ala Pro Gly Gln Ala Pro
    130                 135                 140

Gly Gln Ala Pro Gly Gln Ala Pro Gly Gln Ala Pro Gly Gln Ala Pro
145                 150                 155                 160

Gly Gln Ala Pro Gly Gln Ala Pro Gly Gln Ala Pro Gly Gln Ala Pro
                165                 170                 175

Gly Gln Ala Pro Gly Gln Ala Pro Gly Gln Ala Pro Gly Gln Ala Pro
            180                 185                 190

Gly Gln Ala Pro Gly Gln Ala Pro Gly Gln Ala Pro Gly Gln Ala Pro
        195                 200                 205

Gly Gln Ala Pro Gly Gln Ala Pro Gly Gln Ala Pro Gly Gln Ala Pro
    210                 215                 220

Gly Gln Ala Pro Gly Gln Ala Pro Gly Gln Ala Pro Gly Gln Ala Pro
225                 230                 235                 240

Gly Gln Ala Pro Gly Gln Ala Pro Gly Gln Ala Pro Gly Gln Ala Pro
                245                 250                 255

Gly Gln Ala Pro Gly Gln Ala Pro Gly Gln Ala Pro Gly Gln Ala Pro
            260                 265                 270

Gly Gln Ala Pro Gly Gln Ala Pro Gly Gln Ala Pro Gly Gln Ala Pro
        275                 280                 285

Gly Gln Ala Pro Gly Gln Ala Pro Gly Gln Ala Pro
    290                 295                 300

<210> SEQ ID NO 45
<211> LENGTH: 400
<212> TYPE: PRT
<213> ORGANISM: Artificial Sequence
<220> FEATURE:
<223> OTHER INFORMATION: C-terminal extension [(GQAP)100] of the A-chain
of the analogue of Ex. Nos. 55 and 63.

<400> SEQUENCE: 45

Gly Gln Ala Pro Gly Gln Ala Pro Gly Gln Ala Pro Gly Gln Ala Pro
1               5                   10                  15

Gly Gln Ala Pro Gly Gln Ala Pro Gly Gln Ala Pro Gly Gln Ala Pro
                20                  25                  30

```
Gly Gln Ala Pro Gly Gln Ala Pro Gly Gln Ala Pro Gly Gln Ala Pro
            35                  40                  45
Gly Gln Ala Pro Gly Gln Ala Pro Gly Gln Ala Pro Gly Gln Ala Pro
50                  55                  60
Gly Gln Ala Pro Gly Gln Ala Pro Gly Gln Ala Pro Gly Gln Ala Pro
65                  70                  75                  80
Gly Gln Ala Pro Gly Gln Ala Pro Gly Gln Ala Pro Gly Gln Ala Pro
            85                  90                  95
Gly Gln Ala Pro Gly Gln Ala Pro Gly Gln Ala Pro Gly Gln Ala Pro
            100                 105                 110
Gly Gln Ala Pro Gly Gln Ala Pro Gly Gln Ala Pro Gly Gln Ala Pro
            115                 120                 125
Gly Gln Ala Pro Gly Gln Ala Pro Gly Gln Ala Pro Gly Gln Ala Pro
            130                 135                 140
Gly Gln Ala Pro Gly Gln Ala Pro Gly Gln Ala Pro Gly Gln Ala Pro
145                 150                 155                 160
Gly Gln Ala Pro Gly Gln Ala Pro Gly Gln Ala Pro Gly Gln Ala Pro
            165                 170                 175
Gly Gln Ala Pro Gly Gln Ala Pro Gly Gln Ala Pro Gly Gln Ala Pro
            180                 185                 190
Gly Gln Ala Pro Gly Gln Ala Pro Gly Gln Ala Pro Gly Gln Ala Pro
            195                 200                 205
Gly Gln Ala Pro Gly Gln Ala Pro Gly Gln Ala Pro Gly Gln Ala Pro
            210                 215                 220
Gly Gln Ala Pro Gly Gln Ala Pro Gly Gln Ala Pro Gly Gln Ala Pro
225                 230                 235                 240
Gly Gln Ala Pro Gly Gln Ala Pro Gly Gln Ala Pro Gly Gln Ala Pro
            245                 250                 255
Gly Gln Ala Pro Gly Gln Ala Pro Gly Gln Ala Pro Gly Gln Ala Pro
            260                 265                 270
Gly Gln Ala Pro Gly Gln Ala Pro Gly Gln Ala Pro Gly Gln Ala Pro
            275                 280                 285
Gly Gln Ala Pro Gly Gln Ala Pro Gly Gln Ala Pro Gly Gln Ala Pro
            290                 295                 300
Gly Gln Ala Pro Gly Gln Ala Pro Gly Gln Ala Pro Gly Gln Ala Pro
305                 310                 315                 320
Gly Gln Ala Pro Gly Gln Ala Pro Gly Gln Ala Pro Gly Gln Ala Pro
            325                 330                 335
Gly Gln Ala Pro Gly Gln Ala Pro Gly Gln Ala Pro Gly Gln Ala Pro
            340                 345                 350
Gly Gln Ala Pro Gly Gln Ala Pro Gly Gln Ala Pro Gly Gln Ala Pro
            355                 360                 365
Gly Gln Ala Pro Gly Gln Ala Pro Gly Gln Ala Pro Gly Gln Ala Pro
            370                 375                 380
Gly Gln Ala Pro Gly Gln Ala Pro Gly Gln Ala Pro Gly Gln Ala Pro
385                 390                 395                 400

<210> SEQ ID NO 46
<211> LENGTH: 500
<212> TYPE: PRT
<213> ORGANISM: Artificial Sequence
<220> FEATURE:
<223> OTHER INFORMATION: C-terminal extension [(GQAP)125] of the A-chain
      of the analogue of Ex. No. 57.

<400> SEQUENCE: 46
```

Gly Gln Ala Pro Gly Gln Ala Pro Gly Gln Ala Pro Gly Gln Ala Pro
1               5                   10                  15

Gly Gln Ala Pro Gly Gln Ala Pro Gly Gln Ala Pro Gly Gln Ala Pro
            20                  25                  30

Gly Gln Ala Pro Gly Gln Ala Pro Gly Gln Ala Pro Gly Gln Ala Pro
            35                  40                  45

Gly Gln Ala Pro Gly Gln Ala Pro Gly Gln Ala Pro Gly Gln Ala Pro
50                  55                  60

Gly Gln Ala Pro Gly Gln Ala Pro Gly Gln Ala Pro Gly Gln Ala Pro
65              70                  75                  80

Gly Gln Ala Pro Gly Gln Ala Pro Gly Gln Ala Pro Gly Gln Ala Pro
            85                  90                  95

Gly Gln Ala Pro Gly Gln Ala Pro Gly Gln Ala Pro Gly Gln Ala Pro
            100                 105                 110

Gly Gln Ala Pro Gly Gln Ala Pro Gly Gln Ala Pro Gly Gln Ala Pro
            115                 120                 125

Gly Gln Ala Pro Gly Gln Ala Pro Gly Gln Ala Pro Gly Gln Ala Pro
130                 135                 140

Gly Gln Ala Pro Gly Gln Ala Pro Gly Gln Ala Pro Gly Gln Ala Pro
145             150                 155                 160

Gly Gln Ala Pro Gly Gln Ala Pro Gly Gln Ala Pro Gly Gln Ala Pro
            165                 170                 175

Gly Gln Ala Pro Gly Gln Ala Pro Gly Gln Ala Pro Gly Gln Ala Pro
            180                 185                 190

Gly Gln Ala Pro Gly Gln Ala Pro Gly Gln Ala Pro Gly Gln Ala Pro
            195                 200                 205

Gly Gln Ala Pro Gly Gln Ala Pro Gly Gln Ala Pro Gly Gln Ala Pro
210                 215                 220

Gly Gln Ala Pro Gly Gln Ala Pro Gly Gln Ala Pro Gly Gln Ala Pro
225                 230                 235                 240

Gly Gln Ala Pro Gly Gln Ala Pro Gly Gln Ala Pro Gly Gln Ala Pro
            245                 250                 255

Gly Gln Ala Pro Gly Gln Ala Pro Gly Gln Ala Pro Gly Gln Ala Pro
            260                 265                 270

Gly Gln Ala Pro Gly Gln Ala Pro Gly Gln Ala Pro Gly Gln Ala Pro
            275                 280                 285

Gly Gln Ala Pro Gly Gln Ala Pro Gly Gln Ala Pro Gly Gln Ala Pro
            290                 295                 300

Gly Gln Ala Pro Gly Gln Ala Pro Gly Gln Ala Pro Gly Gln Ala Pro
305                 310                 315                 320

Gly Gln Ala Pro Gly Gln Ala Pro Gly Gln Ala Pro Gly Gln Ala Pro
            325                 330                 335

Gly Gln Ala Pro Gly Gln Ala Pro Gly Gln Ala Pro Gly Gln Ala Pro
            340                 345                 350

Gly Gln Ala Pro Gly Gln Ala Pro Gly Gln Ala Pro Gly Gln Ala Pro
            355                 360                 365

Gly Gln Ala Pro Gly Gln Ala Pro Gly Gln Ala Pro Gly Gln Ala Pro
            370                 375                 380

Gly Gln Ala Pro Gly Gln Ala Pro Gly Gln Ala Pro Gly Gln Ala Pro
385                 390                 395                 400

Gly Gln Ala Pro Gly Gln Ala Pro Gly Gln Ala Pro Gly Gln Ala Pro
            405                 410                 415

```
Gly Gln Ala Pro Gly Gln Ala Pro Gly Gln Ala Pro Gly Gln Ala Pro
            420                 425                 430

Gly Gln Ala Pro Gly Gln Ala Pro Gly Gln Ala Pro Gly Gln Ala Pro
            435                 440                 445

Gly Gln Ala Pro Gly Gln Ala Pro Gly Gln Ala Pro Gly Gln Ala Pro
            450                 455                 460

Gly Gln Ala Pro Gly Gln Ala Pro Gly Gln Ala Pro Gly Gln Ala Pro
465                 470                 475                 480

Gly Gln Ala Pro Gly Gln Ala Pro Gly Gln Ala Pro Gly Gln Ala Pro
            485                 490                 495

Gly Gln Ala Pro
            500

<210> SEQ ID NO 47
<211> LENGTH: 600
<212> TYPE: PRT
<213> ORGANISM: Artificial Sequence
<220> FEATURE:
<223> OTHER INFORMATION: C-terminal extension [(GQAP)150] of the A-chain
      of the analogue of Ex. Nos. 58 and 61.

<400> SEQUENCE: 47

Gly Gln Ala Pro Gly Gln Ala Pro Gly Gln Ala Pro Gly Gln Ala Pro
1               5                   10                  15

Gly Gln Ala Pro Gly Gln Ala Pro Gly Gln Ala Pro Gly Gln Ala Pro
            20                  25                  30

Gly Gln Ala Pro Gly Gln Ala Pro Gly Gln Ala Pro Gly Gln Ala Pro
            35                  40                  45

Gly Gln Ala Pro Gly Gln Ala Pro Gly Gln Ala Pro Gly Gln Ala Pro
            50                  55                  60

Gly Gln Ala Pro Gly Gln Ala Pro Gly Gln Ala Pro Gly Gln Ala Pro
65                  70                  75                  80

Gly Gln Ala Pro Gly Gln Ala Pro Gly Gln Ala Pro Gly Gln Ala Pro
            85                  90                  95

Gly Gln Ala Pro Gly Gln Ala Pro Gly Gln Ala Pro Gly Gln Ala Pro
            100                 105                 110

Gly Gln Ala Pro Gly Gln Ala Pro Gly Gln Ala Pro Gly Gln Ala Pro
            115                 120                 125

Gly Gln Ala Pro Gly Gln Ala Pro Gly Gln Ala Pro Gly Gln Ala Pro
            130                 135                 140

Gly Gln Ala Pro Gly Gln Ala Pro Gly Gln Ala Pro Gly Gln Ala Pro
145                 150                 155                 160

Gly Gln Ala Pro Gly Gln Ala Pro Gly Gln Ala Pro Gly Gln Ala Pro
            165                 170                 175

Gly Gln Ala Pro Gly Gln Ala Pro Gly Gln Ala Pro Gly Gln Ala Pro
            180                 185                 190

Gly Gln Ala Pro Gly Gln Ala Pro Gly Gln Ala Pro Gly Gln Ala Pro
            195                 200                 205

Gly Gln Ala Pro Gly Gln Ala Pro Gly Gln Ala Pro Gly Gln Ala Pro
            210                 215                 220

Gly Gln Ala Pro Gly Gln Ala Pro Gly Gln Ala Pro Gly Gln Ala Pro
225                 230                 235                 240

Gly Gln Ala Pro Gly Gln Ala Pro Gly Gln Ala Pro Gly Gln Ala Pro
            245                 250                 255

Gly Gln Ala Pro Gly Gln Ala Pro Gly Gln Ala Pro Gly Gln Ala Pro
            260                 265                 270
```

Gly Gln Ala Pro Gly Gln Ala Pro Gly Gln Ala Pro Gly Gln Ala Pro
        275                 280                 285

Gly Gln Ala Pro Gly Gln Ala Pro Gly Gln Ala Pro Gly Gln Ala Pro
    290                 295                 300

Gly Gln Ala Pro Gly Gln Ala Pro Gly Gln Ala Pro Gly Gln Ala Pro
305                 310                 315                 320

Gly Gln Ala Pro Gly Gln Ala Pro Gly Gln Ala Pro Gly Gln Ala Pro
            325                 330                 335

Gly Gln Ala Pro Gly Gln Ala Pro Gly Gln Ala Pro Gly Gln Ala Pro
        340                 345                 350

Gly Gln Ala Pro Gly Gln Ala Pro Gly Gln Ala Pro Gly Gln Ala Pro
    355                 360                 365

Gly Gln Ala Pro Gly Gln Ala Pro Gly Gln Ala Pro Gly Gln Ala Pro
370                 375                 380

Gly Gln Ala Pro Gly Gln Ala Pro Gly Gln Ala Pro Gly Gln Ala Pro
385                 390                 395                 400

Gly Gln Ala Pro Gly Gln Ala Pro Gly Gln Ala Pro Gly Gln Ala Pro
            405                 410                 415

Gly Gln Ala Pro Gly Gln Ala Pro Gly Gln Ala Pro Gly Gln Ala Pro
        420                 425                 430

Gly Gln Ala Pro Gly Gln Ala Pro Gly Gln Ala Pro Gly Gln Ala Pro
    435                 440                 445

Gly Gln Ala Pro Gly Gln Ala Pro Gly Gln Ala Pro Gly Gln Ala Pro
450                 455                 460

Gly Gln Ala Pro Gly Gln Ala Pro Gly Gln Ala Pro Gly Gln Ala Pro
465                 470                 475                 480

Gly Gln Ala Pro Gly Gln Ala Pro Gly Gln Ala Pro Gly Gln Ala Pro
            485                 490                 495

Gly Gln Ala Pro Gly Gln Ala Pro Gly Gln Ala Pro Gly Gln Ala Pro
        500                 505                 510

Gly Gln Ala Pro Gly Gln Ala Pro Gly Gln Ala Pro Gly Gln Ala Pro
    515                 520                 525

Gly Gln Ala Pro Gly Gln Ala Pro Gly Gln Ala Pro Gly Gln Ala Pro
530                 535                 540

Gly Gln Ala Pro Gly Gln Ala Pro Gly Gln Ala Pro Gly Gln Ala Pro
545                 550                 555                 560

Gly Gln Ala Pro Gly Gln Ala Pro Gly Gln Ala Pro Gly Gln Ala Pro
            565                 570                 575

Gly Gln Ala Pro Gly Gln Ala Pro Gly Gln Ala Pro Gly Gln Ala Pro
        580                 585                 590

Gly Gln Ala Pro Gly Gln Ala Pro
    595                 600

<210> SEQ ID NO 48
<211> LENGTH: 199
<212> TYPE: PRT
<213> ORGANISM: Artificial Sequence
<220> FEATURE:
<223> OTHER INFORMATION: C-terminal extension [APQ(GAPQ)49] of the
      A-chain of the analogue of Ex. No. 64.

<400> SEQUENCE: 48

Ala Pro Gln Gly Ala Pro Gln Gly Ala Pro Gln Gly Ala Pro Gln Gly
1               5                   10                  15

Ala Pro Gln Gly Ala Pro Gln Gly Ala Pro Gln Gly Ala Pro Gln Gly

```
                    20                  25                  30
Ala Pro Gln Gly Ala Pro Gln Gly Ala Pro Gln Gly Ala Pro Gln Gly
            35                  40                  45
Ala Pro Gln Gly Ala Pro Gln Gly Ala Pro Gln Gly Ala Pro Gln Gly
    50                  55                  60
Ala Pro Gln Gly Ala Pro Gln Gly Ala Pro Gln Gly Ala Pro Gln Gly
65                  70                  75                  80
Ala Pro Gln Gly Ala Pro Gln Gly Ala Pro Gln Gly Ala Pro Gln Gly
                85                  90                  95
Ala Pro Gln Gly Ala Pro Gln Gly Ala Pro Gln Gly Ala Pro Gln Gly
            100                 105                 110
Ala Pro Gln Gly Ala Pro Gln Gly Ala Pro Gln Gly Ala Pro Gln Gly
        115                 120                 125
Ala Pro Gln Gly Ala Pro Gln Gly Ala Pro Gln Gly Ala Pro Gln Gly
    130                 135                 140
Ala Pro Gln Gly Ala Pro Gln Gly Ala Pro Gln Gly Ala Pro Gln Gly
145                 150                 155                 160
Ala Pro Gln Gly Ala Pro Gln Gly Ala Pro Gln Gly Ala Pro Gln Gly
                165                 170                 175
Ala Pro Gln Gly Ala Pro Gln Gly Ala Pro Gln Gly Ala Pro Gln Gly
            180                 185                 190

Ala Pro Gln Gly Ala Pro Gln
        195

<210> SEQ ID NO 49
<211> LENGTH: 199
<212> TYPE: PRT
<213> ORGANISM: Artificial Sequence
<220> FEATURE:
<223> OTHER INFORMATION: C-terminal extension [APQ(GAQP)49] of the
      A-chain of the analogue of Ex. No. 65.

<400> SEQUENCE: 49

Ala Gln Pro Gly Ala Gln Pro Gly Ala Gln Pro Gly Ala Gln Pro Gly
1               5                   10                  15
Ala Gln Pro Gly Ala Gln Pro Gly Ala Gln Pro Gly Ala Gln Pro Gly
            20                  25                  30
Ala Gln Pro Gly Ala Gln Pro Gly Ala Gln Pro Gly Ala Gln Pro Gly
        35                  40                  45
Ala Gln Pro Gly Ala Gln Pro Gly Ala Gln Pro Gly Ala Gln Pro Gly
    50                  55                  60
Ala Gln Pro Gly Ala Gln Pro Gly Ala Gln Pro Gly Ala Gln Pro Gly
65                  70                  75                  80
Ala Gln Pro Gly Ala Gln Pro Gly Ala Gln Pro Gly Ala Gln Pro Gly
                85                  90                  95
Ala Gln Pro Gly Ala Gln Pro Gly Ala Gln Pro Gly Ala Gln Pro Gly
            100                 105                 110
Ala Gln Pro Gly Ala Gln Pro Gly Ala Gln Pro Gly Ala Gln Pro Gly
        115                 120                 125
Ala Gln Pro Gly Ala Gln Pro Gly Ala Gln Pro Gly Ala Gln Pro Gly
    130                 135                 140
Ala Gln Pro Gly Ala Gln Pro Gly Ala Gln Pro Gly Ala Gln Pro Gly
145                 150                 155                 160
Ala Gln Pro Gly Ala Gln Pro Gly Ala Gln Pro Gly Ala Gln Pro Gly
                165                 170                 175
```

```
Ala Gln Pro Gly Ala Gln Pro Gly Ala Gln Pro Gly Ala Gln Pro Gly
            180                 185                 190

Ala Gln Pro Gly Ala Gln Pro
        195
```

<210> SEQ ID NO 50
<211> LENGTH: 199
<212> TYPE: PRT
<213> ORGANISM: Artificial Sequence
<220> FEATURE:
<223> OTHER INFORMATION: C-terminal extension [QAP(GQAP)49] of the
    A-chain of the analogue of Ex. No. 66.

<400> SEQUENCE: 50

```
Gln Ala Pro Gly Gln Ala Pro Gly Gln Ala Pro Gly Gln Ala Pro Gly
1               5                   10                  15

Gln Ala Pro Gly Gln Ala Pro Gly Gln Ala Pro Gly Gln Ala Pro Gly
            20                  25                  30

Gln Ala Pro Gly Gln Ala Pro Gly Gln Ala Pro Gly Gln Ala Pro Gly
        35                  40                  45

Gln Ala Pro Gly Gln Ala Pro Gly Gln Ala Pro Gly Gln Ala Pro Gly
    50                  55                  60

Gln Ala Pro Gly Gln Ala Pro Gly Gln Ala Pro Gly Gln Ala Pro Gly
65                  70                  75                  80

Gln Ala Pro Gly Gln Ala Pro Gly Gln Ala Pro Gly Gln Ala Pro Gly
                85                  90                  95

Gln Ala Pro Gly Gln Ala Pro Gly Gln Ala Pro Gly Gln Ala Pro Gly
            100                 105                 110

Gln Ala Pro Gly Gln Ala Pro Gly Gln Ala Pro Gly Gln Ala Pro Gly
        115                 120                 125

Gln Ala Pro Gly Gln Ala Pro Gly Gln Ala Pro Gly Gln Ala Pro Gly
    130                 135                 140

Gln Ala Pro Gly Gln Ala Pro Gly Gln Ala Pro Gly Gln Ala Pro Gly
145                 150                 155                 160

Gln Ala Pro Gly Gln Ala Pro Gly Gln Ala Pro Gly Gln Ala Pro Gly
                165                 170                 175

Gln Ala Pro Gly Gln Ala Pro Gly Gln Ala Pro Gly Gln Ala Pro Gly
            180                 185                 190

Gln Ala Pro Gly Gln Ala Pro
        195
```

<210> SEQ ID NO 51
<211> LENGTH: 199
<212> TYPE: PRT
<213> ORGANISM: Artificial Sequence
<220> FEATURE:
<223> OTHER INFORMATION: C-terminal extension [QPA(GQPA)49] of the
    A-chain of the analogue of Ex. No. 67.

<400> SEQUENCE: 51

```
Gln Pro Ala Gly Gln Pro Ala Gly Gln Pro Ala Gly Gln Pro Ala Gly
1               5                   10                  15

Gln Pro Ala Gly Gln Pro Ala Gly Gln Pro Ala Gly Gln Pro Ala Gly
            20                  25                  30

Gln Pro Ala Gly Gln Pro Ala Gly Gln Pro Ala Gly Gln Pro Ala Gly
        35                  40                  45

Gln Pro Ala Gly Gln Pro Ala Gly Gln Pro Ala Gly Gln Pro Ala Gly
    50                  55                  60
```

Gln Pro Ala Gly Gln Pro Ala Gly Gln Pro Ala Gly Gln Pro Ala Gly
65                  70                  75                  80

Gln Pro Ala Gly Gln Pro Ala Gly Gln Pro Ala Gly Gln Pro Ala Gly
                85                  90                  95

Gln Pro Ala Gly Gln Pro Ala Gly Gln Pro Ala Gly Gln Pro Ala Gly
            100                 105                 110

Gln Pro Ala Gly Gln Pro Ala Gly Gln Pro Ala Gly Gln Pro Ala Gly
        115                 120                 125

Gln Pro Ala Gly Gln Pro Ala Gly Gln Pro Ala Gly Gln Pro Ala Gly
    130                 135                 140

Gln Pro Ala Gly Gln Pro Ala Gly Gln Pro Ala Gly Gln Pro Ala Gly
145                 150                 155                 160

Gln Pro Ala Gly Gln Pro Ala Gly Gln Pro Ala Gly Gln Pro Ala Gly
                165                 170                 175

Gln Pro Ala Gly Gln Pro Ala Gly Gln Pro Ala Gly Gln Pro Ala Gly
            180                 185                 190

Gln Pro Ala Gly Gln Pro Ala
        195

<210> SEQ ID NO 52
<211> LENGTH: 199
<212> TYPE: PRT
<213> ORGANISM: Artificial Sequence
<220> FEATURE:
<223> OTHER INFORMATION: C-terminal extension [PAQ(GPAQ)49] of the
      A-chain of the analogue of Ex. No. 68.

<400> SEQUENCE: 52

Pro Ala Gln Gly Pro Ala Gln Gly Pro Ala Gln Gly Pro Ala Gln Gly
1               5                   10                  15

Pro Ala Gln Gly Pro Ala Gln Gly Pro Ala Gln Gly Pro Ala Gln Gly
            20                  25                  30

Pro Ala Gln Gly Pro Ala Gln Gly Pro Ala Gln Gly Pro Ala Gln Gly
        35                  40                  45

Pro Ala Gln Gly Pro Ala Gln Gly Pro Ala Gln Gly Pro Ala Gln Gly
    50                  55                  60

Pro Ala Gln Gly Pro Ala Gln Gly Pro Ala Gln Gly Pro Ala Gln Gly
65                  70                  75                  80

Pro Ala Gln Gly Pro Ala Gln Gly Pro Ala Gln Gly Pro Ala Gln Gly
                85                  90                  95

Pro Ala Gln Gly Pro Ala Gln Gly Pro Ala Gln Gly Pro Ala Gln Gly
            100                 105                 110

Pro Ala Gln Gly Pro Ala Gln Gly Pro Ala Gln Gly Pro Ala Gln Gly
        115                 120                 125

Pro Ala Gln Gly Pro Ala Gln Gly Pro Ala Gln Gly Pro Ala Gln Gly
    130                 135                 140

Pro Ala Gln Gly Pro Ala Gln Gly Pro Ala Gln Gly Pro Ala Gln Gly
145                 150                 155                 160

Pro Ala Gln Gly Pro Ala Gln Gly Pro Ala Gln Gly Pro Ala Gln Gly
                165                 170                 175

Pro Ala Gln Gly Pro Ala Gln Gly Pro Ala Gln Gly Pro Ala Gln Gly
            180                 185                 190

Pro Ala Gln Gly Pro Ala Gln
        195

<210> SEQ ID NO 53

```
<211> LENGTH: 199
<212> TYPE: PRT
<213> ORGANISM: Artificial Sequence
<220> FEATURE:
<223> OTHER INFORMATION: C-terminal extension [PQA(GPQA)49] of the
      A-chain of the analogue of Ex. No. 69.

<400> SEQUENCE: 53

Pro Gln Ala Gly Pro Gln Ala Gly Pro Gln Ala Gly Pro Gln Ala Gly
1               5                   10                  15

Pro Gln Ala Gly Pro Gln Ala Gly Pro Gln Ala Gly Pro Gln Ala Gly
            20                  25                  30

Pro Gln Ala Gly Pro Gln Ala Gly Pro Gln Ala Gly Pro Gln Ala Gly
        35                  40                  45

Pro Gln Ala Gly Pro Gln Ala Gly Pro Gln Ala Gly Pro Gln Ala Gly
    50                  55                  60

Pro Gln Ala Gly Pro Gln Ala Gly Pro Gln Ala Gly Pro Gln Ala Gly
65                  70                  75                  80

Pro Gln Ala Gly Pro Gln Ala Gly Pro Gln Ala Gly Pro Gln Ala Gly
                85                  90                  95

Pro Gln Ala Gly Pro Gln Ala Gly Pro Gln Ala Gly Pro Gln Ala Gly
            100                 105                 110

Pro Gln Ala Gly Pro Gln Ala Gly Pro Gln Ala Gly Pro Gln Ala Gly
        115                 120                 125

Pro Gln Ala Gly Pro Gln Ala Gly Pro Gln Ala Gly Pro Gln Ala Gly
    130                 135                 140

Pro Gln Ala Gly Pro Gln Ala Gly Pro Gln Ala Gly Pro Gln Ala Gly
145                 150                 155                 160

Pro Gln Ala Gly Pro Gln Ala Gly Pro Gln Ala Gly Pro Gln Ala Gly
                165                 170                 175

Pro Gln Ala Gly Pro Gln Ala Gly Pro Gln Ala Gly Pro Gln Ala Gly
            180                 185                 190

Pro Gln Ala Gly Pro Gln Ala
        195

<210> SEQ ID NO 54
<211> LENGTH: 224
<212> TYPE: PRT
<213> ORGANISM: Artificial Sequence
<220> FEATURE:
<223> OTHER INFORMATION: C-terminal extension [(GQAP)56] of the A-chain
      of the analogue of Ex. No. 70.

<400> SEQUENCE: 54

Gly Gln Ala Pro Gly Gln Ala Pro Gly Gln Ala Pro Gly Gln Ala Pro
1               5                   10                  15

Gly Gln Ala Pro Gly Gln Ala Pro Gly Gln Ala Pro Gly Gln Ala Pro
            20                  25                  30

Gly Gln Ala Pro Gly Gln Ala Pro Gly Gln Ala Pro Gly Gln Ala Pro
        35                  40                  45

Gly Gln Ala Pro Gly Gln Ala Pro Gly Gln Ala Pro Gly Gln Ala Pro
    50                  55                  60

Gly Gln Ala Pro Gly Gln Ala Pro Gly Gln Ala Pro Gly Gln Ala Pro
65                  70                  75                  80

Gly Gln Ala Pro Gly Gln Ala Pro Gly Gln Ala Pro Gly Gln Ala Pro
                85                  90                  95

Gly Gln Ala Pro Gly Gln Ala Pro Gly Gln Ala Pro Gly Gln Ala Pro
            100                 105                 110
```

Gly Gln Ala Pro Gly Gln Ala Pro Gly Gln Ala Pro Gly Gln Ala Pro
        115                 120                 125

Gly Gln Ala Pro Gly Gln Ala Pro Gly Gln Ala Pro Gly Gln Ala Pro
        130                 135                 140

Gly Gln Ala Pro Gly Gln Ala Pro Gly Gln Ala Pro Gly Gln Ala Pro
145                 150                 155                 160

Gly Gln Ala Pro Gly Gln Ala Pro Gly Gln Ala Pro Gly Gln Ala Pro
        165                 170                 175

Gly Gln Ala Pro Gly Gln Ala Pro Gly Gln Ala Pro Gly Gln Ala Pro
        180                 185                 190

Gly Gln Ala Pro Gly Gln Ala Pro Gly Gln Ala Pro Gly Gln Ala Pro
        195                 200                 205

Gly Gln Ala Pro Gly Gln Ala Pro Gly Gln Ala Pro Gly Gln Ala Pro
        210                 215                 220

<210> SEQ ID NO 55
<211> LENGTH: 276
<212> TYPE: PRT
<213> ORGANISM: Artificial Sequence
<220> FEATURE:
<223> OTHER INFORMATION: C-terminal extension [(GQAP)69] of the A-chain
      of the analogue of Ex. No. 71.

<400> SEQUENCE: 55

Gly Gln Ala Pro Gly Gln Ala Pro Gly Gln Ala Pro Gly Gln Ala Pro
1               5                   10                  15

Gly Gln Ala Pro Gly Gln Ala Pro Gly Gln Ala Pro Gly Gln Ala Pro
        20                  25                  30

Gly Gln Ala Pro Gly Gln Ala Pro Gly Gln Ala Pro Gly Gln Ala Pro
        35                  40                  45

Gly Gln Ala Pro Gly Gln Ala Pro Gly Gln Ala Pro Gly Gln Ala Pro
        50                  55                  60

Gly Gln Ala Pro Gly Gln Ala Pro Gly Gln Ala Pro Gly Gln Ala Pro
65                  70                  75                  80

Gly Gln Ala Pro Gly Gln Ala Pro Gly Gln Ala Pro Gly Gln Ala Pro
        85                  90                  95

Gly Gln Ala Pro Gly Gln Ala Pro Gly Gln Ala Pro Gly Gln Ala Pro
        100                 105                 110

Gly Gln Ala Pro Gly Gln Ala Pro Gly Gln Ala Pro Gly Gln Ala Pro
        115                 120                 125

Gly Gln Ala Pro Gly Gln Ala Pro Gly Gln Ala Pro Gly Gln Ala Pro
        130                 135                 140

Gly Gln Ala Pro Gly Gln Ala Pro Gly Gln Ala Pro Gly Gln Ala Pro
145                 150                 155                 160

Gly Gln Ala Pro Gly Gln Ala Pro Gly Gln Ala Pro Gly Gln Ala Pro
        165                 170                 175

Gly Gln Ala Pro Gly Gln Ala Pro Gly Gln Ala Pro Gly Gln Ala Pro
        180                 185                 190

Gly Gln Ala Pro Gly Gln Ala Pro Gly Gln Ala Pro Gly Gln Ala Pro
        195                 200                 205

Gly Gln Ala Pro Gly Gln Ala Pro Gly Gln Ala Pro Gly Gln Ala Pro
        210                 215                 220

Gly Gln Ala Pro Gly Gln Ala Pro Gly Gln Ala Pro Gly Gln Ala Pro
225                 230                 235                 240

Gly Gln Ala Pro Gly Gln Ala Pro Gly Gln Ala Pro Gly Gln Ala Pro

```
                245                 250                 255
Gly Gln Ala Pro Gly Gln Ala Pro Gly Gln Ala Pro Gly Gln Ala Pro
            260                 265                 270
Gly Gln Ala Pro
        275

<210> SEQ ID NO 56
<211> LENGTH: 124
<212> TYPE: PRT
<213> ORGANISM: Artificial Sequence
<220> FEATURE:
<223> OTHER INFORMATION: C-terminal extension [(GQAP)31] of the A-chain
      of the analogue of Ex. No. 72.

<400> SEQUENCE: 56

Gly Gln Ala Pro Gly Gln Ala Pro Gly Gln Ala Pro Gly Gln Ala Pro
1               5                   10                  15
Gly Gln Ala Pro Gly Gln Ala Pro Gly Gln Ala Pro Gly Gln Ala Pro
            20                  25                  30
Gly Gln Ala Pro Gly Gln Ala Pro Gly Gln Ala Pro Gly Gln Ala Pro
        35                  40                  45
Gly Gln Ala Pro Gly Gln Ala Pro Gly Gln Ala Pro Gly Gln Ala Pro
    50                  55                  60
Gly Gln Ala Pro Gly Gln Ala Pro Gly Gln Ala Pro Gly Gln Ala Pro
65                  70                  75                  80
Gly Gln Ala Pro Gly Gln Ala Pro Gly Gln Ala Pro Gly Gln Ala Pro
                85                  90                  95
Gly Gln Ala Pro Gly Gln Ala Pro Gly Gln Ala Pro Gly Gln Ala Pro
            100                 105                 110
Gly Gln Ala Pro Gly Gln Ala Pro Gly Gln Ala Pro
        115                 120

<210> SEQ ID NO 57
<211> LENGTH: 148
<212> TYPE: PRT
<213> ORGANISM: Artificial Sequence
<220> FEATURE:
<223> OTHER INFORMATION: C-terminal extension [(GQAP)37] of the A-chain
      of the analogue of Ex. No. 73.

<400> SEQUENCE: 57

Gly Gln Ala Pro Gly Gln Ala Pro Gly Gln Ala Pro Gly Gln Ala Pro
1               5                   10                  15
Gly Gln Ala Pro Gly Gln Ala Pro Gly Gln Ala Pro Gly Gln Ala Pro
            20                  25                  30
Gly Gln Ala Pro Gly Gln Ala Pro Gly Gln Ala Pro Gly Gln Ala Pro
        35                  40                  45
Gly Gln Ala Pro Gly Gln Ala Pro Gly Gln Ala Pro Gly Gln Ala Pro
    50                  55                  60
Gly Gln Ala Pro Gly Gln Ala Pro Gly Gln Ala Pro Gly Gln Ala Pro
65                  70                  75                  80
Gly Gln Ala Pro Gly Gln Ala Pro Gly Gln Ala Pro Gly Gln Ala Pro
                85                  90                  95
Gly Gln Ala Pro Gly Gln Ala Pro Gly Gln Ala Pro Gly Gln Ala Pro
            100                 105                 110
Gly Gln Ala Pro Gly Gln Ala Pro Gly Gln Ala Pro Gly Gln Ala Pro
        115                 120                 125
Gly Gln Ala Pro Gly Gln Ala Pro Gly Gln Ala Pro Gly Gln Ala Pro
```

Gly Gln Ala Pro
145

<210> SEQ ID NO 58
<211> LENGTH: 176
<212> TYPE: PRT
<213> ORGANISM: Artificial Sequence
<220> FEATURE:
<223> OTHER INFORMATION: C-terminal extension [(GQAP)44] of the A-chain
      of the analogue of Ex. No. 74.

<400> SEQUENCE: 58

Gly Gln Ala Pro Gly Gln Ala Pro Gly Gln Ala Pro Gly Gln Ala Pro
1               5                   10                  15

Gly Gln Ala Pro Gly Gln Ala Pro Gly Gln Ala Pro Gly Gln Ala Pro
            20                  25                  30

Gly Gln Ala Pro Gly Gln Ala Pro Gly Gln Ala Pro Gly Gln Ala Pro
        35                  40                  45

Gly Gln Ala Pro Gly Gln Ala Pro Gly Gln Ala Pro Gly Gln Ala Pro
    50                  55                  60

Gly Gln Ala Pro Gly Gln Ala Pro Gly Gln Ala Pro Gly Gln Ala Pro
65                  70                  75                  80

Gly Gln Ala Pro Gly Gln Ala Pro Gly Gln Ala Pro Gly Gln Ala Pro
                85                  90                  95

Gly Gln Ala Pro Gly Gln Ala Pro Gly Gln Ala Pro Gly Gln Ala Pro
            100                 105                 110

Gly Gln Ala Pro Gly Gln Ala Pro Gly Gln Ala Pro Gly Gln Ala Pro
        115                 120                 125

Gly Gln Ala Pro Gly Gln Ala Pro Gly Gln Ala Pro Gly Gln Ala Pro
    130                 135                 140

Gly Gln Ala Pro Gly Gln Ala Pro Gly Gln Ala Pro Gly Gln Ala Pro
145                 150                 155                 160

Gly Gln Ala Pro Gly Gln Ala Pro Gly Gln Ala Pro Gly Gln Ala Pro
                165                 170                 175

<210> SEQ ID NO 59
<211> LENGTH: 200
<212> TYPE: PRT
<213> ORGANISM: Artificial Sequence
<220> FEATURE:
<223> OTHER INFORMATION: C-terminal extension [QP(GQP)66] of the A-chain
      of the analogue of Ex. No. 75.

<400> SEQUENCE: 59

Gln Pro Gly Gln Pro Gly Gln Pro Gly Gln Pro Gly Gln Pro Gly Gln
1               5                   10                  15

Pro Gly Gln Pro Gly Gln Pro Gly Gln Pro Gly Gln Pro Gly Gln Pro
            20                  25                  30

Gly Gln Pro Gly Gln Pro Gly Gln Pro Gly Gln Pro Gly Gln Pro Gly
        35                  40                  45

Gln Pro Gly Gln Pro Gly Gln Pro Gly Gln Pro Gly Gln Pro Gly Gln
    50                  55                  60

Pro Gly Gln Pro Gly Gln Pro Gly Gln Pro Gly Gln Pro Gly Gln Pro
65                  70                  75                  80

Gly Gln Pro Gly Gln Pro Gly Gln Pro Gly Gln Pro Gly Gln Pro Gly
                85                  90                  95

Gln Pro Gly Gln Pro Gly Gln Pro Gly Gln Pro Gly Gln Pro Gly Gln

-continued

```
                100                 105                 110
Pro Gly Gln Pro Gly Gln Pro Gly Gln Pro Gly Gln Pro
            115                 120                 125
Gly Gln Pro Gly Gln Pro Gly Gln Pro Gly Gln Pro Gly
            130                 135                 140
Gln Pro Gly Gln Pro Gly Gln Pro Gly Gln Pro Gly Gln
145                 150                 155                 160
Pro Gly Gln Pro Gly Gln Pro Gly Gln Pro Gly Gln Pro
                165                 170                 175
Gly Gln Pro Gly Gln Pro Gly Gln Pro Gly Gln Pro Gly
            180                 185                 190
Gln Pro Gly Gln Pro Gly Gln Pro
        195                 200

<210> SEQ ID NO 60
<211> LENGTH: 151
<212> TYPE: PRT
<213> ORGANISM: Artificial Sequence
<220> FEATURE:
<223> OTHER INFORMATION: C-terminal extension [AQP(GAQP)37] of the
      A-chain of the analogue of Ex. No. 76.

<400> SEQUENCE: 60

Ala Gln Pro Gly Ala Gln Pro Gly Ala Gln Pro Gly Ala Gln Pro Gly
1               5                   10                  15
Ala Gln Pro Gly Ala Gln Pro Gly Ala Gln Pro Gly Ala Gln Pro Gly
            20                  25                  30
Ala Gln Pro Gly Ala Gln Pro Gly Ala Gln Pro Gly Ala Gln Pro Gly
        35                  40                  45
Ala Gln Pro Gly Ala Gln Pro Gly Ala Gln Pro Gly Ala Gln Pro Gly
    50                  55                  60
Ala Gln Pro Gly Ala Gln Pro Gly Ala Gln Pro Gly Ala Gln Pro Gly
65                  70                  75                  80
Ala Gln Pro Gly Ala Gln Pro Gly Ala Gln Pro Gly Ala Gln Pro Gly
                85                  90                  95
Ala Gln Pro Gly Ala Gln Pro Gly Ala Gln Pro Gly Ala Gln Pro Gly
            100                 105                 110
Ala Gln Pro Gly Ala Gln Pro Gly Ala Gln Pro Gly Ala Gln Pro Gly
        115                 120                 125
Ala Gln Pro Gly Ala Gln Pro Gly Ala Gln Pro Gly Ala Gln Pro Gly
    130                 135                 140
Ala Gln Pro Gly Ala Gln Pro
145                 150

<210> SEQ ID NO 61
<211> LENGTH: 251
<212> TYPE: PRT
<213> ORGANISM: Artificial Sequence
<220> FEATURE:
<223> OTHER INFORMATION: C-terminal extension [AQP(GAQP)62] of the
      A-chain of the analogue of Ex. No. 77.

<400> SEQUENCE: 61

Ala Gln Pro Gly Ala Gln Pro Gly Ala Gln Pro Gly Ala Gln Pro Gly
1               5                   10                  15
Ala Gln Pro Gly Ala Gln Pro Gly Ala Gln Pro Gly Ala Gln Pro Gly
            20                  25                  30
Ala Gln Pro Gly Ala Gln Pro Gly Ala Gln Pro Gly Ala Gln Pro Gly
```

```
                    35                  40                  45
Ala Gln Pro Gly Ala Gln Pro Gly Ala Gln Pro Gly Ala Gln Pro Gly
 50                  55                  60
Ala Gln Pro Gly Ala Gln Pro Gly Ala Gln Pro Gly Ala Gln Pro Gly
 65                  70                  75                  80
Ala Gln Pro Gly Ala Gln Pro Gly Ala Gln Pro Gly Ala Gln Pro Gly
                    85                  90                  95
Ala Gln Pro Gly Ala Gln Pro Gly Ala Gln Pro Gly Ala Gln Pro Gly
                100                 105                 110
Ala Gln Pro Gly Ala Gln Pro Gly Ala Gln Pro Gly Ala Gln Pro Gly
                115                 120                 125
Ala Gln Pro Gly Ala Gln Pro Gly Ala Gln Pro Gly Ala Gln Pro Gly
            130                 135                 140
Ala Gln Pro Gly Ala Gln Pro Gly Ala Gln Pro Gly Ala Gln Pro Gly
145                 150                 155                 160
Ala Gln Pro Gly Ala Gln Pro Gly Ala Gln Pro Gly Ala Gln Pro Gly
                165                 170                 175
Ala Gln Pro Gly Ala Gln Pro Gly Ala Gln Pro Gly Ala Gln Pro Gly
                180                 185                 190
Ala Gln Pro Gly Ala Gln Pro Gly Ala Gln Pro Gly Ala Gln Pro Gly
            195                 200                 205
Ala Gln Pro Gly Ala Gln Pro Gly Ala Gln Pro Gly Ala Gln Pro Gly
 210                 215                 220
Ala Gln Pro Gly Ala Gln Pro Gly Ala Gln Pro Gly Ala Gln Pro Gly
225                 230                 235                 240
Ala Gln Pro Gly Ala Gln Pro Gly Ala Gln Pro
                245                 250

<210> SEQ ID NO 62
<211> LENGTH: 262
<212> TYPE: PRT
<213> ORGANISM: Artificial Sequence
<220> FEATURE:
<223> OTHER INFORMATION: synthetic

<400> SEQUENCE: 62

Glu Glu Ala Glu Ala Glu Ala Pro Lys Phe Val Asn Gln His Leu Cys
 1               5                  10                  15
Gly Ser His Leu Val Glu Ala Leu Tyr Leu Val Cys Gly Glu Arg Gly
                20                  25                  30
Phe Phe Tyr Thr Pro Lys Asp Met Lys Gly Ile Val Glu Gln Cys Cys
            35                  40                  45
Thr Ser Ile Cys Ser Leu Tyr Gln Leu Glu Asn Tyr Cys Gln Gly Ala
 50                  55                  60
Pro Gln Gly Ala Pro Gln Gly Ala Pro Gln Gly Ala Pro Gln Gly Ala
 65                  70                  75                  80
Pro Gln Gly Ala Pro Gln Gly Ala Pro Gln Gly Ala Pro Gln Gly Ala
                85                  90                  95
Pro Gln Gly Ala Pro Gln Gly Ala Pro Gln Gly Ala Pro Gln Gly Ala
                100                 105                 110
Pro Gln Gly Ala Pro Gln Gly Ala Pro Gln Gly Ala Pro Gln Gly Ala
            115                 120                 125
Pro Gln Gly Ala Pro Gln Gly Ala Pro Gln Gly Ala Pro Gln Gly Ala
        130                 135                 140
Pro Gln Gly Ala Pro Gln Gly Ala Pro Gln Gly Ala Pro Gln Gly Ala
```

```
145                 150                 155                 160
Pro Gln Gly Ala Pro Gln Gly Ala Pro Gln Gly Ala Pro Gln Gly Ala
                165                 170                 175
Pro Gln Gly Ala Pro Gln Gly Ala Pro Gln Gly Ala Pro Gln Gly Ala
            180                 185                 190
Pro Gln Gly Ala Pro Gln Gly Ala Pro Gln Gly Ala Pro Gln Gly Ala
        195                 200                 205
Pro Gln Gly Ala Pro Gln Gly Ala Pro Gln Gly Ala Pro Gln Gly Ala
    210                 215                 220
Pro Gln Gly Ala Pro Gln Gly Ala Pro Gln Gly Ala Pro Gln Gly Ala
225                 230                 235                 240
Pro Gln Gly Ala Pro Gln Gly Ala Pro Gln Gly Ala Pro Gln Gly Ala
                245                 250                 255
Pro Gln Gly Ala Pro Gln
            260
```

The invention claimed is:

1. An oligomer extended insulin or insulin analogue, wherein said insulin or insulin analogue is a two-chain insulin molecule comprising an A- and a B-chain, and is extended at the N-terminal end of the B-chain, and/or from the C-terminal end of the A-chain, with an extension consisting only of amino acid residues selected from the group consisting of His (H), Gln (Q), Ala (A), Asp (D), Glu (E), Gly (G), Pro (P), Ser (S) and Thr (T); wherein the extension comprises from about 100 to about 800 contiguous amino acids and wherein
  I) a first subset of amino acid residues in the extension are selected from the group consisting of His (H) and Gln (Q); and
  II) a second subset of amino acid residues in the extension are selected from the group consisting of Ala (A), Asp (D), Glu (E), Gly (G), Pro (P), Ser (S) and Thr (T);
  wherein the number of amino acid residues in the second subset is equal to or greater than the number of amino acid residues in the first subset,
  wherein the number of amino acid residues in the second subset is no more than three times the number of amino acid residues in the first subset,
  and wherein said insulin or insulin analogue is extended with motifs A, B, C, D and/or any combination of A, B, C and D:
  A) contiguous amino acid residues comprising amino acid residues selected from the group of [A, G, and H or Q]; or from the group of [E, G, and H or Q]; or from the group of [G, P, and H or Q]; (Group A); or
  B) contiguous amino acid residues comprising amino acid residues selected from the group of [A, G, P, and H or Q]; or from the group of [E, G, P, and H or Q]; or from the group of [G, K, P, and H or Q]; or from the group of [E, G, H, and Q]; (Group B); or
  C) contiguous amino acid residues comprising amino acid residues selected from the group of [A, G, P, H, and Q]; from the group of [E, G, P, H, and Q]; (Group C); or
  D) contiguous amino acid residues comprising amino acid residues selected from the group of [A, E, G, P, H, and Q]; or from the group of [E, G, K, P, H, and Q]; (Group D);
  wherein the motif, or combination of motifs, may be repeated as needed in order to obtain an extension of the desired length and size.

2. A pharmaceutical composition comprising a therapeutically effective amount of an oligomer extended insulin or insulin analogue according to claim 1, or a pharmaceutically acceptable salt thereof, together with one of more adjuvants, excipients, carriers and/or diluents.

3. A method of treatment or alleviation of a metabolic disease or disorder or condition of a human, comprising the step of administering to such a human in need thereof, a therapeutically effective amount of the oligomer extended insulin or insulin analogue according to claim 1, wherein said disease, disorder or condition is selected from the group consisting of diabetes, impaired glucose tolerance, hyperglycemia, dyslipidemia, obesity, metabolic syndrome X, and insulin resistance syndrome.

4. The method according to claim 3, wherein said disease, disorder or condition is Type 1 diabetes or Type 2 diabetes.

5. An oligomer extended insulin or insulin analogue wherein said insulin or insulin analogue is a two-chain insulin molecule comprising an A- and a B-chain, and is extended at the N-terminal end of the B-chain, and/or from the C-terminal end of the A-chain, with an extension consisting only of amino acid residues selected from the group consisting of His (H), Gln (Q), Ala (A), Asp (D), Glu (E), Gly (G), Pro (P), Ser (S) and Thr (T); wherein the extension comprises from about 100 to about 800 contiguous amino acids and wherein
  I) a first subset of amino acid residues in the extension are selected from the group consisting of His (H) and Gln (Q); and
  II) a second subset of amino acid residues in the extension are selected from the group consisting of Ala (A), Asp (D), Glu (E), Gly (G), Pro (P), Ser (S) and Thr (T);
  wherein the number of amino acid residues in the second subset is equal to or greater than the number of amino acid residues in the first subset,
  wherein the number of amino acid residues in the second subset is no more than three times the number of amino acid residues in the first subset,
  and wherein the insulin or insulin analogue is extended with
  a motif of Group A selected from [GAQ]; [GEH]; [GEQ]; [GQA]; [GQE]; and [GQP]; and/or any combination hereof; and/or
  a motif of Group B selected from [GAPH]; [GAPQ]; [GAQP]; [GEHP]; [GEPH]; [GEPQ]; [GEQH];

[GEQP]; [GHEP]; [GHEQ]; [GHPE]; [GHQE]; [GPAQ]; [GPEH]; [GPEQ]; [GPHE]; [GPQA]; [GPQE]; [GQAP]; [GQEH]; [GQEP]; [GQHE]; [GQPA]; and [GQPE]; and/or any combination hereof; and/or a motif of Group C selected from [GHEPGQHP]; [GQEPGQHP]; [GQAPGQAPGQAPGAPH]; and [GQAPGQAPGAPHGAPH]; and/or any combination hereof; and/or a motif of Group D selected from [GEHPGAPHGQEPGQAP]; [GQEPGQEPGQEPGAPH]; [GQEPGQEPGAPHGAPH]; and [A,E,G,P,H,Q]; and/or any combination hereof.

6. An oligomer extended insulin or insulin analogue, wherein said insulin or insulin analogue is a two-chain insulin molecule comprising an A- and a B-chain, and is extended at the N-terminal end of the B-chain, and/or from the C-terminal end of the A-chain, which is a compound of the general Formula I Ins-Ext (I)

wherein:
"Ins" represents an analogue of human insulin selected from the group consisting of
A14E,A21G*,B25H,desB30;
A21G*,desB30;
A21G,B1F*,desB30;
A21G,A22A,A23P,A24Q*,desB30;
A21G,A22A,A23Q,A24P*,desB30;
A21G,A22P,A23A,A24Q*,desB30;
A21G,A22P,A23Q,A24A*,desB30;
A21G,A22Q,A23A,A24P*,desB30;
A21G,A22Q,A23P,A24A*,desB30;
A21G,A22Q,A23P*,desB30; and
A21Q*,desB30; and "Ext" indicates an extension composed of a motif selected from the group consisting of
[GAQ]; [GEH]; [GEQ]; [GQA]; [GQE]; [GQP]; [GAPH]; [GAPQ]; [GAQP]; [GEHP]; [GEPH]; [GEPQ]; [GEQH]; [GEQP]; [GHEP]; [GHEQ]; [GHPE]; [GHQE]; [GPAQ]; [GPEH]; [GPEQ]; [GPHE]; [GPQA]; [GPQE]; [GQAP]; [GQEH]; [GQEP]; [GQHE]; [GQPA]; [GQPE]; [GHEPGQHP]; [GQEPGQHP]; [GQAPGQAPGQAPGAPH]; [GQAPGQAPGAPHGAPH]; [GEHPGAPHGQEPGQAP]; [GQEPGQEPGQEPGAPH]; [GQEPGQEPGAPHGAPH]; and [A,E,G,P,H,Q] (in random);

repeated or extended to render an oligomer extended insulin or insulin analogue with an extension comprising of from about 100 to about 800 contiguous amino acid residues.

7. An oligomer extended insulin or insulin analogue selected from the group consisting of
A21Q(GQEP)$_{50}$, desB30 human insulin;
A21Q(GAPQ)$_{50}$, desB30 human insulin;
A21Q(GQAP)$_{50}$, desB30 human insulin;
A21Q(GEPH)$_{50}$, desB30 human insulin;
A21Q(GEHP)$_{50}$, desB30 human insulin;
A14E, A21G(GQEP)$_{50}$, B25H, desB30 human insulin;
A14E, A21G(GAPQ)$_{50}$, B25H, desB30 human insulin;
A14E, A21G(GEPH)$_{50}$, B25H, desB30 human insulin;
A14E, A21G(GEHP)$_{50}$, B25H, desB30 human insulin;
A14E, A21G(GAPH)$_{50}$, B25H, desB30 human insulin;
A21G(GEHPGAPHGQEPGQAP)$_{13}$, desB30 human insulin;
A21G(GEH)$_{67}$, desB30 human insulin;
A21G(GQA)$_{67}$, desB30 human insulin;
A21G(GQE)$_{67}$, desB30 human insulin;
A21G(GEQH)$_{50}$, desB30 human insulin;
A21G(GQEPGQEPGQEPGAPH)$_{12}$GQEPGQEP, desB30 human insulin;
A21G(GQEPGQEPGAPHGAPH)$_{12}$GQEPGQEP, desB30 human insulin;
A21G(GQAPGQAPGQAPGAPH)$_{12}$GQAPGQAP, desB30 human insulin;
A21G(GQAPGQAPGAPHGAPH)$_{12}$GQAPGQAP, desB30 human insulin;
A21G[A,E,G,H,P,Q] (random 200 amino acids), desB30 human insulin;
A21G(GHEPGQHP)$_{25}$, desB30 human insulin;
A21G(GQEPGQHP)$_{25}$, desB30 human insulin;
A21G(GQPE)$_{50}$, desB30 human insulin;
A21G(GEQP)$_{50}$, desB30 human insulin;
A21G(GEPQ)$_{50}$, desB30 human insulin;
A21G(GPEQ)$_{50}$, desB30 human insulin;
A21G(GPQE)$_{50}$, desB30 human insulin;
A21G(GQPA)$_{50}$, desB30 human insulin;
A21G(GAQP)$_{50}$, desB30 human insulin;
A21G(GPAQ)$_{50}$, desB30 human insulin;
A21G(GPQA)$_{50}$, desB30 human insulin;
A21G(GHEP)$_{50}$, desB30 human insulin;
A21G(GHPE)$_{50}$, desB30 human insulin;
A21G(GPEH)$_{50}$, desB30 human insulin;
A21G(GPHE)$_{50}$, desB30 human insulin;
A21G(GQEH)$_{50}$, desB30 human insulin;
A21G(GQHE)$_{50}$, desB30 human insulin;
A21G(GHEQ)$_{50}$, desB30 human insulin;
A21G(GHQE)$_{50}$, desB30 human insulin;
A21G(GEQ)$_{67}$, desB30 human insulin;
A21G(GAQ)$_{67}$, desB30 human insulin;
A21G(GQAP)$_{62}$, desB30 human insulin;
A21G(GQAP)$_{75}$, desB30 human insulin;
A21G(GQAP)$_{100}$, desB30 human insulin;
A21G(GQAP)$_{50}$, desB30 human insulin;
A21G(GQAP)$_{125}$, desB30 human insulin;
A21G(GQAP)$_{150}$, desB30 human insulin;
A14E, A21G(GQAP)$_{50}$, B25H, desB30 human insulin;
A14E, A21G(GQAP)$_{75}$, B25H, desB30 human insulin;
A14E, A21G(GQAP)$_{150}$, B25H, desB30 human insulin;
A21G, B1F(GQAP)$_{50}$, desB30 human insulin;
A21G, B1F(GQAP)$_{100}$, desB30 human insulin;
A21G, A22A, A23P, A24Q(GAPQ)$_{49}$, desB30 human insulin;
A21G, A22A, A23Q, A24P(GAQP)$_{49}$, desB30 human insulin;
A21G, A22Q, A23A, A24P(GQAP)$_{49}$, desB30 human insulin;
A21G, A22Q, A23P, A24A(GQPA)$_{49}$, desB30 human insulin;
A21G, A22P, A23A, A24Q(GPAQ)$_{49}$, desB30 human insulin;
A21G, A22P, A23Q, A24A(GPQA)$_{49}$, desB30 human insulin;
A21G(GQAP)$_{56}$, desB30 human insulin;
A21G(GQAP)$_{69}$, desB30 human insulin;
A21G(GQAP)$_{31}$, desB30 human insulin;
A21G(GQAP)$_{37}$, desB30 human insulin;
A21G(GQAP)$_{44}$, desB30 human insulin;
A21G, A22Q, A23P(GQP)$_{66}$, desB30 human insulin;
A21G, A22A, A23Q, A24P(GAQP)$_{37}$, desB30 human insulin; and
A21G, A22A, A23Q, A24P(GAQP)$_{62}$, desB30 human insulin.

* * * * *